(12) United States Patent
Maaskant et al.

(10) Patent No.: US 11,738,343 B2
(45) Date of Patent: *Aug. 29, 2023

(54) APPARATUS, SYSTEM AND METHOD FOR PERFORMING AUTOMATED CENTRIFUGAL SEPARATION

(71) Applicant: QVELLA CORPORATION, Richmond Hill (CA)

(72) Inventors: Robert Maaskant, Richmond Hill (CA); Sanjesh Yasotharan, Toronto (CA); Samad Talebpour, Richmond Hill (CA); Stephen W. Leonard, Unionville (CA); Cyrus Etemad-Moghadam, Fallston, MD (US); Alexander Zahn, Odenton, MD (US)

(73) Assignee: QVELLA CORPORATION, Richmond Hill (CA)

( * ) Notice: Subject to any disclaimer, the term of this patent is extended or adjusted under 35 U.S.C. 154(b) by 132 days.

This patent is subject to a terminal disclaimer.

(21) Appl. No.: 17/338,856

(22) Filed: Jun. 4, 2021

(65) Prior Publication Data

US 2021/0291184 A1 Sep. 23, 2021

Related U.S. Application Data

(63) Continuation of application No. 16/818,095, filed on Mar. 13, 2020, now Pat. No. 11,027,279, which is a
(Continued)

(51) Int. Cl.
*B01L 3/00* (2006.01)
*B01L 7/00* (2006.01)
(Continued)

(52) U.S. Cl.
CPC .... *B01L 3/502753* (2013.01); *B01D 17/0217* (2013.01); *B01D 19/0052* (2013.01);
(Continued)

(58) Field of Classification Search
CPC ......... B01L 3/502753; B01L 3/502715; B01L 3/502738; B01L 7/52; B01L 3/5021;
(Continued)

(56) References Cited

U.S. PATENT DOCUMENTS

| 1,111,001 A | * | 9/1914 | Bartholomew et al. .. B04B 7/06 |
| | | | 192/136 |
| 1,131,675 A | * | 3/1915 | Bunker .................. B04B 15/12 |
| | | | 210/214 |

(Continued)

FOREIGN PATENT DOCUMENTS

| CA | 2779401 | * | 5/2011 | ................ B01L 3/00 |
| CA | 2779401 A1 | * | 5/2011 | ................ B01L 3/00 |

*Primary Examiner* — Joseph W Drodge
(74) *Attorney, Agent, or Firm* — HILL & SCHUMACHER

(57) ABSTRACT

Systems, methods and devices are provided for the automated centrifugal processing of samples. In some embodiments, an integrated fluidic processing cartridge is provided, in which a centrifugation chamber is fluidically interfaced, through a lateral surface thereof, with a microfluidic device, and wherein the integrated fluidic processing cartridge is configured to be inserted into a centrifuge for centrifugation. A cartridge interfacing assembly may be employed to interface with the integrated fluidic processing cartridge for performing various fluidic processing steps, such as controlling the flow of fluids into and out of the centrifugation chamber, and controlling the flow of fluids into the microfluidic device, and optionally for the further fluidic processing of fluids extracted to the microfluidic device. The integrated fluidic processing cartridge may include a super-
(Continued)

natant chamber the extraction of a supernatant thereto, and a diluent chamber for diluting a suspension collected in the centrifugation chamber.

22 Claims, 37 Drawing Sheets

Related U.S. Application Data continuation of application No. 15/311,732, filed as application No. PCT/CA2015/050449 on May 19, 2015, now Pat. No. 10,596,570.

(60) Provisional application No. 61/994,728, filed on May 16, 2014.

(51) Int. Cl.
| | | |
|---|---|---|
| *B04B 5/04* | (2006.01) | |
| *B04B 13/00* | (2006.01) | |
| *B01D 19/00* | (2006.01) | |
| *B01D 17/02* | (2006.01) | |
| *F16K 7/00* | (2006.01) | |
| *B01D 21/26* | (2006.01) | |
| *C12N 15/00* | (2006.01) | |
| *F16K 99/00* | (2006.01) | |
| *C12N 15/10* | (2006.01) | |

(52) U.S. Cl.
CPC .......... *B01D 21/262* (2013.01); *B01L 3/5021* (2013.01); *B01L 3/502715* (2013.01); *B01L 3/502738* (2013.01); *B01L 7/52* (2013.01); *B04B 5/0407* (2013.01); *B04B 5/0421* (2013.01); *B04B 13/00* (2013.01); *C12N 15/1003* (2013.01); *F16K 7/00* (2013.01); *F16K 99/0015* (2013.01); *B01L 2200/027* (2013.01); *B01L 2200/0684* (2013.01); *B01L 2200/10* (2013.01); *B01L 2300/0816* (2013.01); *B01L 2300/0887* (2013.01); *B01L 2300/1822* (2013.01); *B01L 2300/1827* (2013.01); *B01L 2300/1844* (2013.01); *B01L 2400/0409* (2013.01); *B01L 2400/0487* (2013.01); *B01L 2400/0655* (2013.01); *F16K 2099/0084* (2013.01)

(58) Field of Classification Search
CPC ..... B01L 2300/1827; B01L 2200/0684; B01L 2300/1844; B01L 2400/0409; B01L 2400/0487; B01L 2400/0655; B01L 2300/0887; B01L 2200/10; B01L 2200/027; B01L 2300/0816; B01L 2300/1822; B01L 2300/04; B01L 2300/041; B01L 2300/043; B01L 2300/049; B01L 11/00; B01L 11/04; B04B 13/00; B04B 5/0421; B04B 5/0407; B04B 5/10; B04B 7/02; B04B 7/04; B01D 21/262; B01D 19/0052; B01D 17/0217; C12N 15/1003; F16K 99/0015; F16K 7/00; F16K 2099/0084; G01N 1/40; G01N 1/4077; G01N 2001/4083; G01N 2035/00495; G01N 2035/00504
USPC .... 210/360.1, 512.1, 781, 782, 787; 422/72; 435/308.1; 436/177; 494/2, 37, 38, 41, 494/42, 85
See application file for complete search history.

(56) References Cited

U.S. PATENT DOCUMENTS

| | | | | |
|---|---|---|---|---|
| 1,719,132 | A * | 7/1929 | Roberts | B04B 13/00 |
| | | | | 210/139 |
| 2,591,317 | A * | 4/1952 | Tholl | B04B 7/06 |
| | | | | 494/12 |
| 3,249,295 | A * | 5/1966 | Childs | B04B 5/0428 |
| | | | | 494/37 |
| 3,880,592 | A * | 4/1975 | Kelley | G01N 33/491 |
| | | | | 422/50 |
| 4,522,718 | A * | 6/1985 | Henkel | B04B 11/05 |
| | | | | 210/373 |
| 6,198,948 | B1 * | 3/2001 | Sudo | H04M 1/724 |
| | | | | 455/566 |
| 8,975,060 | B2 * | 3/2015 | Talebpour | B01L 3/5021 |
| | | | | 435/243 |
| 10,596,570 | B2 * | 3/2020 | Maaskant | F16K 99/0042 |
| 11,027,279 | B2 * | 6/2021 | Maaskant | B01D 17/0217 |
| 2002/0119078 | A1 * | 8/2002 | Jansa | B01L 7/52 |
| | | | | 422/400 |
| 2011/0039303 | A1 * | 2/2011 | Jovanovich | B01L 3/50273 |
| | | | | 536/23.1 |
| 2012/0115705 | A1 * | 5/2012 | Sharon | B04B 5/0407 |
| | | | | 494/56 |
| 2012/0314528 | A1 * | 12/2012 | Roth | B01F 35/81 |
| | | | | 366/160.5 |
| 2013/0252796 | A1 * | 9/2013 | Von Stetten | B04B 7/08 |
| | | | | 494/37 |
| 2014/0098252 | A1 * | 4/2014 | Chang | G01N 35/00732 |
| | | | | 348/207.99 |
| 2014/0287966 | A1 * | 9/2014 | Gray | G01N 21/01 |
| | | | | 506/39 |

* cited by examiner

APPARATUS, SYSTEM AND METHOD FOR PERFORMING AUTOMATED CENTRIFUGAL SEPARATION

CROSS-REFERENCE TO RELATED APPLICATION

This application claims priority to U.S. Provisional Application No. 61/994,728, titled "APPARATUS, SYSTEM AND METHOD FOR PERFORMING AUTOMATED CENTRIFUGAL SEPARATION" and filed on May 16, 2014, the entire contents of which is incorporated herein by reference.

BACKGROUND

The present disclosure relates to sample preparation, centrifugal separation, and microfluidic processing of fluids.

Pathogen detection in whole blood samples using molecular techniques requires a sample treatment process which yields a suspension of target nucleic acids which is sufficiently free of PCR inhibitors, interferents and non-target nucleic acids. The sample treatment process is closely tied to the amplification and detection techniques utilized and as such are vital to sensitive and specific detection of target microbes. For instance, the number of target microbial cells in whole blood, on the order of $10^1$ CFU/mL, is vastly outnumbered by blood cells, on the order of $10^{10}$/mL. Blood cells are therefore sources of large amount of background DNA, PCR inhibitors, RNase, and fluorescence quenchers. Moreover, dead microbes and nucleic acid from such microbes may also be present in the sample from previously treated infections. This imposes strict functionality requirements on the nucleic acid based pathogen detection platforms.

Existing methods of performing sample preparation on whole blood samples typically consist of the following steps: (i) the blood sample is subjected to some means of lysing the blood cells and microbial cells, either selectively or non-selectively with respect to the target microbes; (ii) removal or inactivation of inhibitors and interferents to PCR and detection; and (iii) removal of non-target nucleic acid or enhanced amplification and detection strategies for increasing specificity with respect to target microbes and live versus dead microbes.

These steps are typically performed either separately or in combination and with varying levels of efficacy in accordance with the tolerance characteristics of downstream processes. Most existing pathogen detection platforms rely on extraction and purification of the target nucleic acids prior to amplification and detection using PCR or RT-PCR, and are poorly-suited for automation in applications involving low pathogen concentrations.

SUMMARY

Systems, methods and devices are provided for the automated centrifugal processing of samples. In some embodiments, an integrated fluidic processing cartridge is provided, in which a centrifugation chamber is fluidically interfaced, through a lateral surface thereof, with a microfluidic device, and wherein the integrated fluidic processing cartridge is configured to be inserted Into a centrifuge for centrifugation. A cartridge interfacing assembly may be employed to interface with the integrated fluidic processing cartridge for performing various fluidic processing steps, such as controlling the flow of fluids into and out of the centrifugation chamber, and controlling the flow of fluids into the microfluidic device, and optionally for the further fluidic processing of fluids extracted to the microfluidic device. The integrated fluidic processing cartridge may include a supernatant chamber the extraction of a supernatant thereto, and a diluent chamber for diluting a suspension collected in the centrifugation chamber.

Accordingly, in one aspect, there is provided a method of performing centrifugal separation and microfluidic processing using an integrated fluidic processing cartridge;
the integrated fluidic processing cartridge comprising:
a macrofluidic centrifugation chamber, wherein a distal region of the macrofluidic centrifugation chamber is configured to collect a sediment under the application of centrifugal force;
a microfluidic device having an inner surface and an outer surface, wherein the inner surface is attached to a lateral surface of the macrofluidic centrifugation chamber, and wherein the microfluidic device comprises one or more fluidic components that are configured to be actuated through the outer surface;
wherein a sediment extraction port is provided within the macrofluidic centrifugation chamber and wherein the sediment extraction port is in fluid communication, through the lateral surface, with a sediment extraction channel of the microfluidic device for extraction of the sediment to the microfluidic device;
the method comprising:
providing a liquid sample within the macrofluidic centrifugation chamber;
centrifuging the integrated fluidic processing cartridge with a centrifugation device such that the sediment is collected within the distal region;
applying a pressure difference between the sediment extraction channel of the microfluidic device and the macrofluidic centrifugation chamber, such that a concentrated suspension comprising at least a portion of the sediment flows through the sediment extraction port and into the microfluidic device, thereby transferring the concentrated suspension to the microfluidic device; and
fluidically processing the concentrated suspension within the microfluidic device by actuating one or more of the fluidic components through the outer surface.

In another aspect, there is provided a system for performing centrifugal separation and microfluidic processing, said system comprising:
an integrated fluidic processing cartridge comprising:
a macrofluidic centrifugation chamber, wherein a distal region of said macrofluidic centrifugation chamber is configured to collect a sediment under the application of centrifugal force;
a microfluidic device having an inner surface and an outer surface, wherein said inner surface is attached to a lateral surface of said macrofluidic centrifugation chamber, and wherein said microfluidic device comprises one or more fluidic components that are configured to be actuated through said outer surface;
wherein a sediment extraction port is provided within said macrofluidic centrifugation chamber and wherein said sediment extraction port is in fluid communication, through said lateral surface, with a sediment extraction channel of said microfluidic device for extracting the sediment thereto; and
a centrifugation device comprising:
a rotor; and a receptacle pivotally connected to said rotor, wherein said receptacle is configured to receive said integrated fluidic processing cartridge such that said outer surface is laterally and outwardly oriented relative to a rotational axis of said rotor when said rotor is at rest;

a cartridge interfacing assembly configured to be removably interfaced with said integrated fluidic processing cartridge when said rotor is at rest; and a control and processing unit operably interfaced with the centrifugation device and the cartridge interfacing assembly, wherein said control and processing unit is configured to:
control said centrifugation device to centrifuge said integrated fluidic processing cartridge;
control said cartridge interfacing assembly to interface said cartridge interfacing assembly with said integrated fluidic processing cartridge when said centrifugation device is at rest;
control said cartridge interfacing assembly to actuate the application of a pressure difference between said macrofluidic centrifugation chamber and said sediment extraction channel to extract, onto the microfluidic device, a concentrated suspension comprising at least a portion of the sediment; and to fluidically process the concentrated suspension on the microfluidic device.
control said cartridge interfacing assembly to actuate the one or more fluidic components to fluidically process the concentrated suspension on the microfluidic device.

In another aspect, there is provided an integrated fluidic processing cartridge for performing macrofluidic separation and microfluidic processing, said integrated fluidic processing cartridge comprising:

a macrofluidic centrifugation chamber, wherein a distal region of said macrofluidic centrifugation chamber is configured to collect a sediment under the application of centrifugal force;

a microfluidic device having an inner surface and an outer surface, wherein said inner surface is attached to a lateral surface of said macrofluidic centrifugation chamber, and wherein said microfluidic device comprises one or more fluidic components that are configured to be actuated through said outer surface;

wherein a sediment extraction port is provided within said distal region of said macrofluidic centrifugation chamber, and wherein said sediment extraction port is in fluid communication, through said lateral surface, with a sediment extraction channel of said microfluidic device, for extracting the sediment thereto.

In another aspect, there is provided a microfluidic diaphragm valve comprising:

a base layer having a part formed in a surface thereof;

a microfluidic layer having a first surface and an opposing second surface, wherein said microfluidic layer is provided on said base layer such that said second surface is attached to said surface of said base layer, said microfluidic layer comprising a lateral microfluidic channel in fluid communication with a valve seat aperture, wherein said valve seat aperture is positioned over said port, and wherein said valve seat aperture extends through said microfluidic layer;

a membrane adhered to said second surface of said microfluidic layer, said membrane enclosing said valve seat aperture; and a plunger positioned to contact an external surface of said membrane, such that upon application of a sufficient inwardly directed force to said plunger, said plunger is received within said valve seat aperture and said membrane forms a seal against said port.

In another aspect, there is provided a method of performing centrifugal separation using an integrated fluidic processing cartridge;
the integrated fluidic processing cartridge comprising:
a macrofluidic centrifugation chamber, wherein a distal region of the macrofluidic centrifugation chamber is configured to collect a sediment under the application of centrifugal force, and wherein a supernatant extraction port is provided within the distal region of the macrofluidic centrifugation chamber;
a supernatant chamber having a supernatant delivery port formed therein; and
a microfluidic device having an inner surface and an outer surface, wherein the inner surface is attached to a lateral surface of the macrofluidic centrifugation chamber;
wherein the supernatant extraction port is in fluid communication, through the lateral surface, with a supernatant delivery channel of the microfluidic device, and wherein the supernatant delivery port is in fluid communication, through the lateral surface, with the supernatant delivery channel of the microfluidic device for extracting a substantial portion of a supernatant from the macrofluidic centrifugation chamber into the supernatant chamber; and
the method comprising:
providing a liquid sample within the macrofluidic centrifugation chamber;
centrifuging the integrated fluidic processing cartridge with a centrifugation device such that the sediment is collected within the distal region;
applying a pressure difference between the supernatant chamber and the macrofluidic centrifugation chamber, such that the supernatant flows through the supernatant delivery channel, thereby transferring the supernatant to the supernatant chamber.

A further understanding of the functional and advantageous aspects of the disclosure can be realized by reference to the following detailed description and drawings.

BRIEF DESCRIPTION OF THE DRAWINGS

Embodiments will now be described, by way of example only, with reference to the drawings, in which:

FIG. 18O illustrates the engagement of the cartridge interfacing assembly with the receptacle supporting the integrated fluidic processing device.

DETAILED DESCRIPTION

Figure 1:
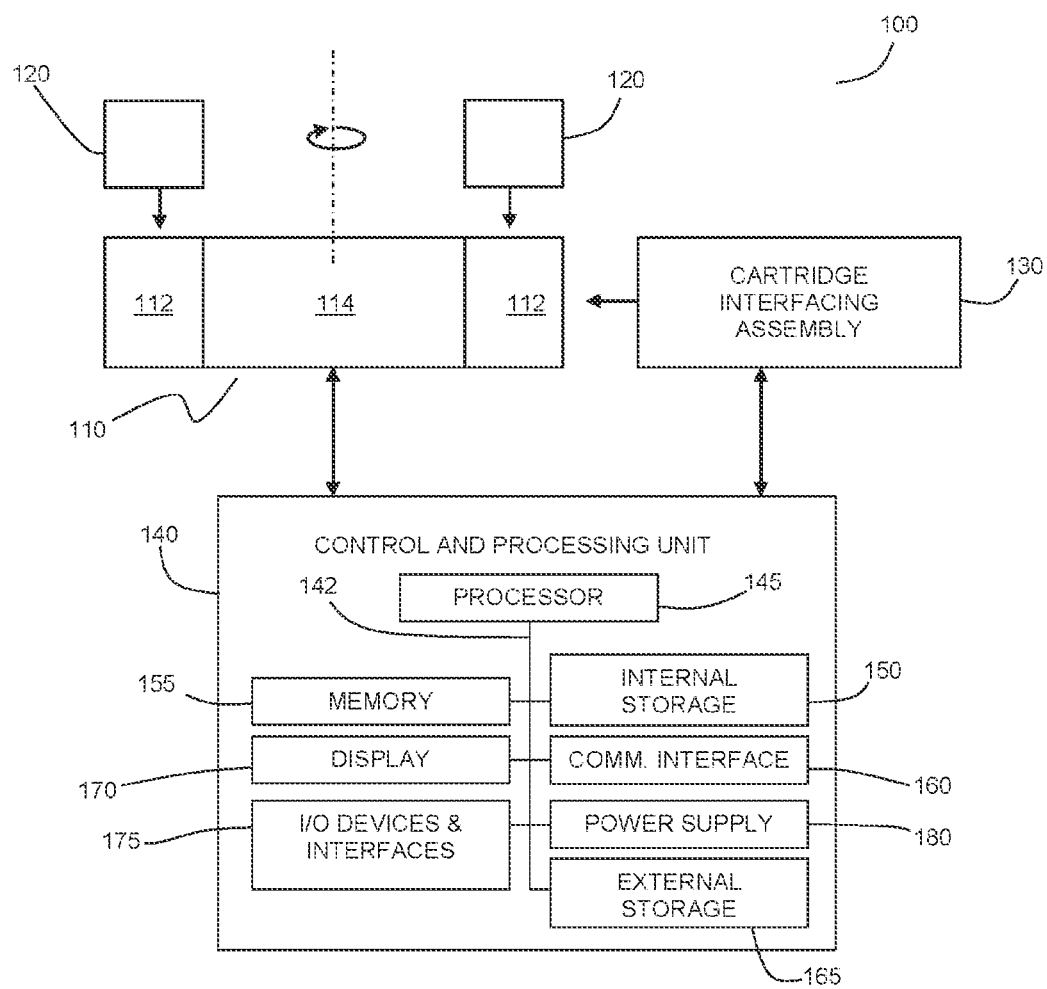
FIG. 1 shows a schematic of an example system for performing automated centrifugation and washing with an integrated fluidic processing cartridge.

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms "comprises" and "comprising" are to be construed as being inclusive and open ended, and not exclusive. Specifically, when used in the specification and claims, the terms "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. Unless otherwise specified, the terms "about" and "approximately" mean plus or minus 25 percent or less.

It is to be understood that unless otherwise specified, any specified range or group is as a shorthand way of referring to each and every member of a range or group individually, as well as each and every possible sub-range or sub-group encompassed therein and similarly with respect to any sub-ranges or sub-groups therein. Unless otherwise specified, the present disclosure relates to and explicitly incorporates each and every specific member and combination of sub-ranges or sub-groups.

As used herein, the term "on the order of", when used in conjunction with a quantity or parameter, refers to a range spanning approximately one tenth to ten times the stated quantity or parameter.

Unless defined otherwise, all technical and scientific terms used herein are intended to have the same meaning as commonly understood to one of ordinary skill in the art. Unless otherwise indicated, such as through context, as used herein, the following terms are intended to have the following meanings:

As used herein, the phrase "centrifugal separation" refers to a process of centrifugation of a sample fluid containing particulate or solid material, whereby sedimentation of such particulate or solid materials occurs, thereby producing a sediment. The phrase "sediment" generally refers to one or more particles that are collected, within a distal region of a centrifugation device, after the application of a centrifugal force. One non-limiting example of a sediment is one or more microbial cells. A sediment need not be collected at the bottom surface of a centrifugation chamber, and may instead be formed near the bottom of the centrifugation chamber, or at the interface between a supernatant and a cushioning liquid, as described in detail here below.

As used herein, the phrases "wash" and "washing" refers to a process involving the addition of a diluent (or wash liquid/buffer) to a solid or suspension sample, mixing of the diluent with the sample (optionally to re-suspend a sediment) to obtain a suspension, and centrifuging the suspension.

As used herein, the term "microfluidic channel" refers to a fluidic channel having a cross-sectional dimension less than 1 mm.

As used herein, the term "microfluidic device" refers to a fluidic device having at least one microfluidic channel.

As used herein, the term "macrofluidic chamber" refers to a fluidic chamber or chamber, where all dimensions of the fluidic chamber or chamber exceed 1 mm, and where a volume of the chamber exceeds 500 microliters.

Integrated Apparatus for Centrifugation and Washing

Referring now to FIG. 1, an illustration is provided of an example integrated system 100 for performing automated centrifugal separation or automated centrifugal separation with washing. Example system 100 includes centrifuge 110, which receives one or more integrated fluidic processing cartridges 120 for centrifugal separation. Centrifuge 110 includes one or more receptacles 112 which are connected to a motorized rotor 114 and are configured to receive integrated fluidic processing cartridges 120. The cartridge receptacles 112 may be, for example, of the fixed angle type or the swinging bucket type which are common in laboratory centrifuges (e.g. each receptacle 112 may be pivotally connected to the motorized rotor 114).

Cartridge interface assembly (unit) 130 is configured to removably engage (or interface) with an integrated fluidic processing cartridge 120 when the motorized rotor 114 is at rest, for controlling the flow of fluids within integrated fluidic processing cartridge 120. The interlacing of the cartridge interfacing assembly with the integrated fluidic cartridge may occur, for example, via a direct interface between the cartridge interfacing assembly and the integrated fluidic cartridge 120, or, for example, via an interface (e.g. an actuation interface) on the centrifuge 110 (e.g. on the motorized rotor 114 or cartridge receptacle 112). Centrifuge 110 and cartridge interfacing assembly 130 are controlled via control and processing unit 140.

As described in further detail below, each integrated fluidic processing cartridge 120 includes a centrifugation chamber for centrifugal separation during rotation of the motorized rotor 114. In some embodiments, the centrifugation chamber may be a microfluidic chamber. In various example embodiments described below, the centrifugation chamber is a macrofluidic centrifugation chamber capable of performing centrifugal separations for fluid volumes exceeding 500 microliters.

Integrated fluidic processing cartridge 120 may contain ports, conduits, valves and chambers to enable removal of the supernatant from the macrofluidic centrifugation chamber and optionally storage of the removed supernatant on the cartridge while integrated fluidic processing cartridge 120 is housed within the centrifuge 110. Integrated fluidic processing cartridge 120 may also include ports, conduits, valves, and chambers to enable automated washing while integrated fluidic processing cartridge 120 is housed within centrifuge 110.

Figure 2A:
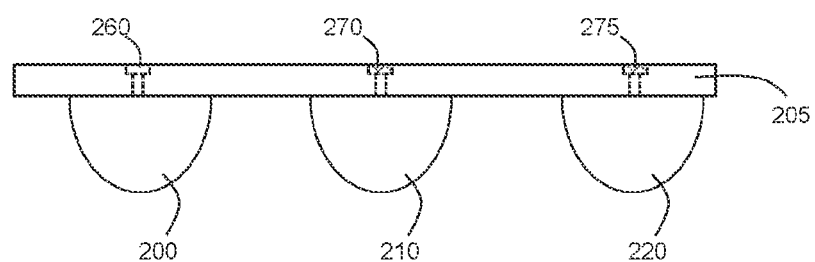
FIGS. 2A-C show different views of an example integrated fluidic processing cartridge for centrifugation and washing.
Figure 2B:
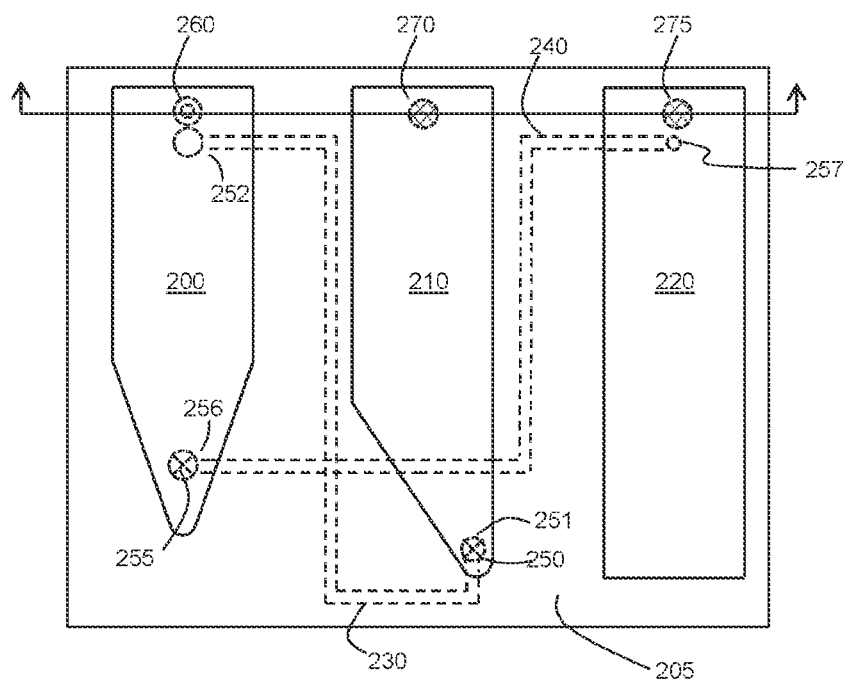
Figure 2C:
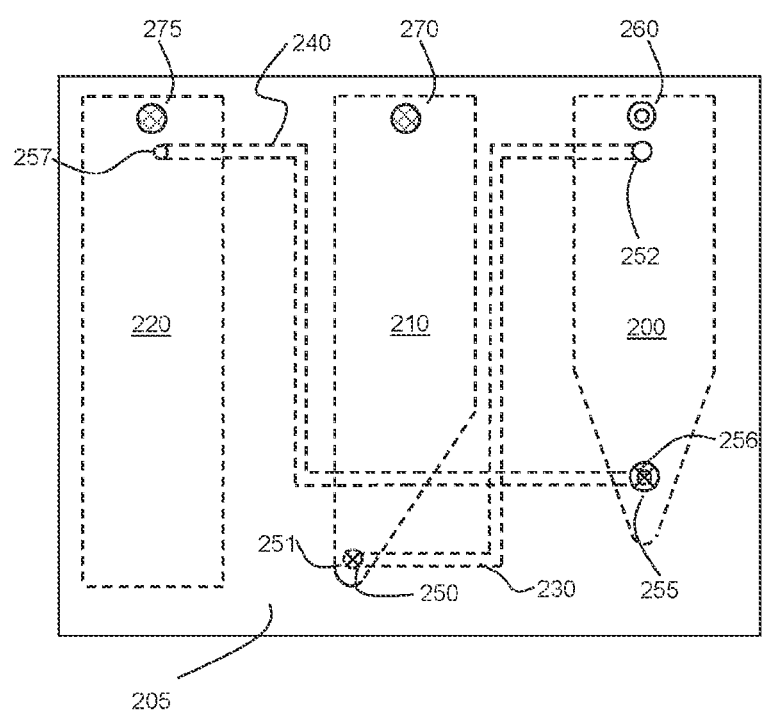

An illustration of an example embodiment of integrated fluidic processing cartridge 120 is shown in FIGS. 2A-C, where FIGS. 2A, 2B and 2C show top, front and back views respectively (FIG. 2C shows the outer lateral surface of the device). In this embodiment integrated fluidic processing cartridge 120 includes macrofluidic centrifugation chamber 200, diluent chamber 210 and supernatant chamber 220. In the example embodiment shown, macrofluidic centrifugation chamber 200 has a conical or round bottom shape, and a smooth inner surface in order to minimize adsorption or trapping of the sedimented particulate matter during centrifugation. The centrifugation chamber 200 is oriented in the centrifuge rotor 110 such that the centrifugal force acts in the direction of the conical or round bottom of the chamber. Diluent chamber 210 includes a diluent liquid, whose composition is selected to conform to the requirements of the final medium into which the particles will be resuspended which may be dictated by subsequent processing requirements. The diluent chamber 210 may have a conical or narrowing bottom tip that enables the extraction of wash liquid with minimal residual. One or more additional diluent chambers may be included together with the required conduits, and valves, to enable one or more diluent liquids of different compositions to be used in the wash process. Supernatant chamber 220 may be empty, or may include an adsorbent material, such as a wicking material. Supernatant chamber may be employed to collect the supernatant, and/or employed as a waste chamber.

Automated separation of a suspension is performed within macrofluidic centrifugation chamber 200 by performing centrifugal sedimentation of the particulate material in the suspension followed by flowing of supernatant from macrofluidic centrifugation chamber 200 to supernatant chamber 220. One or more washes may be performed by the additional sequential steps of flowing a diluent liquid from diluent chamber 210 into macrofluidic centrifugation chamber 200, optionally mixing the diluent and the residual supernatant, performing centrifugation, and flowing supernatant from macrofluidic centrifugation chamber 200 to supernatant chamber 220. As described in additional embodiments that are provided below, integrated fluidic processing cartridge may include additional features and components, such as, but not limited to, a lysing chamber and/or one or more assay chambers or wells for subsequent processing and/or assaying of the washed sample.

In some example embodiments of the present disclosure, the integrated fluidic processing cartridge is configured to support automated centrifugal separation and optionally dilution/washing in a closed configuration. In the present disclosure, the term "closed configuration" refers to a cartridge structure that prevents the addition or removal of liquids from the cartridge during fluidic processing. Whereas various example embodiments may employ vents and the injection of air (or other gases) into the cartridge or the evacuation of air (or other gases) from the cartridge, gas permeable membranes or filters of sufficiently small pore size may be placed in such air paths to prevent or minimize the egress of hazardous particles or fluids and the ingress of contaminants or interferents.

In the example embodiment illustrated in FIGS. 2A-2C, the chambers are interfaced with a microfluidic device 205, which has internal fluidic channels that provide fluidic connections between the chambers. In various example embodiments described below, the microfluidic device 205 includes one or more microfluidic layers, and has an inner surface and an outer surface. In the present example embodiment, the inner surface is attached to lateral surfaces of the macrofluidic centrifugation chamber, the diluent chamber 210, and the supernatant chamber 220, as shown in FIGS. 2A and 2B. The microfluidic device 205 is in fluid communication with the chambers through ports (holes, apertures or vias) formed through the walls of the chambers. Microfluidic device 205 includes channels (which may be microfluidic channels) for fluid flow between chambers and ports, for allowing fluidic movements into or out of chambers. Microfluidic device 205 may also include one or more valves for controlling fluid flow. Fluid flow may be produced by any suitable flow mechanism. In one example implementation, fluid flow between different locations within the integrated fluidic processing cartridge is produced using interfaces to a gas (e.g. air) displacement device that generates a pressure difference between chambers, for gas-displacement induced fluidic movements.

In one example implementation, the chambers 200, 210 and 220 may be formed from plastic material (such as, but not limited to, polycarbonate, polypropylene. PET, polystyrene, cyclic olefins, acrylics, polyethylene, polyurethanes, PTFE. PEEK, PVC), either individually or in combination, using a fabrication process such as injection molding, casting, machining, 3D printing or other methods and materials known to those skilled in the art. In addition to the forming process, some or all of the chambers 200, 210 or 220 may optionally need further finishing or surface treatment to ensure a smooth low binding surface. Such finishing may be carried out by using various processes either individually, or in combination such as mechanical polishing, or chemical coating of the inner surface by silicones, nonionic silanes, treatment to cause the surface to by hydrophobic, treatment to cause the surface to be hydrophilic. BSA, PEG, SAMs or other similar compounds, via dip coating processes, spray coating, or other methods known to those skilled in the art with or without following curing steps as required by the process used. The chambers may be formed to possess a back surface, each chamber having one or more ports formed therein, which interface with fluidic channels of the microfluidic device 205 through the inner surface of the microfluidic device.

In one example embodiment that is intended for the detection of pathogen microbial cells in whole blood (or, for example, blood added to culture medium), the volume of centrifugation, dilution and supernatant chambers may be, respectively, in the range of 0.1-60 mL, 0.5-120 mL, and 0.6-120 mL. The more preferred examples ranges for the diluent and supernatant chambers are, respectively, 0.5-10 mL, 1.5-20 mL, and 1.5-20 mL. According to various example implementations, depending on the geometry and size of the chambers, the diameters of their associated holes, ports and vents may be selected to be in the 0.1 mm-3 mm range. According to various example implementations, the width of the conduits may vary in 0.1 mm to 3 mm range. According to various example implementations, the height of the conduits may vary in 0.025 mm to 1 mm range.

In one example implementation, the microfluidic device 205 may be a laminate structure formed from multiple layers which contain the fluidic channels (conduits), chambers, and fluidic components that may be externally actuated, such as valves and gas permeable interfaces that may be employed for fluid control.

The microfluidic device may be formed via a wide variety of fabrication processes. Non-limiting examples of fabrication processes include injection molding, hot-embossing, micromachining, punching, die cutting, soft lithography, laser cutting, water jet cutting, plotting cutters or other methods know to those skilled in the art. Layers may be made with materials such as, but not limited to, polycarbonate, PET, polypropylene, PDMS, cyclic olefins, PMMA, photoresists, silicon wafers, glass, foils such as aluminum or other materials which are known to those skilled in the art.

The microfluidic device 205 may be formed by lamination of its constituent layers by methods such as, but not limited to, adhesive bonding, thermal bonding, ultrasonic bonding, or other bonding methods known to those in the art. In addition some or all of the layers may optionally require surface treatment to provide additional properties such as low energy non-binding, enhanced hydrophilic or enhanced hydrophobic properties to prevent adhesion of compounds within the sample to the walls of the device, or allow ease of fluid passage in the chambers or channels, or act as passive fluid control elements, as is known to those skilled in the art. These properties can be established by chemical treatment of the materials with compounds such as, but not limited to, silicones, silanes, PEG, BSA or other materials known to those skilled in the art. The inner surface of the microfluidic device 205 may be bonded to the lateral surface of the chambers to form the integrated fluidic processing cartridge 120. In some embodiments, the back surfaces of the chambers are co-planar, and the inner surface of the microfluidic device 205 is a planar surface.

In an alternative example embodiment, some or all of the fluidic components of the microfluidic device 205 may be integrally formed with the chambers, thereby forming an intermediate device having a lateral surface, and any remaining layers of the microfluidic device 205 may be bonded to the lateral surface to form the integrated fluidic processing cartridge 120.

In other example embodiments, one or more of the supernatant chamber and the diluent chamber (or a plurality thereof) may be externally provided relative to the integrated fluidic processing cartridge, and externally interfaced thereto. For example, the ports provided on the lateral surface of the centrifugation chamber may include fluidic connectors that are suitable for forming a fluidic connection (directly or indirectly) with one or more external diluent chambers, supernatant chambers, or other external fluidic reservoirs (for example, an external lysis buffer, external reagent, and/or external growth medium). In one example implementation, one or more external chambers may be provided on (e.g. housed within or received within) the cartridge interfacing assembly, such that the one or more external chambers may be removably fluidically interfaced with the integrated fluidic processing cartridge. In one example implementation, a port within the macrofluidic centrifugation chamber may be fluidically interfaced with the microfluidic device, as described above, and the microfluidic device may include a fluidic connector, such that the macrofluidic centrifugation chamber is brought into fluid communication with the external chamber through the microfluidic device. In such an example embodiment, the microfluidic device may include one or more valves for optionally restricting the flow of fluid between the macrofluidic centrifugation chamber and the external chamber.

Referring again to the non-limiting example embodiment illustrated in FIGS. 2A-C, diluent chamber 210 and supernatant chamber 220 are each connected, through microfluidic device 205, to macrofluidic centrifugation chamber 200 via diluent delivery channel 230 and supernatant delivery channel 240, respectively. Diluent delivery channel 230 is fluidically connected to diluent delivery port 252 formed in the lateral wall of the macrofluidic centrifugation chamber 200 and to diluent extraction port 251 formed in diluent chamber 210 for the delivery of diluent from the diluent chamber 210 to the macrofluidic centrifugation chamber 200. Similarly, supernatant delivery channel 240 is fluidically connected supernatant extraction port 256 and supernatant delivery port 257 for the extraction of supernatant from the macrofluidic centrifugation chamber 210 to the supernatant chamber 220.

In the example embodiment illustrated in FIGS. 2A-C, diluent chamber 210 and supernatant chamber 220 each also contain (optionally pierceable) vents 270 and 275, respectively, which are housed in microfluidic device 205 and vent to atmospheric pressure though a surface of the integrated fluidic processing cartridge. In one example implementation, one the vents may be accessible through an outer lateral surface of the microfluidic device 205. In another example implementation, one or more of the vents may be accessible through a lateral surface of the respective chamber, where the vent is located in a portion of the lateral surface that is not attached to the microfluidic device. In another example implementation, one or more of the vents may be accessible through an upper or lower surface of the respective chamber in which the vent is located (as opposed to through a lateral surface). The chambers 210 and 220 also contain ports 251 and 257 respectively and may otherwise be closed. Macrofluidic centrifugation chamber 200 is also in fluidic communication with port 260 that is housed in microfluidic device 205 and accessible through a surface of the integrated fluidic processing device. Macrofluidic centrifugation chamber 200 may also contain ports 256 and 252 and may be otherwise closed.

In one example implementation, a pressure difference may be applied together with coordinated actuation of valves in order to effect liquid transfer to and from chambers of the integrated fluidic processing device. Flow in diluent delivery channel 230 may be controlled by diluent control valve 250 which may be located at any position along diluent delivery channel 230, but may be preferentially located proximal to diluent extraction port 251. Flow in supernatant delivery channel 240 may be controlled by supernatant control valve 255 which may be located at any position along supernatant delivery channel 240, but may be preferentially located proximal to supernatant extraction port 256. Valves 250 and 255 may be actuated through the outer surface of microfluidic device 205, as shown in FIG. 2C.

In one example implementation, the transfer of diluent from diluent chamber 210 to macrofluidic centrifugation chamber 200 may be achieved by selectively opening diluent control valve 250 and selectively applying a negative differential pressure at port 260 relative to diluent chamber 210. Similarly, the transfer of liquid from macrofluidic centrifugation chamber 200 to supernatant chamber 220 may be achieved by selectively opening supernatant control valve 255 and selectively applying a positive differential pressure at port 260 relative to supernatant chamber 220. Accordingly, the movement of liquid within the integrated fluidic cartridge may be controlled by the application of a positive or negative gauge pressure at the port 260 within the macrofluidic centrifugation chamber in combination with the selective actuation of the valves between the macrofluidic centrifugation chamber and the various chambers.

In an alternative embodiment, vents 270 and 275 may be configured as ports at which an air displacement device (e.g. or a gas displacement device) can be engaged and port 260 may be configured as an air vent. The transfer of liquid from chamber 210 to chamber 200 may in this case performed by applying a positive differential pressure at port 270 relative to chamber 200, and liquid transfer from chamber 200 to chamber 220 is performed by applying a negative differential pressure at port 275 relative to chamber 200. Valves 250 and 255 are open during these respective liquid transfer operations and may optionally be omitted from the integrated fluidic processing cartridge ii not required for other reasons or modes of operation described herein.

The air displacement device (gas displacement device), which is connected fluidically to port 260 (and/or optionally configured to interface with ports 270 or 275) may be, for example, a syringe pump, peristaltic pump, bellows pump or any other pump or air displacement device which can controllably deliver or remove air from the cartridge via the connected port. It will be understood that the air displacement devices described in the example embodiments provided below may employ air, or any other gas, in order to induce the flow of liquids due to the establishment of a pressure differential between different portions of integrated fluidic processing cartridge 120. For example, in some embodiments, a gas source may be interfaced with a pressurization device (e.g. a pump) in order to control the flow of liquids.

In some embodiments, the opening of the valves, and the application of a pressure differential between port 260 and vents 270 or 275, is performed when integrated fluidic processing cartridge 120 is at rest and under control of cartridge interfacing assembly 130, which may selectively engage with the outer surface of microfluidic device 205 when integrated fluidic processing cartridge 120 is housed within the centrifugation device, as described in further detail below. In such cases, valves 250 and 255 may be configured to be in a closed configuration when cartridge interfacing assembly 130 is disengaged and when centrifuge 110 is performing centrifugation (examples of such valves are provided below).

An additional valve (not shown) may be provided on the fluid path between port 260 and macrofluidic centrifugation chamber 200 in order to prevent fluid from entering the air path during an optional mixing operation. In addition, or as an alternative, a gas permeable membrane that prevents the passage of fluid may be placed in the path between macrofluidic centrifugation chamber 200 and port 260 to prevent fluid from reaching port 260. This gas-permeable membrane may also be configured to serve as a filter to prevent the ingress of airborne microbes from the environment or from the air displacement device. Alternatively, the path between port 260 and macrofluidic centrifugation chamber 200 can be designed to possess high fluidic resistance, such that under the prevailing conditions, liquid will be prevented from proceeding all the way to port 260. Likewise an additional valve, gas-permeable membrane or high fluidic resistance conduit may be placed between chambers 210 and vent 270 and between chamber 220 and vent 260 to prevent the egress of liquid from the cartridge and/or the egress or ingress of pathogens and other contaminants via these ports.

During the centrifugation steps, it will typically be important to ensure that liquid does not flow between chambers. It is noted that if ports 252 and 257 remain above the surface of the liquid in chambers 200 and 220, respectively, during centrifugation, and valves 255 and 250 remain open, liquid from the chambers 200 and 210 will fill the channels 240 and 230 up to the free surface levels in the respective chambers but liquid will not flow into chambers 220 and 200, respectively. Accordingly, in some example implementations, valves 255 and 250 may optionally be omitted from the cartridge unless required for modes of fluid transfer described above, or other reasons or modes of operation.

In some example implementations, valves 255 and 250 may be closed during centrifugation to prevent the liquid from entering channels 240 and 230 respectively. In this case the valves are preferably configured to co-operate with one or more latching mechanisms, such that the valves remains closed when the cartridge interfacing assembly 130 is not engaged with the cartridge 120. It is noted that it may be preferable to close one or more of the valves prior to centrifugation, since high fluidic pressures may develop in the distal regions of chambers 200 and 210 and channels 240 and 230. For example, pressures in the range of 100 psi, 200 psi or 400 psi or greater may occur as a result of high centrifugal speeds. The chambers can thus be formed such that such pressures can be withstood. Suitable materials and geometries of the chambers for withstanding such pressures will be known to those skilled in the art. However, some methods for construction of the microfluidic device 205 may not be able to sustain these pressures such as, for example, laminates bonded with pressure sensitive adhesives. Accordingly, and depending on the centrifugal force applied, it may be necessary to locate valves at the opening to the chambers in order to prevent fluids from exiting the chambers and entering the conduits during centrifugation. In such cases, it may also be preferable to evacuate liquid from conduits prior to centrifugation.

When latching valves (e.g. valves having an integrated latching mechanism, or valves configured to be actuated by a latching mechanism) are employed, the cartridge interfacing assembly 130 may be employed to actively and selectively, as required, engage the latching mechanism to open the valves when the cartridge interfacing assembly 130 is Interfaced with the integrated fluidic processing cartridge, and then to close and relatch the valves prior to disengagement from the cartridge for subsequent centrifugal operations. Some valves and associated latching mechanisms may be configured to be self-latching, such that they latch into a closed position upon disengagement of the cartridge interfacing assembly.

Non-limiting examples of suitable latching mechanisms include a ratchet device which locks the valve closed and is released by the cartridge interfacing assembly to open the valve, or a spring-loaded assembly which holds the valve closed by spring force and which is overcome by the cartridge interfacing assembly to open the valve. Such mechanisms, and other types of known latching mechanisms, may be adapted for the present purpose by those skilled in the art. The latching mechanism may be integrated into the cartridge 120 or may be integrated into a cartridge receptacle 112 included as part of centrifuge 110 in FIG. 1.

Sample (e.g. an original sample or a pre-processed sample) may be introduced into integrated fluidic processing cartridge 120 according to many different embodiments and methods. In one example embodiment, integrated fluidic processing cartridge 120 may include a removable lid or cap that may be opened to introduce a sample into the cartridge, such as directly into macrofluidic centrifugation chamber 200, where the removable cap or lid is sealable (e.g. with an O-ring or other suitable mechanism) in an air-tight manner. Alternatively the lid or cap may contain a pierceable membrane which allows a needle to penetrate the membrane and deposit the sample into the macrofluidic centrifugation chamber. Such a pierceable membrane should be resealable and capable of maintaining a seal to the extent that the pressures required for optional liquid transfer embodiments described above can be maintained in the microfluidic centrifugation chamber. Alternatively such a pierceable membrane may be provided elsewhere on the cartridge 120 or microfluidic device 205 and equipped with a conduit to allow flow to the centrifugal chamber and optionally a shut off valve to prevent loss of fluid or pressure during subsequent operations.

Figure 5:
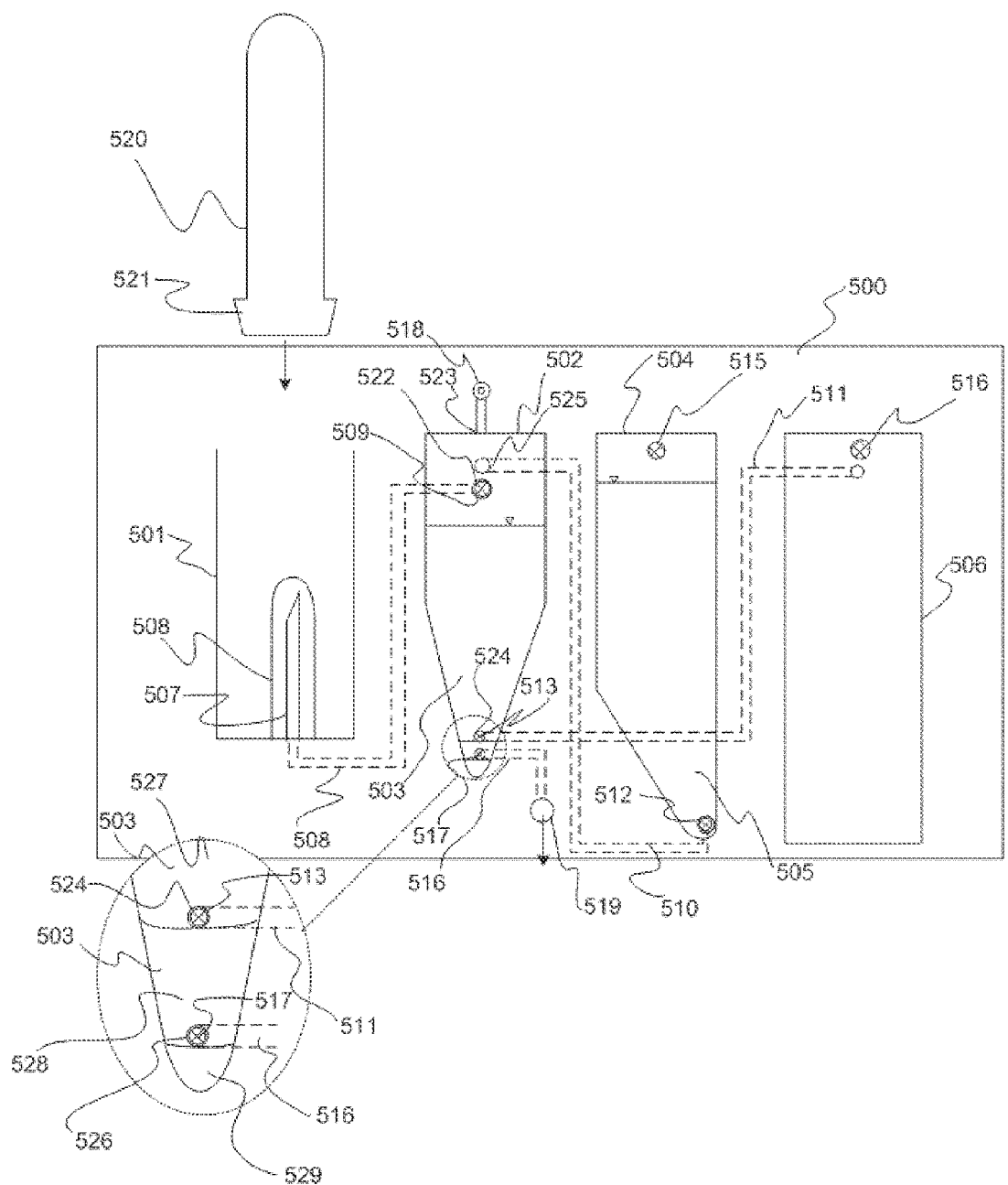
FIG. 5 is an illustration of an example integrated fluidic processing cartridge configured for extraction of a sample directly from a collection tube, and subsequent centrifugation and washing, to obtain a concentrated and purified suspension of microbial cells.

In another example embodiment the sample may be initially provided in another chamber within integrated fluidic processing cartridge 120, such as in a sample receiving chamber, and where the sample may be controllably introduced into the macrofluidic centrifugation chamber according to the valving and flow actuation methods described herein. A further alternative example embodiment for introducing a sample into integrated fluidic processing cartridge 120 is illustrated in FIG. 5 and described in further detail below.

Following centrifugal separation and optionally the washing operation, the sedimented sample may be removed in a similar fashion by opening a removable lid or cap and using a syringe, pipette or other device to aspirate the final sample from the macrofluidic centrifugation chamber. Likewise a pierceable membrane may be provide on the lid to allow removal of the final sample using a needle and syringe or other aspiration device.

Macrofluidic centrifugation chamber 200 may be pre-filled with a buffer, diluent, detergent or other specially formulated sample pre-treatment solution prior to the introduction of a sample. The sample pre-treatment liquid may be a solution or buffer that contains one or more components or active agents to modify one or more impurities or other components of the sample. For example, the sample pre-treatment solution may act on the sample for the removal, Inactivation, digestion, or other modification of an impurity or other component that may reside within the sample. In another embodiment, the required components are included in the chamber in dried format and these components are dissolved in the liquid sample upon its introduction to the macrofluidic centrifugation chamber.

In other example embodiments, such a pre-treatment liquid may be initially provided in another chamber within integrated fluidic processing cartridge 120, such as in a pre-treatment storage chamber, and where the pre-treatment liquid may be controllably introduced into the macrofluidic centrifugation chamber according to the valving and flow actuation methods described herein.

In a further embodiment the sample pre-treatment solution may be pre-mixed with the sample prior to the introduction of the sample into the cartridge. An example of a sample pre-treatment liquid is a blood lysis liquid, as described in PCT Patent Application No. PCT/CA2013/000992, titled "APPARATUS AND METHOD FOR PRE-TREATMENT OF MICROBIAL SAMPLES", filed on Nov. 26, 2013, which is incorporated herein by reference in its entirety.

In yet another example embodiment, a pre-treatment solution may be introduced into the macrofluidic centrifugation chamber from an external chamber that is fluidically interfaced to the integrated fluidic processing cartridge via a fluidic connector, as described elsewhere herein.

Referring again to FIG. 1, an example implementation of control and processing unit 140 is illustrated. Control and processing unit 140 may include one or more processors 145 (for example, a CPU/microprocessor), bus 142, memory 155, which may include random access memory (RAM) and/or read only memory (ROM), one or more internal storage devices 150 (e.g. a hard disk drive, compact disk drive or internal flash memory), a power supply 180, one more communications interfaces 160, external storage 165, a display 170 and various input/output devices and/or interfaces 175 (e.g., a receiver, a transmitter, a speaker, a display, an output port, a user input device, such as a keyboard, a keypad, a mouse, a position tracked stylus, a position tracked probe, a foot switch, and/or a microphone for capturing speech commands).

Although only one of each component is illustrated in FIG. 1, any number of each component can be included in the control and processing unit 140. For example, a computer typically contains a number of different data storage media. Furthermore, although bus 142 is depicted as a single connection between all of the components, it will be appreciated that the bus 142 may represent one or more circuits, devices or communication channels which link two or more of the components. For example, in personal computers, bus 142 often Includes or is a motherboard.

In one embodiment, control and processing unit 140 may be, or include, a general purpose computer or any other hardware equivalents. Control and processing unit 140 may also be implemented as one or more physical devices that are coupled to processor 145 through one of more communications channels or interfaces. For example, control and processing unit 140 can be implemented using application specific integrated circuits (ASICs). Alternatively, control and processing unit 140 can be implemented as a combination of hardware and software, where the software is loaded into the processor from the memory or over a network connection.

Control and processing unit 140 may be programmed with a set of instructions which when executed in the processor causes the system to perform one or more methods described in the disclosure. Control and processing unit 140 may include many more or less components than those shown.

While some embodiments have been described in the context of fully functioning computers and computer systems, those skilled in the art will appreciate that various embodiments are capable of being distributed as a program product in a variety of forms and are capable of being applied regardless of the particular type of machine or computer readable media used to actually effect the distribution.

A computer readable medium can be used to store software and data which when executed by a data processing system causes the system to perform various methods. The executable software and data can be stored in various places including for example ROM, volatile RAM, non-volatile memory and/or cache. Portions of this software and/or data can be stored in any one of these storage devices. In general, a machine readable medium includes any mechanism that provides (i.e., stores and/or transmits) information in a form accessible by a machine (e.g., a computer, network device, personal digital assistant, manufacturing tool, any device with a set of one or more processors, etc.).

Examples of computer-readable media include but are not limited to recordable and non-recordable type media such as volatile and non-volatile memory devices, read only memory (ROM), random access memory (RAM), flash memory devices, floppy and other removable disks, magnetic disk storage media, optical storage media (e.g., compact discs (CDs), digital versatile disks (DVDs), etc.), among others. The instructions can be embodied in digital and analog communication links for electrical, optical, acoustical or other forms of propagated signals, such as carrier waves, infrared signals, digital signals, and the like.

Some aspects of the present disclosure can be embodied, at least in part, in software. That is, the techniques can be carried out in a computer system or other data processing system in response to its processor, such as a microprocessor, executing sequences of instructions contained in a memory, such as ROM, volatile RAM, non-volatile memory, cache, magnetic and optical disks, or a remote storage device. Further, the instructions can be downloaded into a computing device over a data network in a form of compiled and linked version. Alternatively, the logic to perform the processes as discussed above could be implemented in additional computer and/or machine readable media, such as discrete hardware components as large-scale integrated circuits (LSI's), application-specific integrated circuits (ASIC's), or firmware such as electrically erasable programmable read-only memory (EEPROM's) and field-programmable gate arrays (FPGAs).

Figure 3:
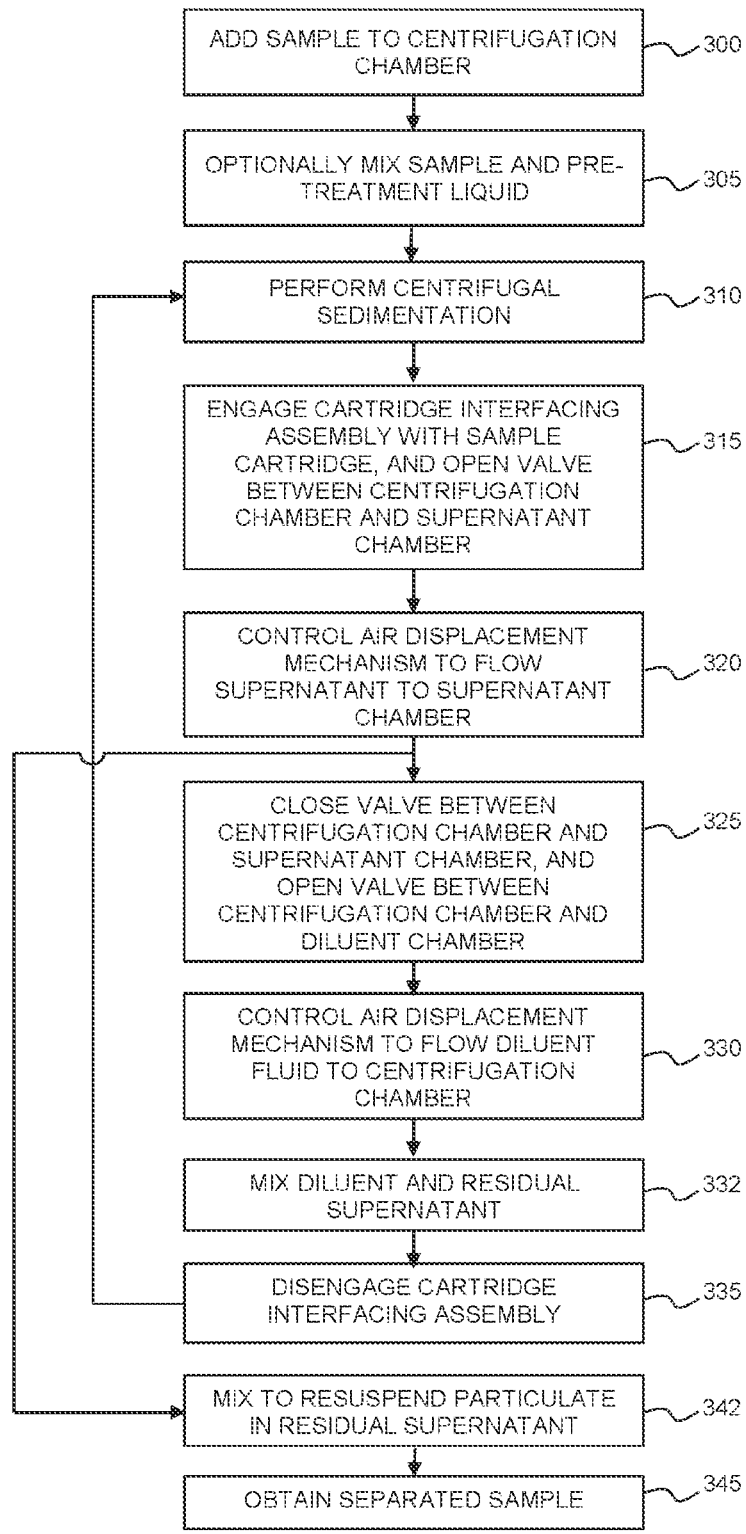
FIG. 3 provides a flow chart illustrating an example method for performing automated centrifugation and washing.

Referring now to FIG. 3, a flow chart is provided that describes an example method of performing automated centrifugal separation and washing of a sample using an integrated fluidic processing cartridge embodiment shown in FIGS. 2A-C. It will be understood that the present example method illustrates but one non-limiting example method, and that a wide variety of other methods may be employed according to the teachings of the present disclosure (for example, methods that do not require valves, as described above, or methods that do not require latching of the valves during centrifugation). According to the present example embodiment, valves 250 and 255 are configured to be latched in a closed configuration when not engaged by a valve actuation mechanism of cartridge interfacing assembly 130. Specific example embodiments describing the operation of such valves are described in detail below.

At 300, sample is initially added to macrofluidic centrifugation chamber 200, according one of various methods described in the present disclosure, such as direct addition through a removable lid or cap in macrofluidic centrifugation chamber 200, or though extraction from a sample chamber that is interfaced with integrated fluidic processing cartridge 120, as described in an example implementation provided below. This operation and subsequent operations not requiring fluid transfer on the cartridge are optionally performed with valves 250 and 255 in a closed state to prevent sample from entering conduits 230 and 240. This closed state of the valves may be achieved by controlling cartridge interfacing assembly 130 such that the valves are actively actuated in a closed state or, if the valves are of the latched closed type, the actuation mechanism places the valves in the latched closed state. After addition of the sample to macrofluidic centrifugation chamber 200, the sample and optionally a pretreatment liquid, the latter of which may be present or introduced into the macrofluidic centrifugation chamber during this step, may optionally be mixed, as shown at 305. Such mixing may be provided by a variety of mechanisms, such as, for example, cyclic or random rotary motion of centrifuge 110, a vibrating mechanism that may be built-into the centrifuge, or capable of removable engagement with centrifuge 110 and/or integrated fluidic processing cartridge 120. This motion may be orbital with an orbital diameter in the range of 1 mm to 10 mm and an orbiting speed in the range of 60 RPM to 2000 RPM for example. The motion may also be non-circular or linear and may be applied only at or near one end of the cartridge or cartridge receptacle which is otherwise supported on a hinge mechanism at or near the opposite end. The mixing may also be performed by an inversion mechanism for cyclically inverting or partially inverting the integrated fluidic processing cartridge. The mixing mechanism may be integrated in cartridge interfacing assembly 130 which is suitably engaged with the cartridge, motorized rotor, or cartridge receptacle included in motorized rotor to impart a cyclic inversion or partial inversion to the integrated fluidic cartridge or cartridge receptacle containing the cartridge. The inversion may be such that centrifugation chamber is oriented with its top surface facing downwards and its axis vertical or positioned at an angle from the vertical axis which is in the range of 0 to 90 degrees from the vertical.

Following the optional mixing, centrifugal sedimentation 310 is performed, whereby integrated fluidic processing cartridge 120 is centrifuged by centrifuge 110 such that the particulate matter (e.g. cells, such as microbial cells) in macrofluidic centrifugation chamber 200 are sedimented. It will be understood that the centrifugation is performed without engagement of cartridge interfacing assembly 130, such that the motorized rotor 114 of the centrifuge 110 may rotate, and such that valves 250 and 255 are latched in a closed configuration.

The rotation speed of motorized rotor 114 that is suitable for sedimentation will depend on a number of parameters associated with the sample that is to be centrifuged. For example, suitable parameters for the centrifugation of microbial cells obtained from a blood sample after lysis of blood cells with the assistance of a sample treatment solution are provided in PCT Patent Application No. PCT/CA2013/000992. Knowledge of the target particulate properties, the suspension fluid solution properties and the rotor geometry can be used by those skilled in the art to determine the appropriate speed and time to effect the desired sedimentation of the particulate. Alternatively the sedimentation speed and time can be determined empirically. In some embodiments sedimentation of all or substantially all of the target particulate in the liquid is desired and sedimentation parameters are selected to enable all such particles to reach the region of the centrifuge chamber beyond the supernatant extraction port 256 or optionally to reach the furthest radial extent in the centrifuge chamber during centrifugation. Alternatively, in the case of samples suspected of containing particulates with different sedimentation coefficients as a result of difference in size or density, it may be desired to retain a portion of the particulate having sedimentation coefficients in a desired range and the sedimentation parameters are selected to enable such a portion of the particulate to enter into the region of the centrifuge chamber beyond the supernatant extraction port 256.

Following centrifugal sedimentation, a portion of the resulting supernatant is extracted. Prior to extraction of the supernatant, motorized rotor 114 is allowed to come to rest, and cartridge interfacing assembly 130 is engaged with integrated fluidic processing cartridge 120 through microfluidic device 205 and valve 255 is opened, as shown at 315. Cartridge interfacing assembly 130 also engages the air displacement device with port 260 and actuates the air displacement device to produce a positive pressure difference between macrofluidic centrifugation chamber 200 and vented supernatant chamber 220, resulting in the extraction of supernatant from macrofluidic centrifugation chamber 200 to supernatant chamber 220 as shown at 320. Thus air displacement induced flow of the supernatant occurs through supernatant extraction port 256 and supernatant delivery channel 240. The volume of supernatant which is thereby removed from the macrofluidic centrifugation chamber 200 may be controlled, at least approximately, by displacing an equivalent volume of air into the macrofluidic centrifugation chamber by the air displacement device. Alternatively air displacement into the macrofluidic centrifugation chamber may be performed until the supernatant level reaches the supernatant extraction port 256 and no further supernatant can be removed. Generally the volume of air which must be displaced in this operation can be predetermined from the known liquid volume in the centrifuge chamber. In the latter case the volume of supernatant removed from the microfluidic centrifugation chamber, or alternatively the volume of supernatant retained in the macrofluidic centrifugation chamber is determined by the location of the supernatant extraction port 256 in the centrifuge chamber.

In example embodiments involving washing and resuspension of the washed sediment, some considerations for the location of supernatant extraction port 256 may be the volume of residual supernatant which is required after each wash or after the final particulate resuspension step 342, and the required wash dilution factor discussed in more detail below. Another consideration for a suitable location of supernatant extraction port 256 is one for which the extraction of the supernatant does not disturb the sedimented particles, for example as a result of hydrodynamic forces resulting from the flow out of supernatant extraction port 256 which may resuspend all or a portion of the sedimented particulate.

Following the supernatant extraction the sedimented particulate matter may be resuspended into the residual fluid by a mixing operation as shown at 342 and collected, as shown at 345 without any wash steps. Collection of the resuspended particles in the residual fluid, herein called the final particulate suspension, may be done by pipette or syringe via an openable cap or pierceable membrane on centrifuge chamber 200. An alternate embodiment is discussed below where an additional opening in centrifuge chamber allows the final particulate suspension to be removed in a similar fashion to the removal of supernatant discussed above.

In some embodiments a wash operation or a sequence of wash operations is required for which a quantity of diluent liquid may be dispensed from diluent chamber 210 to macrofluidic centrifugation chamber 200 as shown at 325. Valve 255 is closed and valve 250 is opened, bringing macrofluidic centrifugation chamber 200 into fluid communication with diluent chamber 210. Diluent liquid is dispensed into macrofluidic centrifugation chamber 200 by engaging the air displacement mechanism connector with port 260, and controllably evacuating air from macrofluidic centrifugation chamber 200, as shown at 330. Thus air displacement induced flow of the diluent liquid occurs through diluent delivery channel 230. The location of the diluent extraction port 251 at which diluent delivery channel 230 enters macrofluidic centrifugation chamber 200 is preferably positioned above the highest extent of the liquid level that is achieved within macrofluidic centrifugation chamber.

Following the dispensing of diluent liquid, cartridge interfacing assembly 130 is optionally engaged as required for the mixing operation, shown at 332, to re-suspend the sedimented particulate matter and mix the residual supernatant with the diluent liquid in macrofluidic centrifugation chamber 200.

Following the optional mixing step, the cartridge interfacing assembly is disengaged as shown at 335 and centrifugal sedimentation is again performed to re-sediment the particulate material, as shown at 310, and the cartridge interfacing assembly is re-engaged with the cartridge as described at 315. After having removed the supernatant as at 320, a wash cycle is deemed to have been performed. If a single wash cycle is required, the sedimented particulate matter may be resuspended into the residual fluid as shown at 342 and collected, as a concentrated suspension, as shown at 345. Alternatively, one or more additional wash cycles may be performed, by repeating 325-335 and 310-320 one or more times. The number of wash cycles required may be determined by performance requirements which may be related to a required dilution factor. The wash cycle dilution factor DF may be calculated from the residual volume ($V_R$) of supernatant remaining in the centrifugal chamber after step 320 of FIG. 3 and the volume of diluent ($V_D$) dispensed into the macrofluidic centrifugation chamber in step 330 according to DF-$(V_D+V_R)/V_R$.

As noted above, the fluidic paths or conduits between the various chambers of integrated fluidic processing cartridge 120 are controllably opened or closed with valves. Although specific examples of valves are shown in many of the examples provided herein, it will be understood that valves may employ any suitable mechanism compatible with the fluid path or port on the device, including, but not limited to pinch valves, ball valves, diaphragm valves, disc valves and plug valves. Examples implementations of specific valves are provided below.

In an alternative embodiment, fluid transfer between chambers of integrated fluidic processing cartridge 120 may be actuated during centrifugation. For example, such an embodiment may be performed employing centrifugally induced pressure to express the supernatant through supernatant extraction port 256 and supernatant delivery channel 240 to the supernatant chamber 220. After a sufficient amount of time, during which centrifugation occurs while valve 255 is open, the supernatant surface, which was initially higher than supernatant extraction port 256, will reach the level of the bottom of supernatant extraction port 256 and supernatant transfer will be complete. The valve 255 may then be closed for subsequent process steps.

Figure 2D:
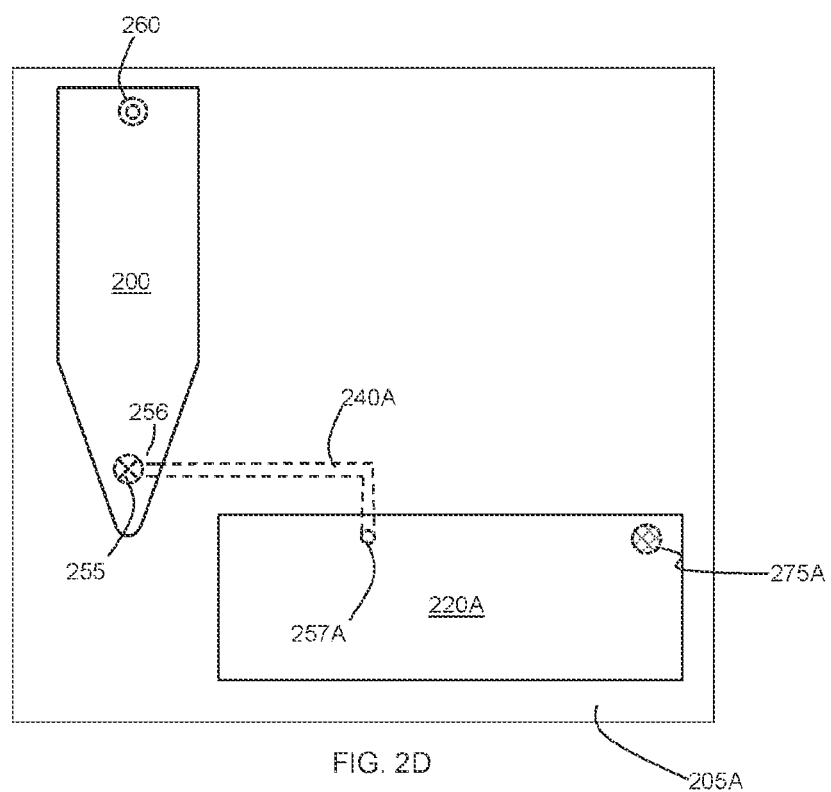
FIG. 2D illustrates an example implementation of an integrated fluidic cartridge that is suitable for performing supernatant extraction during centrifugation.

For this embodiment the supernatant delivery channel 240, supernatant delivery port 257 and the free surface of liquid in supernatant chamber 220 must all have a centrifugal radial position equal to or greater than the final centrifugal radius of the free surface of the supernatant in the macrofluidic centrifugation chamber 200. An example implementation of such an embodiment is illustrated in FIG. 2D, where the supernatant chamber is positioned below the macrofluidic centrifugation chamber 200 such that the supernatant deliver port 257A has a centrifugal radius, during centrifugation, that is greater than the supernatant extraction port 256. This embodiment may be beneficial in that the sedimented particles will be held firmly by centrifugal force during extraction of the supernatant and there is less risk of disturbing the sediment by hydrodynamic forces produced by the exiting supernatant flow. This may allow supernatant extraction port 256 to be placed lower within macrofluidic centrifugation chamber 200 than is the case when the supernatant is removed, as described previously, while the motorized rotor 114 is at rest. A lower position of the supernatant extraction port 256 will produce a lower residual supernatant volume and a high wash efficiency and a highly concentrated suspension may also be achieved.

In such an embodiment, valve 255 is controllably actuated during centrifugation. Such controllable actuation may be achieved electromagnetically, through the use of electromagnet actuators housed within motorized rotor 114 that are externally connected to a controller (e.g. control and processing unit 140, or an electrical controller that is interfaced with control and processing unit 140), via a rotary interfacing mechanism such as a slip ring. In other embodiments, the valves may be actuated during centrifugation via a pneumatic actuation mechanism residing on centrifuge 110, where the pneumatic actuation mechanism is interfaced with an external pneumatic pressure source via a fluid rotary joint.

In another example implementation, the integrated fluidic cartridge received within the receptacle with a mechanism that permits the application of pressure differential between chambers during centrifugation, without requiring the motorized rotor to come to rest. Such an embodiment may be beneficial in reducing overall processing times by avoiding the time involved in stopping the motorized rotor and aligning the integrated fluidic cartridge with the cartridge interfacing assembly, and for avoiding the need to align the cartridge interfacing unit with the integrated fluidic cartridge. The motorized rotor may be controlled to reduce its rotation speed during the application of a pressure differential between chambers (and during actuation of valves), in order to reduce centrifugal forces within the channels. It will be understood that other non-fluidic components, such as an optical detection system, may additionally or alternatively integrated with the motorized rotor.

For example, a pump mechanism may be integrated with the motorized rotor or the receptacle, and wherein the pump is electrically interfaced with an external controller (for example, through an electrical slip ring), such that the pump can be actuated and controlled during rotation of the motorized rotor. The pump should be constructed and oriented to withstand the centrifugal forces during rotation at high speeds. Alternatively, an external air displacement pump mechanism may be employed that is interfaced with the cartridge via a fluid rotary joint (where the air optionally includes one or more valves).

Figure 4A:
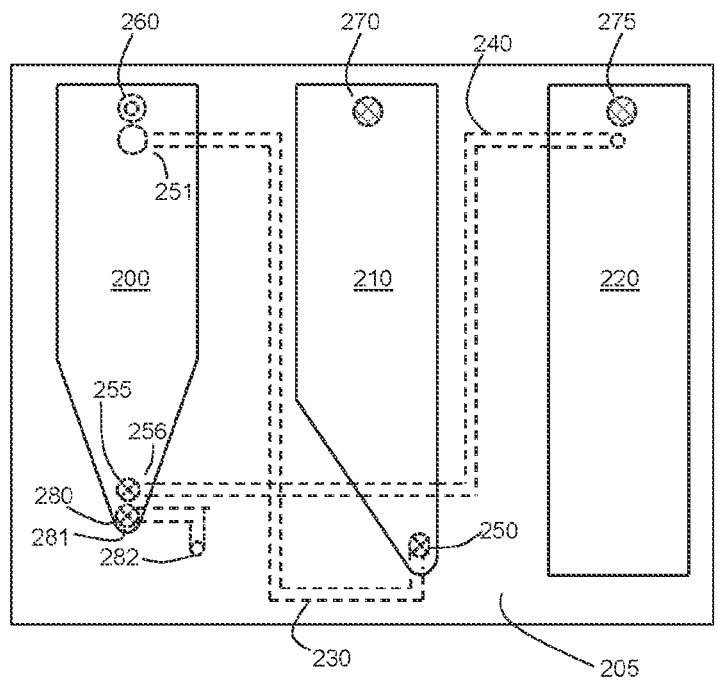
FIGS. 4A and 4B provide front views of an embodiment of an example integrated fluidic processing cartridge including a port for extraction of the sedimented particles, or a suspension thereof.
Figure 4B:
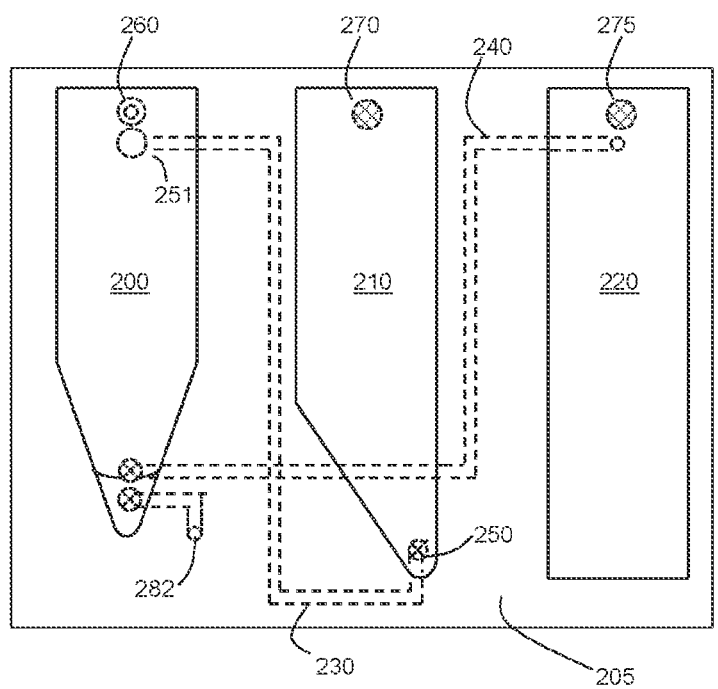

FIGS. 4A and 4B illustrate an example embodiment in which an additional fluidic path is provided for transferring the final particle (e.g. cells) suspension to the microfluidic device for further processing following centrifugal separation and washing. In FIG. 4A, a sediment extraction channel 282 is provided that connects the sediment extraction port 281, which resides in the distal region of the macrofluidic centrifugation chamber 200 (e.g. at the bottom of the macrofluidic centrifugation chamber, or at another location associated with the sedimentation of the sediment within the distal region) with the microfluidic device, and is controlled via sediment extraction control valve 280. Sediment extraction channel 282 may lead, for example, to a storage chamber in the microfluidic device for subsequent collection or processing or to an exit port designed for collecting the sample by an external means.

Alternatively, shown in FIG. 4B, the sediment extraction port 281 resides within macrofluidic centrifugation chamber 200 at some height offset above the bottom of the macrofluidic centrifugation chamber and below the supernatant extraction port 256. This example embodiment allows for the removal of the top portion of the final particle suspension.

In one example implementation, the sediment may include more than one type of particle, and a first subset of particles may have a larger size than a second subset of particles. In some applications, it may be desirable to separate (at least a portion of) the second set of particles from the first set of particles. The suspension obtained after the resuspension step 342 may be centrifuged for a predetermined length of time at a predetermined speed such that the first set of particles, having the higher sedimentation rate, move to a position below the sediment extraction port 281, such that a particle suspension free of these particles may be removed at sediment extraction port 281.

Additional openings, valves and fluidic conduits may be introduced between the distal region of the centrifuge chamber and the supernatant extraction port 256 such that a sequence of extractions through these openings from the uppermost to the lowest can be performed to obtain a series of particle suspensions from each respective level of the final particle suspension, optionally allowing the extraction and optional collection of fractionated suspensions. Optionally, following the final particle resuspension step 342, a controlled centrifugation step may be performed which the sequence of extractions from uppermost to lowest openings would yield a series of particle suspensions which contain particles with increasing particle sedimentation rates.

In another embodiment the sediment extraction port 281 may be positioned just above the meniscus of a cushioning liquid that is configured to retain separated particles, such as microbial cells. This embodiment is discussed in more detail below, with reference to FIG. 5.

Although many of the example embodiments described herein employ an integrated fluidic processing cartridge that includes a supernatant chamber and a dilution chamber, it will be understood that other example embodiments, the integrated fluidic processing cartridge may be absent of one or more of such chambers. For example, the integrated fluidic cartridge may include a macrofluidic centrifugation chamber that is interfaced, through a lateral surface thereof, with the microfluidic device, in the absence of the supernatant chamber and the diluent chamber. Such a device may be employed to perform centrifugal separation of a sample, and the extract a sediment into the microfluidic device, optionally for further fluidic processing therein. In another example embodiment, the integrated fluidic processing cartridge may include a macrofluidic centrifugation chamber that is fluidically interfaced, through the microfluidic device, to a supernatant chamber, for the separation of the supernatant from the sediment after centrifugation, in the absence of a diluent chamber. Such an embodiment may be useful in applications in which it is the supernatant that is the component of interest for further fluidic processing. In such an embodiment, the supernatant chamber may be fluidically interfaced, through a port provided therein, to the microfluidic device, for extraction of the supernatant into the microfluidic device and optional additional fluidic processing therein.

In some embodiments, integrated fluidic processing cartridge 120 may include one or more integrated sensors for detecting liquid levels, pressure and/or liquid flow, during operation. Such embodiments may be useful in verifying system performance as internal process controls. In one example implementation, one or more electrodes may be placed within any one or more of the various chambers present within integrated fluidic processing cartridge 120. For example, a plurality of electrodes may be placed at different locations along the long axis of macrofluidic centrifugation chamber 200, and the electrodes may be interrogated relative to a reference electrode or reference voltage in order to determine whether or not a given electrode is in contact with liquid, thereby enabling the detection of discrete liquid levels within the chamber. One or more electrodes may be located at locations such as, for example, above a meniscus level associated with the residual liquid that is retained after extraction of the supernatant through supernatant extraction port 256. An electrode may also be located adjacent to, or immediately below, port 260, in order to provide an indication as to whether or not port 260 is contaminated with liquid. An electrode may be located at a desired level in the macrofluidic centrifugation chamber 200 indicating that a sufficient amount of sample and/or diluent is present. A reference electrode may be placed sufficiently low in the macrofluidic centrifugation chamber such that the reference electrode is always submerged in the residual fluid in the macrofluidic centrifugation chamber and such that the above levels may be detected by continuity or resistance measurement between the various electrodes and the reference electrode.

The sensed electrical signal may be monitored during fluid transfer when the cartridge interfacing assembly 130 is engaged with the cartridge 120 or receptacle 112. The electrical signal may also be monitored during centrifugation according to any one of a variety of transduction methods and mechanisms, such as, for example, an optical transponder that rotates with motorized rotor 114 and transmits (and optionally receives) optical signals to (and optionally from) a fixed transponder that does not rotate, a pair of wireless transceivers (one of which rotates with motorized rotor 114), or an electrical connection to control and processing unit 140 through an electrical slip ring. Impedance measurements may be performed in order to measure or characterize one or more aspects of the liquid within a given chamber, for example, to verify hemolysis of blood cells within macrofluidic centrifugation chamber 200. Additionally or alternatively, one or more pressure sensors may be provided within integrated fluidic processing cartridge 120, in order to dynamically interrogate the pressure within integrated fluidic processing cartridge 120 during rotation of motorized centrifuge.

In other example implementations, liquid level sensing may be achieved using an external imaging camera that obtains images of the integrated fluidic processing cartridge during rotation (using a camera with a sufficiently fast frame rate), where the imaging camera is optionally synchronized to periodically obtain frames when integrated fluidic processing cartridge 120 is in a given angular position (optionally obtaining one image per n rotations, where n>1), thereby enabling dynamic tracking of liquid levels and liquid transport. In order to achieve imaging with sufficient clarity, it may be beneficial to temporarily reduce the rotation rate of the rotor. In other example embodiments, liquid levels may be obtained by directing one or more light beams (e.g. focused or collimated laser beams) onto the cartridge, and monitoring the reflected signal to determine when the beam encounters a liquid within the integrated fluidic processing cartridge. Such a beam may optionally be scanned in order to sample various regions of the integrated fluidic processing cartridge for liquid level detection.

The aforementioned liquid level sensing example embodiments may also be useful for monitoring the transfer of supernatant or other fluids during centrifugation according to the above-mentioned example embodiments, and the sensed liquid levels may be employed to control the closure of the valves and/or the application of a pressure differential between chambers.

With reference to the example schematic representation in FIG. 5, an example integrated fluidic processing cartridge 500 is portrayed which incorporates elements suitable for automated separation and washing of particles in a liquid to obtain a concentrated suspension, for example, in accordance with the methods disclosed in PCT Patent Application No. PCT/CA2013/000992. The example integrated fluidic processing cartridge includes a sample transfer receptacle 501, a macrofluidic centrifugation chamber 502, a diluent chamber 504 and a supernatant chamber 506. Diluent chamber 504 is prefilled with a wash buffer fluid 505, is fluidically connected to macrofluidic centrifugation chamber 502 via conduit 510 equipped with shutoff valve 512, contains a vent to atmosphere 515 and is otherwise closed. Supernatant chamber 506 is fluidically connected to macrofluidic centrifugation chamber 502 via a conduit 511 equipped with shutoff valve 513, contains a vent to atmosphere 516 and is otherwise closed. Macrofluidic centrifugation chamber 502 has a conical or round bottom shape and a smooth inner surface which minimizes adsorption or trapping of particles (e.g. microbial cells) during centrifugation and is closed with the exception of the openings 522, 523, 524, 525, 526 to respective conduits.

In some example embodiments, macrofluidic centrifugation chamber may be employed for the processing of blood-containing samples (e.g. whole blood, blood culture samples, or other blood-containing samples). In such embodiments, macrofluidic centrifugation chamber may contain a pretreatment fluid 503 which may include agents for lysis of blood cells and a cushioning fluid 529 to aid in microbial cell recovery and to minimize compaction injury of the cells which may compromise the integrity and recovery of the target nucleic acids.

The cushioning fluid is of higher density than the remainder of the fluid and is water immiscible such that it settles to the bottom of macrofluidic centrifugation chamber under gravity and centrifugal forces. The sample transfer receptacle is equipped with a needle 507 which is mounted at the bottom of the receptacle. The needle is connected to a fluid path 508 equipped with a shut-off valve 509 which leads to macrofluidic centrifugation chamber 502. A sample tube or container 520 with a pierceable cap 521, such as, for example a Vacutainer® blood collection tube or a blood culture tube containing a blood sample and growth media, may be inserted into the sample transfer receptacle such that the needle 507 pierces the cap 521 thus allowing transfer of a sample fluid to the cartridge via the needle and fluidic path 508. Optionally needle 507 is covered with a pierceable hood 508 which protects the needle from contamination.

The example integrated fluidic processing cartridge 500 is a closed cartridge (apart from the vents described below) which, following the insertion of the sample, performs all the functions required for separation and washing of a concentrated suspension within the chambers and conduits of the cartridge, has all reagents and solutions stored in chambers on the cartridge, and retains all excess liquids including waste supernatant in chambers on the cartridge. One or more of the vents and ports may be protected by air permeable membranes with a pore size sufficiently small to prevent the ingress of microbial pathogens in the target range of the device. According to the present example embodiment, all excess and waste liquids are stored on the cartridge and are not exposed to the user. Thus the closed cartridge provides a device which protect the user from direct contact with the sample and for which the sample is not susceptible to contamination by external factors during the separation and washing process.

As noted above, an automated separation and washing process is generally described in FIG. 3. The cartridge is inserted into an instrument equipped with the necessary devices and functionality, including a cartridge interfacing assembly, as described generally in FIG. 1. The cartridge interfacing assembly is equipped with all the components required to perform the necessary actions including actuation of the cartridge valves 509, 512, 513, and 517 and an air displacement device capable of application of both positive and negative gauge pressure to the cartridge centrifuge chamber via cartridge port 518.

The sample tube 520 containing a sample is inserted into the sample transfer receptacle 501 of cartridge 500 thus piercing the tube cap 521 to perform the sample transfer to the macrofluidic centrifugation chamber as shown at 300 of FIG. 3. The cartridge interface assembly engages with the cartridge via a cartridge receptacle, described in detail below, and is actuated such that valve 509 is open and valves 512, 513 and 517 are closed, thus sealing all fluid paths emanating from macrofluidic centrifugation chamber except the path 508 from the sample tube.

The air displacement device is engaged with the port 518 by way of a connector which provides a sealed connection with the port. Optionally a rigid or flexible tube connects the air displacement device to the connector. Sample transfer to macrofluidic centrifugation chamber 502 is performed by operating the air displacement device to extract air from macrofluidic centrifugation chamber to cause sample flow from the sample tube 520 into macrofluidic centrifugation chamber 502 via fluid path 508. The entry 523 of the port 518 must be positioned above the fluid level and with a sufficient air gap between the fluid level and the entry 523 such that no fluid flows into entry 523 to the port 518. The air displacement activated flow is done in a controlled manner such that a predetermined volume of sample is transferred into macrofluidic centrifugation chamber.

In one embodiment the entry 522 to flow path 508 is also in the air gap above the fluid level such that, following transfer of the desired volume of sample, the air displacement via port 518 can be reversed to provide a small amount of air displacement into macrofluidic centrifugation chamber to clear the flow path 508 of sample fluid and move this residual sample back into the sample tube 520. Then the valve 509 is closed and the sample tube 520 is optionally removed from the receptacle 501.

As noted above, a sample pretreatment fluid may be present in the chamber prior to the sample transfer process or alternatively it may be transferred from a pretreatment fluid tube in a similar manner as the sample. Alternatively a pretreatment fluid storage chamber may be provided on the cartridge and a fluidic path with valve and an air vent may be provided to allow the pretreatment fluid to be moved to macrofluidic centrifugation chamber in a similar manner to the movement of wash buffer to macrofluidic centrifugation chamber as described below.

After addition of the sample to macrofluidic centrifugation chamber 502, the sample and the pretreatment liquid may optionally be mixed as at 305 of FIG. 3. A mixing mechanism may be provided whereby the instrument performs vortexing, shaking, or cyclic inversion of the cartridge. This operation is done with valves closed on all fluid paths emanating from macrofluidic centrifugation chamber 502. A valve may be provided on the fluid path to the port 518 to prevent fluid from entering the air path during mixing. In addition, or alternatively, an air permeable membrane which prevents the passage of fluid may be placed in the air path between macrofluidic centrifugation chamber and the port 518 to prevent fluid from reaching the port 518. This membrane may also be configured to serve as an air filter to prevent the ingress of microbes from the environment or from the air displacement device. Alternatively the path between the port 518 and the entry opening 523 to macrofluidic centrifugation chamber can be designed to possess high fluidic resistance such that under the prevailing conditions fluid will be prevented from entering the opening 523 or will be prevented from proceeding all the way to the port 518. Likewise vents 515 and 516 in diluent chamber 505 and supernatant chamber 506 respectively may be equipped with an air permeable membrane and/or a path with high fluidic resistance to serve a similar purpose.

Following the mixing step 305 a centrifugal sedimentation step 310 is performed whereby the cartridge interfacing assembly is disengaged from the motorized rotor 114 and the cartridge 120 is centrifuged such that the particles (e.g. microbial cells) in macrofluidic centrifugation chamber sediment on the cushioning liquid, for example, as per the methods of PCT Patent Application No. PCT/CA2013/000992. The centrifuge may be an angle centrifuge or a hanging bucket centrifuge and the centrifugal parameters may be selected according to the conditions provided in PCT Patent Application No. PCT/CA2013/000992.

The relative centrifugal force applied to the fluids within the macrofluidic centrifugation vessel may be, for example, within the range of 1000-15,000 g, or for example, 2,000-12,000 g, or, for example, 3000-10,000 g, or, for example, 3000-7,000 g. or, for example, 5000-10,000 g, or, for example, 4000-8,000 g. In applications involving separation of bacterial and fungal cells from biological samples, it has been found that a suitable relative centrifugal force (RCF) is within the range of 1000 g-15000 g range, and more specifically, within the range of 3000 g-7000 g.

Following the centrifugal sedimentation step 310 of FIG. 3, the centrifuge rotor is stopped and the cartridge interfacing assembly is re-engaged with the motorized rotor as at 315 and extraction of the supernatant 527 from macrofluidic centrifugation chamber to the supernatant chamber 506 is performed as at 320 whereby the residual 528 containing the target sediment (e.g. microbial cells) is retained at the bottom of macrofluidic centrifugation chamber 502. This action is performed by opening valve 513 while valves 509, 512 and 517 remain closed and engaging the air displacement device connector with port 518 and controllably displacing air into macrofluidic centrifugation chamber. Thus air displacement induced flow of the supernatant occurs through fluid path 511, the entry 524 of which is placed below the lowest extent of the supernatant. Optionally the entry 524 is placed at the lowest extent of the supernatant which is to be expressed from macrofluidic centrifugation chamber, thus preventing residual 528 from being extracted from macrofluidic centrifugation chamber.

Following the supernatant extraction step 320, the wash buffer dispensing steps 325 and 330 are performed whereby wash buffer is dispensed into macrofluidic centrifugation chamber 502. This action is performed by opening valve 512 while holding valves 509, 513 and 517 closed and engaging the air displacement device connector with port 518 and controllably evacuating air from macrofluidic centrifugation chamber 502. Thus air displacement induced flow of the wash buffer occurs through fluid path 510. The entry 525 of wash buffer path 510 is preferably placed above the highest extent of the fluid level in macrofluidic centrifugation chamber.

Following the wash buffer dispensing step 544, the mixing step 332 is performed to thoroughly mix the wash buffer and the residual fluid in macrofluidic centrifugation chamber. This may be performed by vortexing, shaking, or cyclic inversion of the cartridge as described previously.

Following the mixing step 332, the centrifugal sedimentation step 310 is performed to re-sediment the collected sediment (e.g. microbial cells) and the supernatant is removed from the centrifugal chamber as in step 320.

The sequence of steps 325-335 and 310-320 collectively form a wash cycle whereby the cell suspension is diluted in wash buffer, the particles are re-sedimented and the supernatant is extracted. The wash cycle may be repeated multiple times to effect multiple additional wash cycles as required to obtain a final suspension sufficiently dilute (e.g. a microbial cell suspension that is sufficiently dilute of contaminants and interferants). The desired dilution factor depends on the sample composition and downstream detection procedure. In one embodiment, intended for applications involving separation of bacterial and fungal cells from biological samples, electrical lysis of microbial cells and detection through RT-PCR amplification of ribosomal RNA, the dilution factor is selected in 100-100000 range. More preferred range is 1000-50000. In another embodiment involving separation of bacterial and fungal cells from blood samples, lysis of microbial cells and detection through PCR amplification of DNA, the dilution factor can be as small as 1 provided that inhibitor-resistant polymerase enzyme along with an appropriate amplicon detection scheme is employed. Exemplary implementation of DNA amplification and detection method in whole blood is reported in prior art (e.g., L. A. Neely et al., Science translational medicine5.182 (2013): 182ra54-182ra54.).

Following the final supernatant extraction step 320 the mixing step 342 is performed to resuspend the sedimented particles (e.g. microbial cells) in the final residual fluid 528 to produce the final suspension.

Following the resuspension step 342 the final suspension is extracted by air displacement through fluid path 510. The volume of the final suspension depends on the nature of the application. For instance, when the intended application is the detection of pathogenic microbial cells in whole or cultured blood, the volume of the final cell suspension may be selected to be in 10 μL-500 μL range. More preferred range is 20 μL-120 μL, or 50-100 μL. During the extraction of the final cell suspension valve 517 is open and valves 509, 512 and 513 are closed and air is displaced through port 518 into macrofluidic centrifugation chamber to displace the fluid out of opening 526 via fluid path 516. The opening 526 is so positioned at the top surface of the cushioning fluid 529 that the final suspension in its entirety, or substantially all of the suspension, is expressed from macrofluidic centrifugation chamber without expressing any of the cushioning fluid 529 as depicted in FIG. 5. Alternatively, the opening 526 is so positioned that the final suspension and portion of or all of the cushioning fluid may be expressed from the macrofluidic centrifugation chamber through fluid path 516. Fluid path 516 leads to the next downstream cartridge element which in some embodiments may be a chamber or chamber configured to allow retrieval of the final suspension from the cartridge for further processing outside of the cartridge, and in other embodiments this may be a fluid path to a suspension collection chamber, or for example, an electrical lysis chamber as described below.

Integration of Centrifugation-Based Integrated Fluidic Processing Cartridge with Additional Fluidic Processing Elements As described below, in various example embodiments of the present disclosure, the microfluidic device of integrated fluidic processing cartridge 120 can be supplemented with various additional fluidic components, chambers, and features in order to support further processing of the final residual suspension (or the supernatant, if desired).

In one example embodiment in which cells are present in the final residual suspension, after having extracted the supernatant, are resuspended. Then, the cell content of the resulting cell suspension may be transferred to the microfluidic device, as described above, through the sediment extraction port. The cell suspension may then be interrogated according to any of a wide range of cell assays. In one example embodiment, the resulting cell suspension may be delivered to a planar channel or chamber formed at least in part by a transparent optical window. Cells retained in the planar channel or chamber may be optically interrogated.

For example, the retained cells may be enumerated and/or inspected an optical imaging system equipped with a microscopic objective. The objective may be mounted on moving mechanism to scan the volume of the chamber.

In one example embodiment, the cells are located in a zone which is located in the field of view of the microscope objective. For example, the cells may be retained on a planar substrate coated with a material suitable for adhering cells, such as a cell-specific or cell-generic coating. The cells may also be driven to a focal zone via electric fields, such as via dielectrophoresis.

Figure 6:
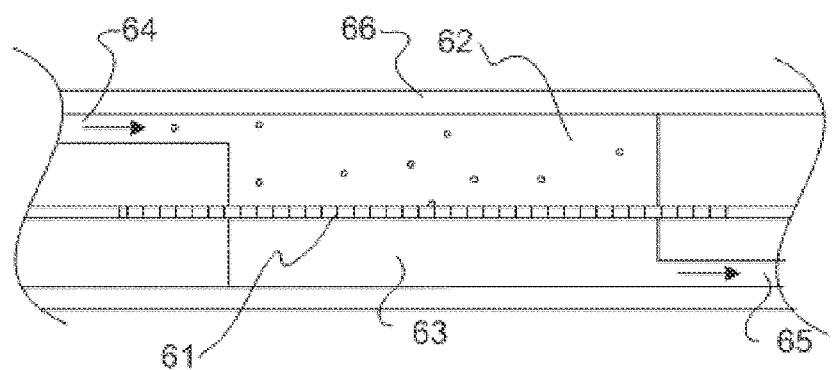
FIG. 6 shows schematic cross-sectional views of a channel which has been equipped with a filter intended for retaining cells.

In order to enable interrogation of low cell counts, the cells may be retained on the surface of a filter housed within the microfluidic device. This eliminates or relaxes the requirement for scanning along the axis of the objective. An example embodiment in which the cells are retained on filter for microscopic inspection is presented in FIG. 6. A filter 61, for example a membrane filter, having a thickness less than that of the chamber, is secured within a channel of the microfluidic device (where the channel is in fluid communication with the sediment extraction channel for delivery of the concentration suspension thereto), such that the channel is divided into two portions 62 and 63, thereby enabling cells within the sample to be retained by the filter as the concentrated suspension is flowed between the inlet port 64 and outlet port 65. In one example implementation, the filter may be made of material, such as high density polyethylene, or polycarbonate membrane. The upper part of the channel, 66 in FIG. 6, is made of thin transparent films to allow passage of light to the objective.

The microscopic examination of microbial cells, as explained above, may be used for performing antibiotic susceptibility testing (AST), particularly in the case of non-enriched samples for which the microbial cell count in the sample is low. According to one example implementation, the biological sample is first tested for the presence and identity of the pathogenic microbial cells using the methods described in the present disclosure or any other suitable method. This determination narrows down the selection of appropriate antibiotic agent to one or few candidates, often by referring to the antibiogram of the associated healthcare setting.

The AST is initiated by incubating two aliquots of the sample both supplemented with appropriate medium that sufficiently supports the growth of the microbial cells under suitable temperature conditions provided by an incubation instrument. The antibiotic agent is added to one of the aliquots and the other aliquot is treated as control sample. After the passage of a predetermined incubation period, the two aliquots are processed within the microfluidic device portion. Thus relatively clean cell suspensions are prepared for each aliquot. Then the cells are microscopically inspected by retaining in filtered chambers as described above to verify if the cells exposed to the antibiotic agent have been killed (the case of cidal antimicrobial agents) or have been inhibited in terms of growth (the case of static antimicrobial agents). Thereby, the AST result is determined. Accordingly, the present example embodiments may enables the extending the methods of AST recited in US Patent Application Publication No. 2013/0217063 to the case of samples having scarce microbial count (for example, in the range of 1 to 100,000 CFU/ml). It will be understood that the aliquots may be sample aliquots that are processed on separate integrated cartridges, or the aliquots may be aliquots of the concentrated suspension that is obtained after automated centrifugation, thus permitting the aliquots to be split and subsequently processed within the microfluidic device portion of a single integrated fluidic cartridge.

In some embodiments, the amount of dilution achieved during fluidic processing, prior to delivering the concentrated suspension to the microfluidic device, may be selected to be sufficiently high such that the suspended cells can be retained on the filter without causing filer clogging. A suitable dilution level (or washing level) may be determined based on the composition of the biological sample, the nature of pretreatment of the sample prior to dilution, and the area of the filter.

This may be illustrated, for example, by referring to a specific example where the target microbial cells are in whole blood. For instance, US Patent Application 2013/0171615 teaches lysing blood cells using equal volume of 1M NaCarbonate pH 10.0+1% Triton X-100. According to the presented data 2.5 mL of treated blood can be passed through a membrane filter with diameter of 2.5 cm and pore sizes of 0.45 µm without significant clogging. Accordingly, only $2.5 \times (0.4/25)^2$ mL-0.6 µL of unwashed lysed blood sample can be passed through a filter having a diameter of 0.4 mm, which approximately corresponds to the field of view of a 40× microscopic objective. However, a washing procedure providing a dilution of blood debris by 100× will enable filtering of 60 µL cell suspension from pretreatment step. The cell content of the suspension may undergo additional fluidic processing prior to microscopic inspection. These additional processing steps may include, for example, exposure to drugs or other chemical agents for a predetermined period, staining with fluorescent dyes, or incubation with appropriate FISH (Fluorescence in situ hybridization) reagents, and addition of cell growth media and optional incubation therein. The manipulation can be performed prior to filtering and after retaining the cells on the filter.

In an alternative example implementation, the concentrated cell suspension, extracted to the microfluidic device, and optionally filtered therein as described above, may be mixed with a matrix assisted laser desorption/ionization (MALDI) matrix material and subsequently fluidically delivered to a chamber from which a MALDI sample may be extracted for performing MALDI analysis. In one example embodiment, the microfluidic device may be configured to deliver the mixture to a one or more wells that are formed on a substrate suitable for MALDI (e.g. a metal substrate) such that the microfluidic device provides one or more MALDI-ready samples. The MALDI substrate may then be removed from the microfluidic device and processed according to known MALDI methods. Alternatively, the wells formed on the MALDI substrate may open wells, or may be exposed by removing of one or more peelable or otherwise removable layers of the microfluidic device.

The non-limiting example embodiments described below pertain to an example integrated fluidic processing cartridge in which the microfluidic device includes components for the lysis of microbial cells extracted according to the aforementioned embodiments, and assay chambers for performing molecular detection of nucleic acids present in the lysate.

It will be understood that although many of the example embodiments provided herein relate to the purification and concentration of cells in a suspension, the methods, systems, and devices described herein may be adapted to a wide variety of associated embodiments. For example, in some example implementations, the supernatant can be extracted and transferred to the microfluidic device for further fluidic processing, such as the performing of one or more integrated assays. Such an embodiment would not involve a washing step. In other embodiments, both the supernatant, and a residual sample may be obtained, and one or both may be transferred to the microfluidic device for further processing. In other embodiments, a fluid, such as a suspension, that is initially transferred to the microfluidic device for processing, may be subsequently transferred back to the macrofluidic centrifugation chamber for further centrifugation.

In the embodiments described a sample, such as a whole blood sample, is inserted into a cartridge and a series of operations are performed on the cartridge by a dedicated instrument to perform the functions summarized in FIG. 7A-D.

Figure 7A:
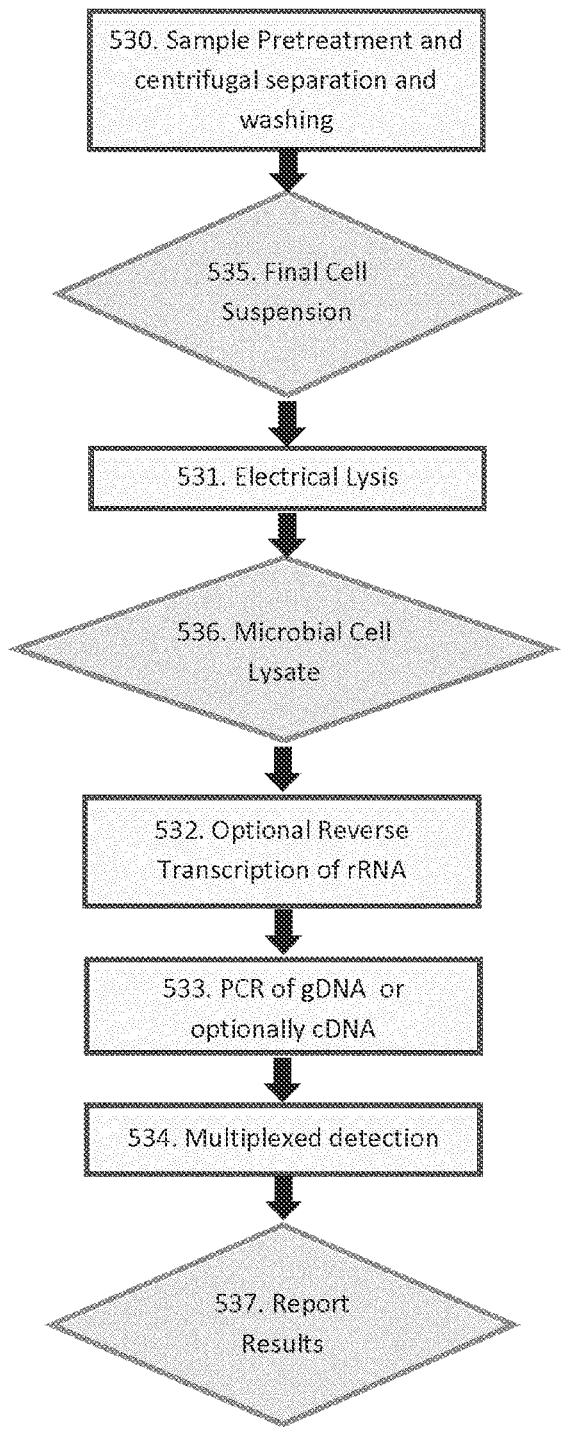
FIG. 7A is a flow chart describing a method of sample preparation, electrical lysis, and multiplexed molecular detection of nucleic acids present in the lysate, according to one example embodiment of the present disclosure.
Figure 7B:
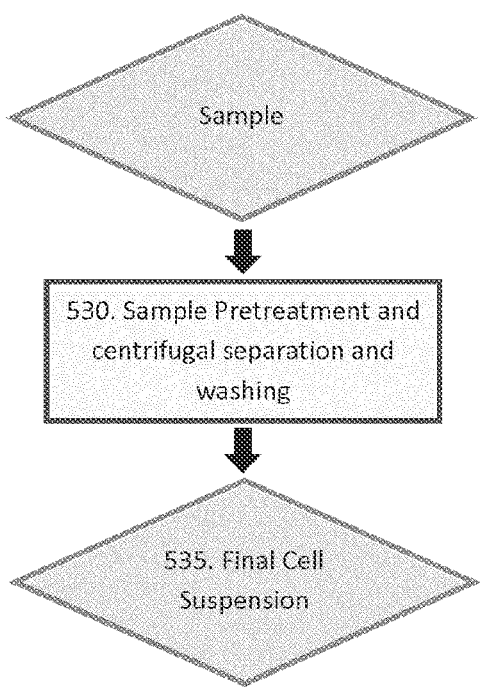
FIG. 7B is a flow chart describing a method of sample preparation according to one example embodiment of the present disclosure.

Thus, as depicted in FIG. 7A, the sample, containing target cells of interest, undergoes the automated separation and washing process 530 followed by electrical lysis and treatment 531 and then reverse transcription 532 of rRNA which is followed by PCR amplification 533 of the cDNA (and/or optionally gDNA) and multiplexed detection 534 of the target amplified nucleic acids. The instrument then analyses the detected signals and reports the results to the user 537. Pretreatment of a sample is performed by initial selective lysis of non-microbial cells (such as blood cells) and subsequent centrifugal separation and optional wash cycles, as presented generally in FIG. 3, to concentrate the cells and remove the blood debris. The microbial cells are subsequently resuspended and the resulting microbial cell suspension 535 is herein termed the "final cell suspension". The final cell suspension is passed to an electrical lysis chamber where the microbial cells are lysed such that target nucleic acids are released and electrically treated. The resulting microbial cell lysate 536 is then passed to a thermal chamber or a plurality of thermal chambers where reverse transcription, PCR and detection of PCR products is performed as required for detection of target microbes. The cartridge provided in some embodiments described herein integrates the totality of this process where a sample, such as a whole blood sample, is introduced to the cartridge and all elements required for sample pretreatment, centrifugal separation and washing, microbial cell lysis, reverse transcription, PCR and detection of target PCR products are present in the cartridge which, in conjunction with a dedicated instrument, performs the full process culminating in the detection and optionally the identification of the target microbes.

Alternative example embodiments may integrate a part of this process. For example, a cartridge incorporating all elements required for the pre-treatment and centrifugal separation and washing process 530 results in a final cell suspension 535 which can be retrieved from the cartridge and processed externally from the cartridge as in FIG. 7B.

Figure 7C:
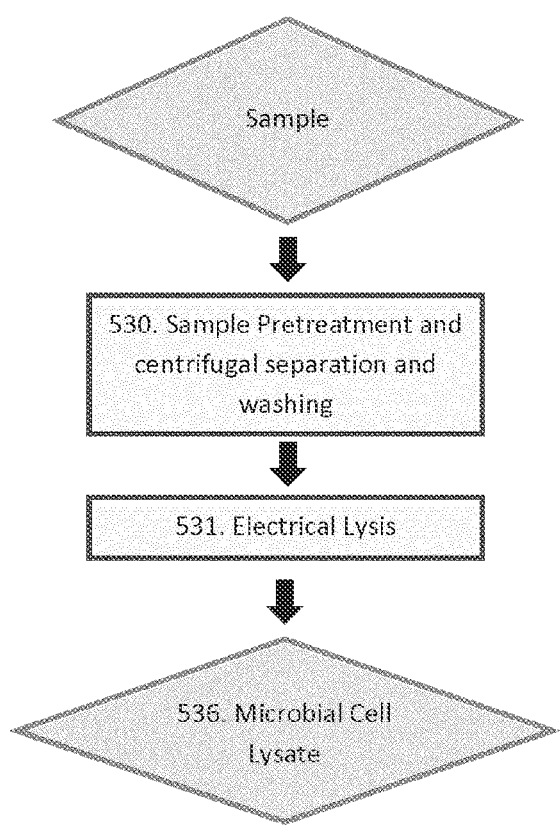
FIG. 7C is a flow chart describing a method of sample preparation and electrical lysis according to one example embodiment of the present disclosure.

In another example embodiment, the cartridge integrates the sample pre-treatment, separation and washing process 530 and microbial cell electrical lysis and treatment 531, yielding a lysate solution 536 which can be retrieved from the cartridge and processed externally as shown in FIG. 7C.

As noted above, integrated fluidic processing cartridge 120 is insertable into a receptacle supported by a motorized rotor appropriate for centrifugation, and the integrated fluidic processing cartridge may incorporate one or more fluidic features (e.g. fluidic valves) such as valves for opening and dosing ports and fluid paths, vents, and ports to allow connection to an air displacement device for air displacement induced fluidic movements. Valves may employ any suitable mechanism compatible with the fluid path or port on the device, including, but not limited to punch valves, ball valves, diaphragm valves, disc valves and plug valves. Valves may be employed to control and/or direct fluidic movements, to control evaporation of fluids during electrical lysing and treatment and/or PCR cycling, and to allow superheating to occur in the electrical lysing and treatment chamber as described in United States Patent Application Publication No. 2014/0004501.

Although the preceding example embodiments relate to the processing of whole blood as a sample matrix, it is to be understood that the methods and devices disclosed herein may be adapted to a wide variety of specimens. Suitable specimens include, but are not limited to urine, sputum, cerebral spinal fluid, swabbed tissue samples, vaginal samples, and other sample types of biological origin, and non-biological samples that may contain microbial cells. A sample may be provided by processing a solid or partially solid sample in order to produce a liquid sample (e.g. using a process such as homogenization). Examples of other sample types include other liquid samples that may contain microbial cells, such as environmental water samples, liquid food samples, and homogenized food samples. The initial sample may be combined with a reagent, buffer, or other medium prior to introduction into the integrated fluidic processing cartridge.

Furthermore, although the preceding example embodiments relate to the amplification and detection of nucleic acids, it is to be understood that the methods and devices disclosed herein may be adapted to other applications and assays. For example, the lysate may be used to detect cellular proteins, or the lysate may be retrieved from the cartridge for such purposes.

Figure 7D:
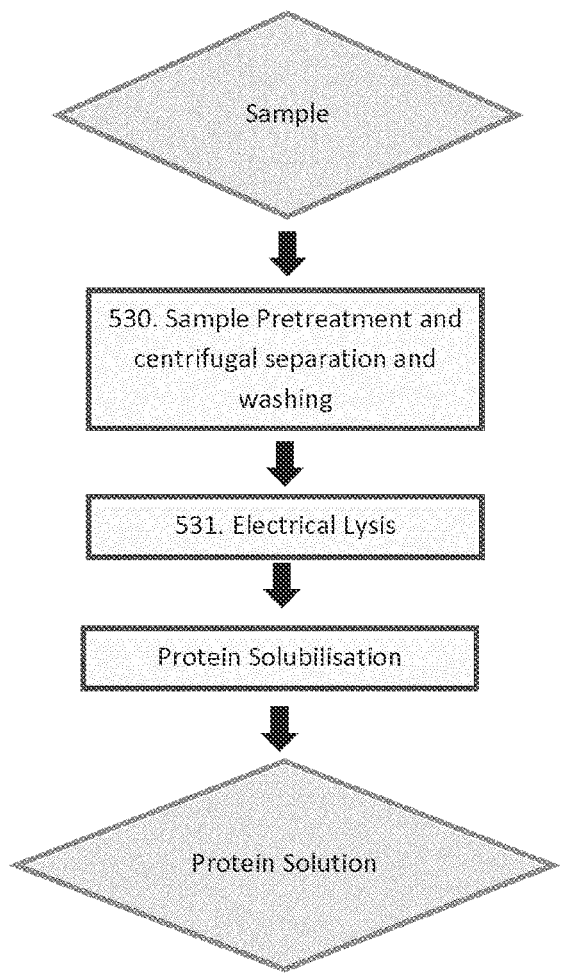
FIG. 7D is a flow chart describing a method of sample preparation, electrical lysis, and protein extraction, optionally for subsequently MALDI-TOF analysis, according to one example embodiment of the present disclosure.

Additionally, treatment of the lysate may be performed to prepare the lysate for other applications such as, for example, MALDI TOF mass spectroscopy for the phenotypic identification of microbes. Such applications may require the integration of a protein solubilization step with its required cartridge elements as shown in FIG. 7D. In an example of such a protein solubilization step, the lysate is passed into a chamber containing an organic solvent, such as acetonitrile, to dissolve as many proteins as possible. Then the cartridge is optionally centrifuged to sediment cell wall fragments and the supernatant is passed to a chamber which allows the protein solution to be retrieved from the cartridge by the user.

Figure 8:
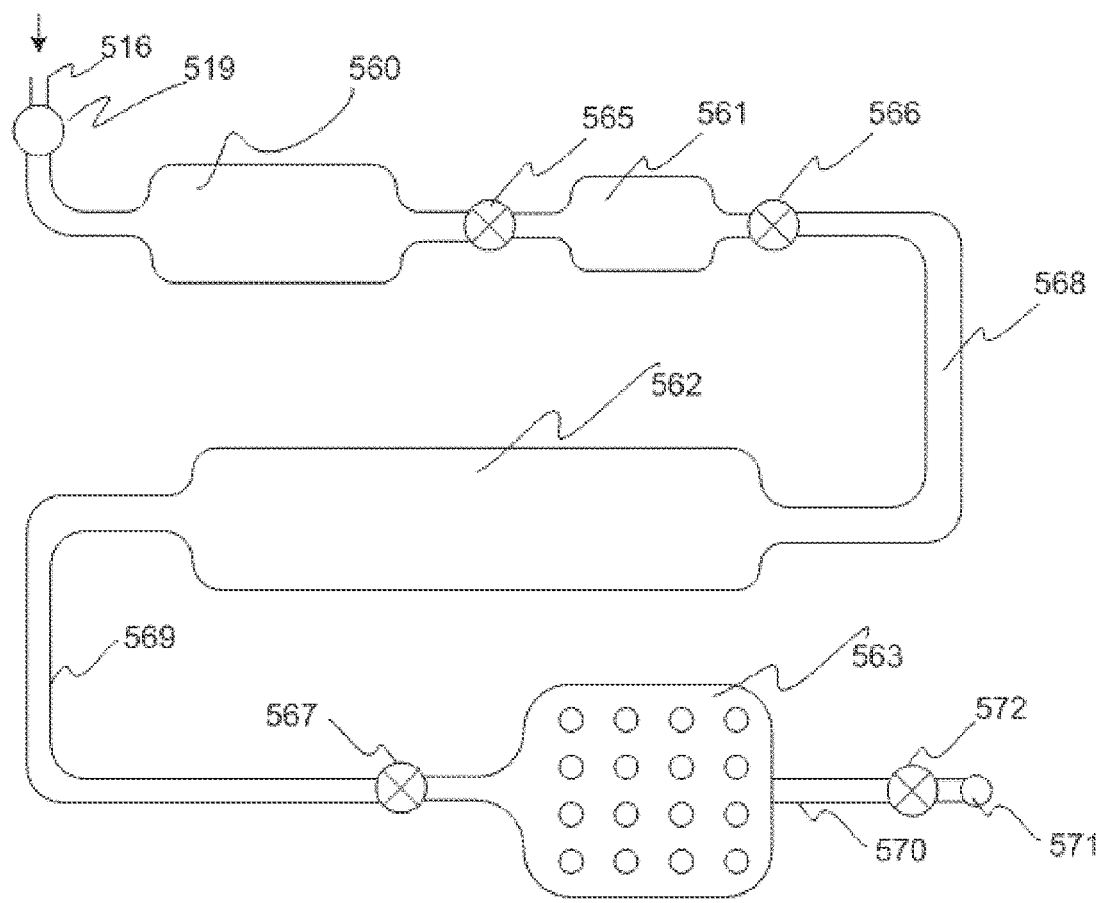
FIG. 8 is a schematic of a portion of an example integrated fluidic processing cartridge, in which additional fluidic components are provided for processing of separated and concentrated microbial cells.

With reference to the schematic representation in FIG. 8 and FIG. 5, some embodiments of the cartridge contain elements provided for the electrical lysis and treatment operation including a cell suspension chamber 560 connected via fluid path 516 and opening 519 to macrofluidic centrifugation chamber 502, electrical lysis chamber 561 and lysate chamber 562. The fluid path between the chambers 560 and 561 and between 561 and 562 contain shut-off valve 565 and 566 respectively. To effect fluid flow through this path by way of air displacement via port 518, valves 509, 512, and 513 are closed and valves 517, 565 and 566 are open. Furthermore an air path and vent must be provided at the furthest downstream extent of lysate chamber 562 to allow the lysate to flow into the chamber. The widths and the heights of the ell suspension, electrical lysis, and lysate chambers may be, respectively, selected in 1 mm-30 mm and 0.025 mm-1 mm ranges.

The final cell suspension is passed to the cell suspension chamber 560 by the extraction step 345 described previously where it is held prior to initiation of the electrical lysis and treatment process. Alternatively the cartridge does not contain a cell suspension chamber and the pretreated cell suspension may be passed directly to the electrical lysis chamber 561 in the manner described below. During this extraction step the downstream valves 565, 566, 567 and 572 are open to allow the fluid to flow through the channel 516 and into the holding chamber 560. Upon completion of the extraction step 345, the cartridge interfacing assembly 120 performs the operations necessary for the electrical lysis operation. The air displacement device attached to port 518 is used to displace a portion of the final cell suspension into the electrical lysis chamber 561 to fill the chamber. The valves 565 and 566 are then closed and an electrical pulse train is applied across the electrodes of the electrical lysis chamber in the manner described in US Patent Application Publication No. US20140004501, titled "METHODS AND DEVICES FOR ELECTRICAL SAMPLE PREPARATION", and filed on Jan. 25, 2013, which is herein incorporated by reference in its entirety, to effect microbial cell lysis and treatment of the cell suspension in the electrical lysis chamber producing microbial cell lysate 536.

In one example embodiment, which is intended for detecting pathogenic microorganisms in blood samples, the washing fluid is selected to have an ionic strength in 0.1-1 mM range, which is appropriate for the satisfactory operation of electrical lysis within the required lysis efficiency. The voltage pulse train consists of approximately 300 bipolar square pulses at a frequency of 10 kHz and equal amplitudes such that the electric field in the chamber is about 10 kV/cm. The cell suspension is briefly superheated to temperatures above approximately 120° C. to effectively lyse fungal cells. To avoid over-pressurizing the electrical chamber, the electrical chamber temperature is monitored during the pulse train to avoid over-pressurizing the chamber. This is done by monitoring the temperature dependent electrical current passing across the chamber in accordance with the methods of US Patent Application Publication No. US20140004501. In one embodiment this is achieved by measuring the peak electrical current averaged over about 5 first cycles of the pulse train and setting the maximum allowable peak current at about 3 times of this initial current. When the peak current reached the maximum allowable value, a control system lowers the pulse amplitude to about ⅓ of its initial value.

Upon completion of the electrical pulse train the valves 565 and 566 are opened and a further volume of pretreated cell suspension is displaced into the electrical lysis chamber in the same manner thus displacing an equal volume of the microbial cell lysate into the lysate chamber 562 via fluid path 568. The volume so displaced may be equal to the full electrical chamber volume or optionally a portion of the electrical chamber volume, the former displacing the entire volume of the microbial cell lysate and the latter displacing a portion of the microbial cell lysate into the fluid path 568 and chamber 562. The valves 565 and 566 are again closed and an electrical pulse train is applied to the electrical chamber. Further volumes of pretreated cell suspension are similarly displaced into the electrical lysis chamber and subjected to electrical lysis and subsequently displaced into chamber 562. Upon electrical lysis of the full volume of the cell suspension, or alternatively a portion thereof, the remainder of the microbial cell lysate is passed into the lysate chamber 562 by air displacement as described previously. The fluid path 569 emanating from lysate chamber 562 may terminate at a port for retrieval of the lysate sample as in FIG. 7C, or may lead to further conduits, valves and chambers required for further processing.

It will be understood that the electrical lysis method described herein is merely an example of a lysis method, and that other lysis methods may be used in alternative, such as bead beating, ultrasonic lysis (optionally with bead beating, and chemical lysis).

Reverse Transcription, PCR and Multiplexed Detection

With reference to the schematic representation in FIG. 8, some embodiments of the cartridge contain elements provided for reverse transcription of rRNA into cDNA and PCR amplification and detection of amplified cDNA and/or gDNA products. Some embodiments intended only for gDNA detection do not contain the elements required for reverse transcription. These elements include a fluid path 569 from the lysate chamber 562 to the thermal chamber or array of thermal chambers 563, a path 570 from the thermal chamber or array of thermal chambers to an air vent 571, optionally a valve 567 in the fluid path 569, and optionally a valve 572 in the path 570. Preferably the thermal chamber or array of thermal chambers contain the required reverse transcription reagents, PCR reagents, and primers in a dry form which respectively contain all constituents necessary for the reverse transcription and PCR processes. In one embodiment, a master mix solution containing the reverse transcription and DNA polymerase enzymes and appropriate preservatives, is dispensed in dry form on the wall of the thermal chambers. The master mix solution, containing the reverse transcription and DNA polymerase enzymes and appropriate preservatives, is dispensed in dry form on the wall of the thermal chambers.

The reverse and forward primers which are generally specific to the target microbial cells designated for each thermal chamber, are also deposited in dry form on the wall of the thermal chambers. In another embodiment the lysate chamber may contain some of these reagents in dry form. In one example embodiment the master mix solution may be deposited in dry form on the wall of lysate chamber 562. In one embodiment, the drying of master mix solution can be achieved by freeze-drying on the chamber surface. Alternatively, the master mix may be dried in the form of lyophilized beads and stored in the chamber. In another embodiment the master mix is supplemented with appropriate stabilizer agents before being air or vacuum dried on the surface. Exemplary implantation of this drying method has been provided in U.S. Pat. No. 8,900,856.

Upon exposure to the lysate solution the reagents are formulated to dissolve readily, aided in some embodiments by fluid flow over the dry reagents, agitation of the lysate fluid in contact with the dry reagents, heating of the fluid chambers which contain the dry reagents, or some combination of these mechanisms. In another embodiment liquid reagents may be stored in neighbouring chambers in the cartridge and fluid pathways and flow control elements are provided to transfer of such liquid reagents into the lysate chamber, the thermal chambers or into the fluid path to combine with the lysate.

Example Thermal Chamber

Figure 9A:
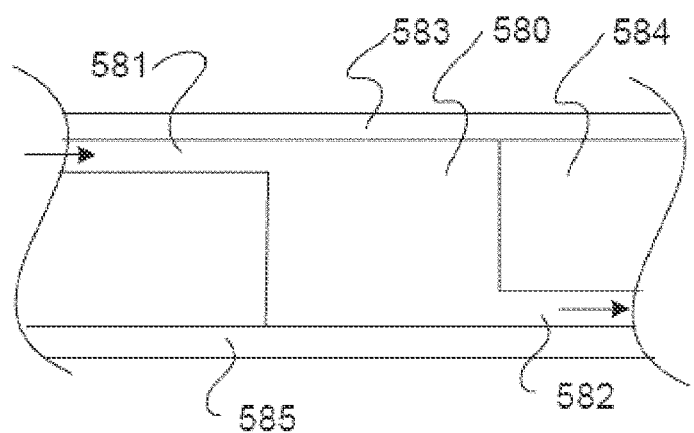
FIGS. 9A-B illustrate various example embodiments of a thermal chamber.
Figure 9B:
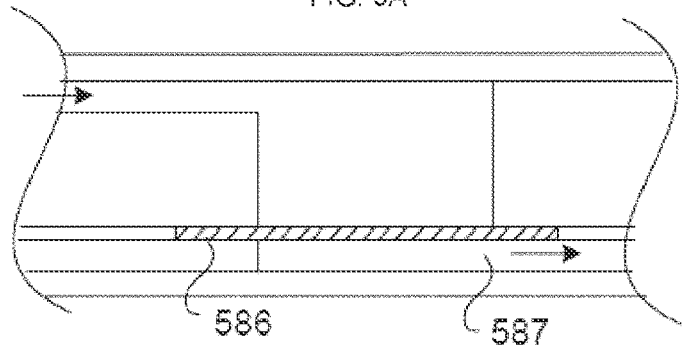
Figure 9C:
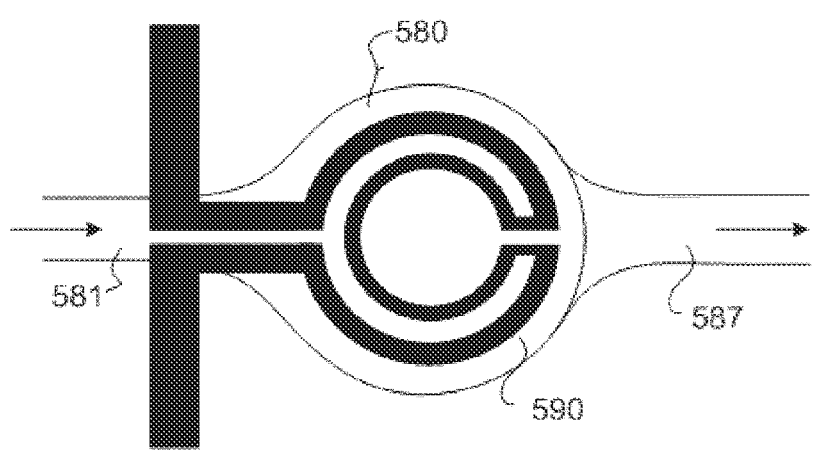
FIG. 9C is an illustration of an example heater element for use with a thermal chamber.

In some embodiments the thermal chamber is constructed as shown in FIGS. 9A-E. The heights and the diameters of these chambers may be selected to be, respectively, in 0.025 mm-3 mm and 0.1-5 mm ranges. FIG. 9A shows a cross-section view of an embodiment of a thermal chamber 580 where 583 is a top cover layer or film, 584 is a layer forming the sides of the chamber and 585 is a bottom layer. The chamber in plan view may be circular, as depicted in FIG. 9C, or may alternatively be square, rectangular or multi-sided. Top layer 583 of chamber 580 is constructed of a transparent material suitable for optical transmission of the wavelengths necessary for fluorescence excitation and measurement of the fluorescence signals from amplified PCR products. Alternatively the bottom layer may be constructed of such materials for this purpose. In this way PCR amplification products can be monitored in real time or detected at appropriate intervals in the thermal cycling process. The paths 581 and 582 are provided for fluid flow into or out of the chamber as required. These may be of the full height of the side wall layer 584 or, as is depicted in FIG. 9A, one or both of these may be a portion of the height of layer 584.

In another embodiment the outflow path 587 is formed in the layer adjacent to the bottom layer 586 as shown in FIG. 9B and the bottom layer 586 is an air permeable membrane which resists the passage of fluid at the working pressure of the cartridge. Such a construction can be used to eliminate air from the chamber during fluid filling or minimize the occurrence of air bubbles. When more than one thermal chamber is provided, such as for the case of an array of chambers 563, the individual chamber inlets may be fluidically connected to the fluid path 569 via a network of paths, bifurcations and interconnections.

Figure 9D:
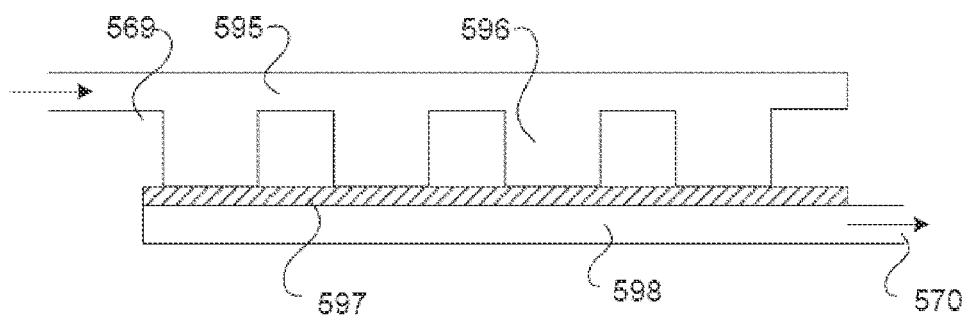
FIGS. 9D-E illustrate various example embodiments of an array of thermal chambers.
Figure 9E:
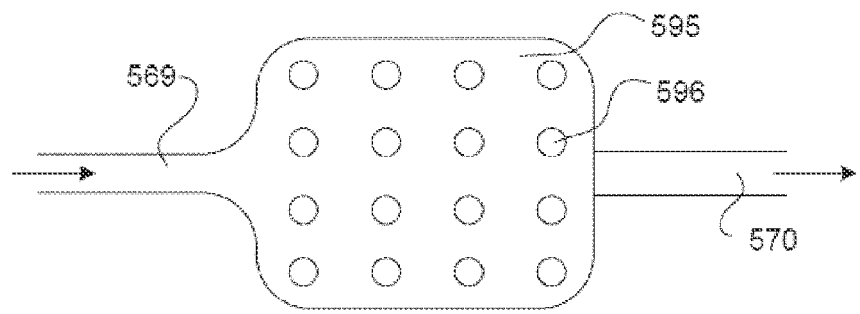

Alternatively the fluid path 569 may lead to a chamber 595 above the array of thermal chambers 596, as depicted in cross section view in FIG. 9D and in plan view in FIG. 9E. A bottom cavity 598 may also be provided as an alternative to multiple networked paths to connect to path 570. In this case the bottom of the thermal chamber may be an air permeable layer or membrane which prevents the movement of fluid into the cavity 598 and path 570.

A heating element 590, shown in FIG. 9C, is provided at the top surface, the bottom surface or the side surfaces of the chamber or some combination thereof. Heating element 590 may be a resistive heating element such as a wire, ribbon, or strip which produces heat by Joule heating when electrical current is supplied. Non-limiting example materials are Nichrome, Kanthal, carbon, copper or platinum. Alternatively, the heater may be formed from an etched metal foil, thin film or printed film. Such heating elements may form the bottom layer, top layer or side layer of the chamber or may be placed on or adjacent to one or more of these layers.

In some embodiments, a material or configuration with a high or moderately high thermal coefficient of resistance is used to form heating element 590, so that the heater temperature can be monitored allowing some embodiments to employ active feedback control of the heater temperature.

In other embodiments the heating element may be external to integrated fluidic processing cartridge 120. Examples of external heaters include resistive heater, radiative heater, convection heater, induction heater, or Peltier heater.

To enable thermal cycling, an active or passive cooling mechanisms may be introduced. Cooling methods include, but are not limited to, external passive cooling by heat sinking or active cooling using thermoelectric (Peltier) coolers, air or other fluid convection. Some embodiments possess integral passive cooling in which the materials of the walls, top and/or bottom layers or layers adjacent to one or more of the chamber surfaces possess thermal properties which allow heat to be rapidly conducted away from the chamber and absorbed by the neighbouring materials when heating is removed and the chamber temperature is greater than the temperature of the heat sinking materials. This may be aided by providing an external heat sink with a high heat capacity or an external heat sink which is actively cooled.

To move lysate into the thermal chamber or array of thermal chambers 563, the air displacement device connected to port 518 of FIG. 5 may be used to displace air into macrofluidic centrifugation chamber with valves 509, 512, and 513 closed and valves 517, 565, 566, 567 and 572 open, thereby displacing lysate from the lysate chamber to the thermal chambers. In an alternate embodiment the air vent 571 may be also be configured as a port which allows connection of an air displacement device such as a syringe pump, peristaltic pump, bellows pump or any other air displacement device or pressure source which can controllably deliver or remove air. The air displacement device is engaged with the port 571 by way of a connector on the cartridge interfacing assembly 130 which provides a sealed connection with the port. Optionally a rigid or flexible tube connects the air displacement device to the connector to allow the air displacement device to be remote from the cartridge interfacing assembly. This embodiment allows the liquids in the chambers and conduits of FIG. 8 to be moved in the direction of port 571 by evacuating air via port 571 The valves 517, 565, 566, 567 and 572 in the path from macrofluidic centrifugation chamber 502 must be open and macrofluidic centrifugation chamber must be vented to atmosphere via one of the available paths. Alternatively, an air vent or multiple air vents, controlled by shutoff valves, may be supplied at various positions along the fluid path to allow air evacuation from port 571 to transfer fluid. This method of fluid movement may be optionally be applied to one or more of the following fluid transfer actions: the extraction of pretreated cell suspension from macrofluidic centrifugation chamber, the transfer of cell suspension into the electrical lysis chamber, the transfer of lysate into the lysate chamber and the transfer of lysate to the thermal chamber.

Performing RT-PCR in Thermal Chambers

In the embodiments described above for which the master mix including reverse transcription reagents and required primers are provided in dry form in the lysate chamber and the reverse transcription step may be performed in that chamber. Thereby, following dissolution of the dry reagent in the lysate solution, the lysate chamber is heated in a manner and with embodiments similar to that described above for the thermal chambers in accordance with the reverse transcription protocol. Following reverse transcription the solution containing the reverse transcription products (cDNA) is transferred to the thermal chambers along with the PCR components of the master mix. Forward primers, stored in dry form in each thermal chamber, are released into the liquid media and thermal cycling is performed in accordance with a predetermined sequence of temperatures and dwell times.

Alternatively, dry reagent is dissolved in the lysate solution within the lysate chamber and is directly introduced into the thermal chambers. The locally dried reverse and forward primers are thereby released into the lysate solution and reverse transcription and PCR amplification are performed.

Optionally, the port 571 is used to apply a vacuum to the thermal chambers to evacuate air from the thermal chambers and minimize the trapping of air bubbles in the chambers when liquid is drawn into the chambers. Prior to initiation of the PCR the valves 567 and 572 may be closed to prevent fluid movement and/or expansion of residual air present in the thermal chambers during thermal cycling. Optionally, prior to thermal cycling, the thermal chambers may be placed under pressure by closing valve 567 and applying positive pressure to port 571. Positive pressure may continue to be applied to port 571 during the thermal cycling process, or alternatively in embodiments containing valve 572, the valve may be closed after positive pressure at port 571 has been applied and prior to thermal cycling. Applying positive pressure will increase the vapour pressure in the thermal chamber and inhibit the creation and growth of air bubbles during the elevated temperature portions of the thermal cycles. In alternative embodiments, the pressure may be applied by air displacement via port 518 of the macrofluidic centrifugation chamber.

The amplification of target DNA molecules in the thermal chamber may be monitored by an optical system. In one example implementation, a light source such as an LED may be employed that emits in the wavelength range corresponding to the excitation band of the dye used in the PCR master mix and having no or very little emission in the wavelengths extending into the fluorescence emission spectra of the dye. The light from the LED after passing through a wavelength-selective mirror, illuminates the amplicons in the thermal chambers. The fluorescent dye included in the thermal chamber emits in a characteristic spectrum with intensity dependent on the chamber temperature. The emission light after being reflected from the wavelength selective mirror is imaged on a detector array. The wavelength selective mirror significantly attenuates the contribution of scattered excitation light in the emission beam. The imaging of the thermal chamber array is performed during a pre-selected period in the temperature cycling procedure of the PCR reaction. Optionally, at the end of thermal cycling the temperature of the thermal array is scanned with an appropriate rate and the fluorescence signal from the chambers is recorded at selected time intervals. This process is intended for performing melting analysis on the amplicons.

Figure 19:
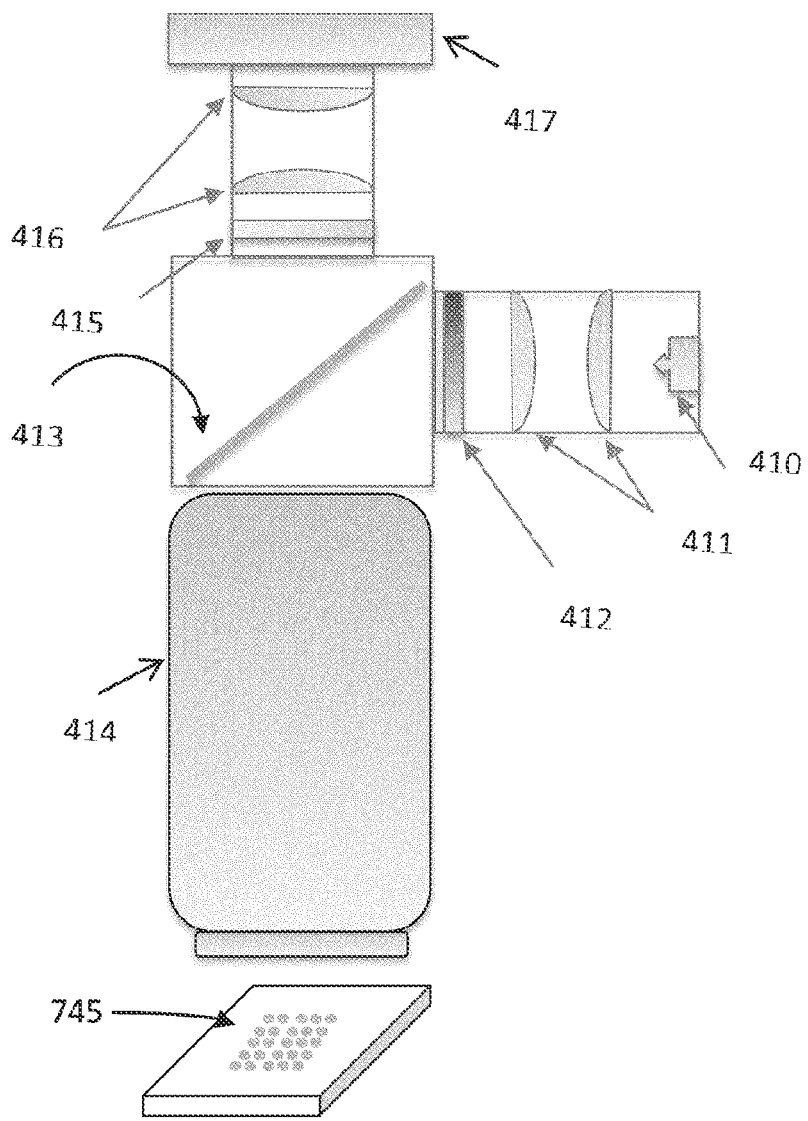
FIG. 19 illustrates an example optical system that can be optionally integrated with the cartridge interfacing assembly.

An example implementation of the optical system is presented in FIG. 19. The system includes an LED, 410, whose light is collected and substantially collimated by the lens combination, 411 and is filtered by passing through a low pass filter 412 to attenuate the part of spectrum overlapping with the emission spectrum of the fluorescent dye. The collimated beam after reflection from a dichroic mirror 413 and passing through microscopic objective 414 illuminates the thermal chamber array 745. The objective magnification may be selected according to the size of the thermal chamber array 745. For instance, if the thermal chamber covers a spatial dimension of 15 mm×15 mm then a standard microscope objective having a magnification in the range of 1×-1.5× may be selected. The fluorescence emission, emanating from the thermal chambers, is collected by the said objective, and after undergoing filtering by the dichroic mirror 413 is further filtered by the emission filter 415. This filtering action further attenuates the signals originating from the excitation source and pass through most of the fluorescence signal from the thermal chamber. The light transmitted through the excitation filter is imaged by the lens combination 416 onto an array of photodetectors 417 which may be in the form of CCD or CMOS sensors.

Although many of the examples provided herein relate to performing RT-PCR on a lysate obtained though performing lysis in the microfluidic device, it will be understood that other assays may be performed, such as PCR of DNA present in the lysate, such as nested PCR. Furthermore, it will be understood that other detection modalities other than optical detection may be employed, such as electrochemical sensing, and sensing via nuclear magnetic resonance assays known in the art.

Figure 10A:
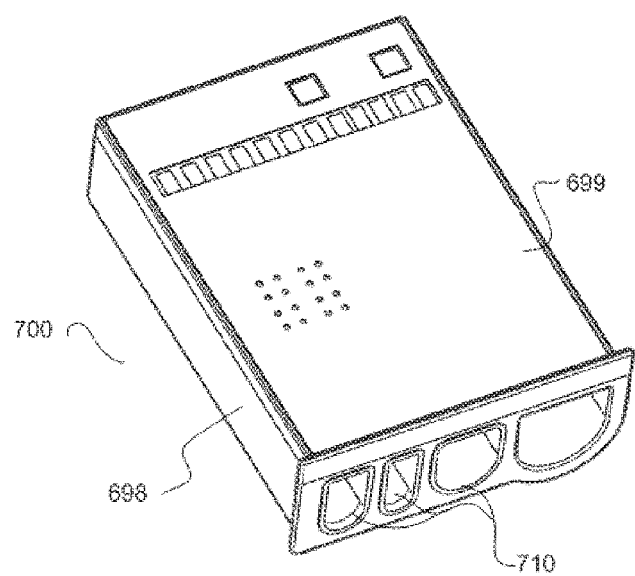
FIG. 10A is an illustration of an example integrated fluidic processing cartridge, showing front and back lateral surfaces from an isometric view.
Figure 10A:
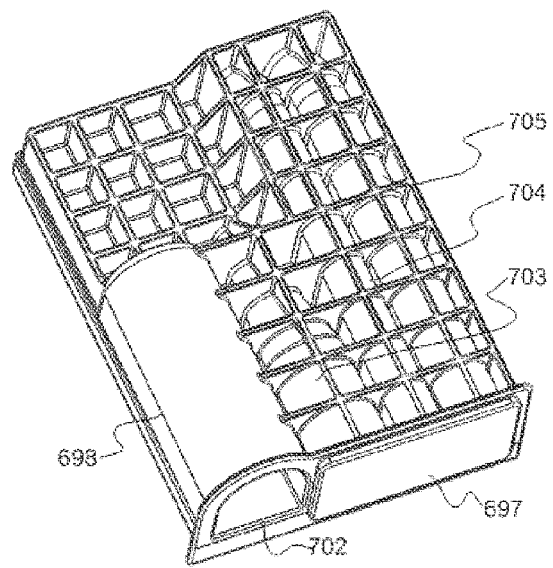

Example Integrated Fluidic Processing Cartridge with Integrated Molecular Assay Microfluidic Device FIG. 10A shows an example integrated cartridge 700 for microbial identification in a whole blood sample, which incorporates sample withdrawal from a Vacutainer type blood sample tube, sample pretreatment, centrifugal separation and washing, electrical lysis and treatment, reverse transcription, PCR and detection of target PCR amplified products.

Example integrated cartridge 700 is shown having three components, the first component 698 comprising the sample transfer receptacle 702, macrofluidic centrifugation chamber 703, the diluent chamber 704 and supernatant chamber 705. First component 698 may be a single plastic molded part fabricated from materials which are compatible with the form and function of the device. Alternatively, first component 698 may be an assembly of subcomponents which are plastic parts, molded or formed by a means consistent with the material, form and function of the device. In this respect, the material should be selected to be of sufficiently high strength to withstand the high centrifugal forces that the cartridge will be subjected to, and the materials should be compatible with the fluids used and, in the case of molecular applications, should not introduce contaminants into the pretreated cell suspension which will interfere with downstream process. Non-limiting examples of materials from which first component 698 can be fabricated are polypropylene, polycarbonate, polyethylene, PET, polystyrene, Cyclic Olefin Copolymer or some variant of these materials.

The second component 699 is a microfluidic device mounted on the lateral face of component 698 comprises fluidic paths and valves connecting the chambers in component 698 and components for electrical lysis, reverse transcription and PCR. The second component 699 is a laminate comprised of a number of layers in which are formed holes, channels and chambers and electrical components for electrical lysis and heating operations.

The layers may be machined, punched, embossed or molded to form the necessary features. Each layer may be comprised of either a single or multiple sublayers each of either different materials or the same materials listed previously based on the function of said sublayer laminated by either adhesives bonding, thermal bonding, ultrasonic bonding, or other methods known to those skilled in the art. The layers and sublayers presented are grouped solely for the purpose of ease of understanding the embodiment being discussed. In the present example implementation involving molecular processing, the materials should be compatible with the fluids and in cases in which molecular amplification is to be performed, the materials should not introduce substances inhibitory to such amplification (e.g. RT-PCR) or which interfere with detection of target microbes, and should not be contaminated with non-target analyte (e.g. non-target microbial cells) or nucleic acids. The materials should also not adsorb target molecules, reactants, and reagent components to an extent which will interfere with the process. Example plastic materials and plastic film materials include, but are not limited to, polycarbonate, polypropylene, PET, and cyclic olefins.

The chamber openings 710 may be sealed with a membrane seal, a foil seal or a cap 697 following dispensing of the wash buffer and pretreatment fluid into the diluent chamber and macrofluidic centrifugation chamber respectively. The seals or caps may be bonded using methods and materials compatible with heat sealing, adhesive bonding, ultrasonic bonding. Alternatively, the chambers may be sealed prior to dispensing of these liquids and alternate ports may be provided for the purpose of dispensing these liquids and these ports may be sealed following the dispense operation. The cap 697 may be molded, embossed, machined or rapid prototyped, and may be constructed from polycarbonate, polystyrene, PET, polyester or other material appropriate to its form and function.

Figure 10B:
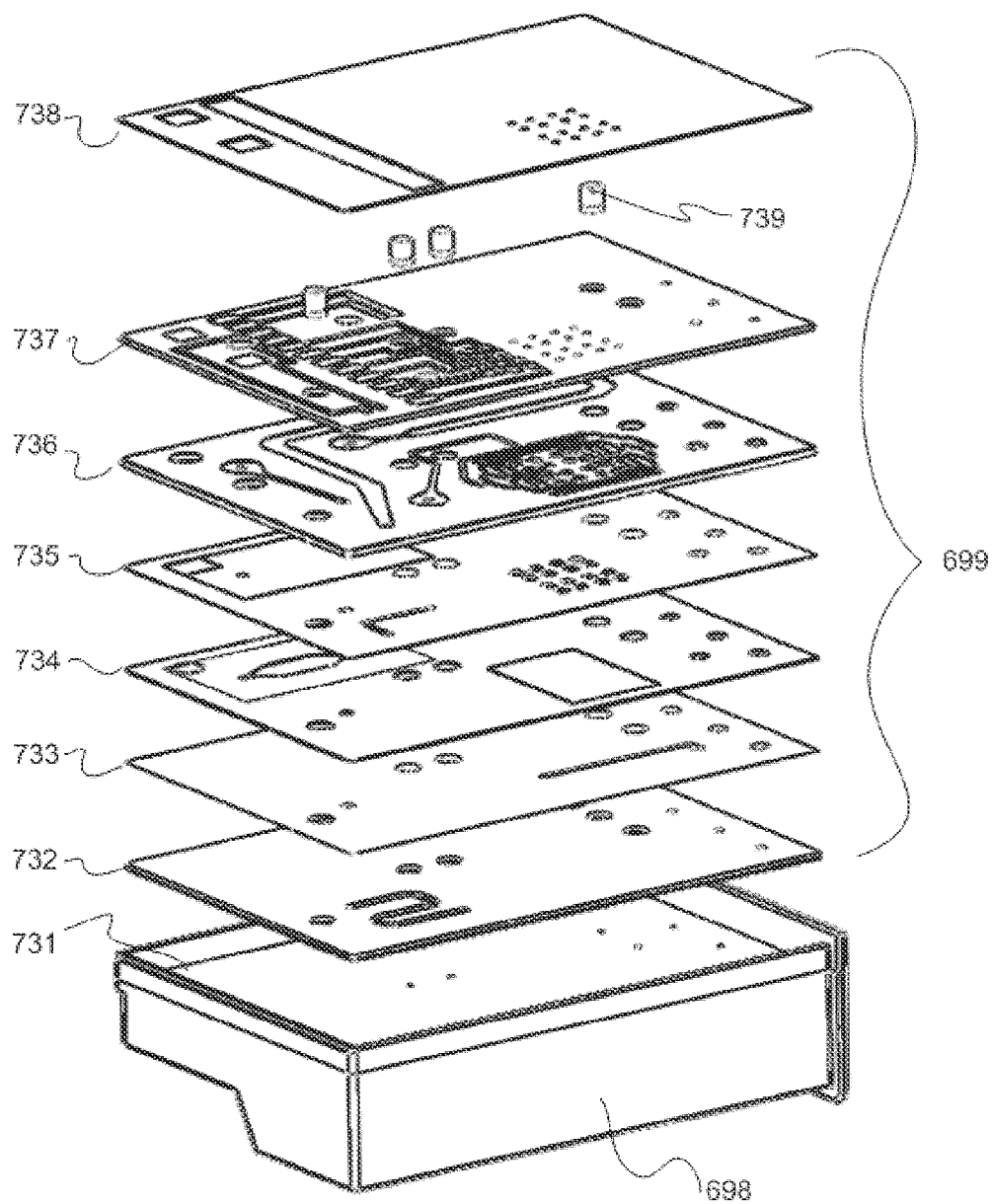
FIG. 10B is an illustration of an example integrated fluidic processing cartridge, showing an exploded view.
Figure 10C:
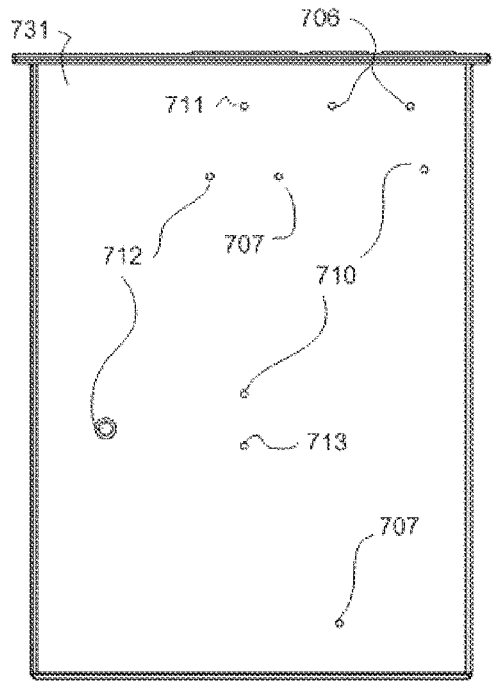
FIG. 10C-K is an illustration of an example multi-laminate integrated fluidic processing cartridge, showing detail of the major layers.
Figure 10D:
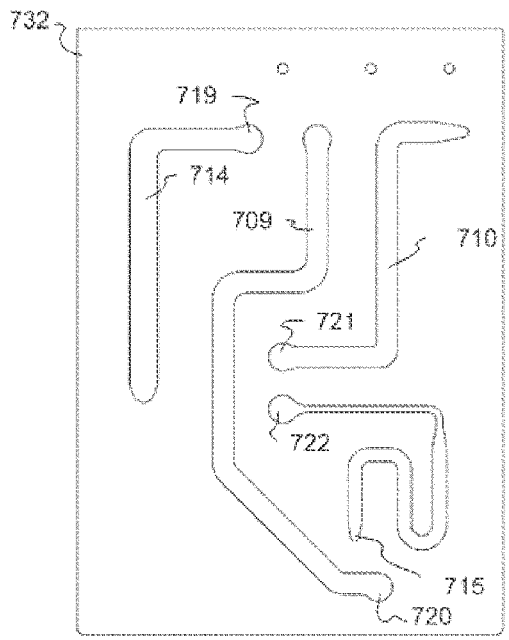
Figure 10E:
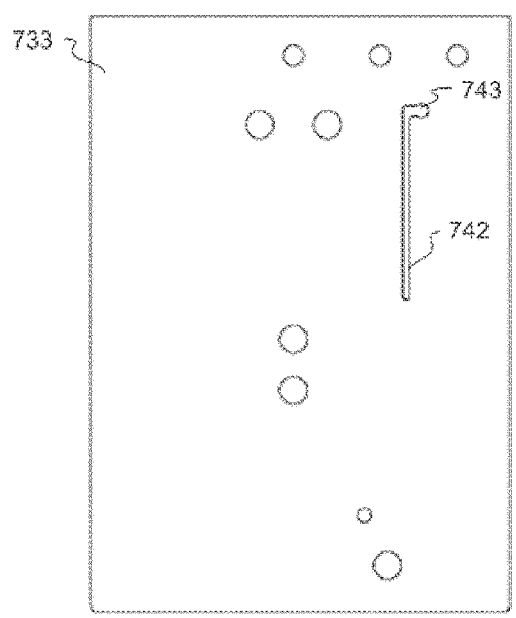
Figure 10F:
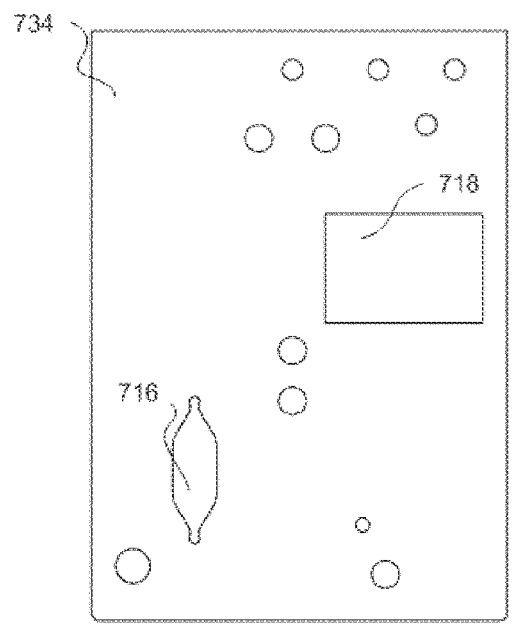
Figure 10G:
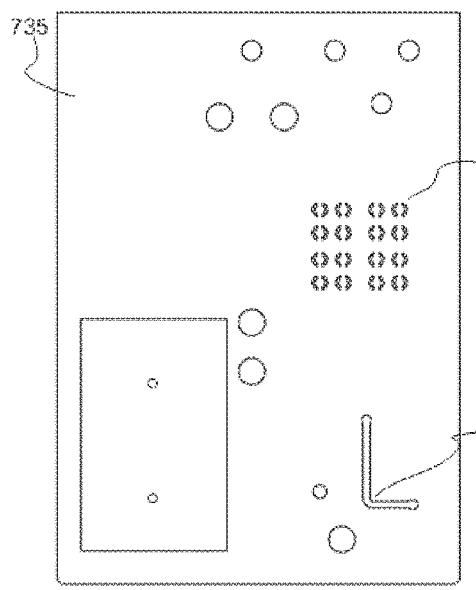
Figure 10H:
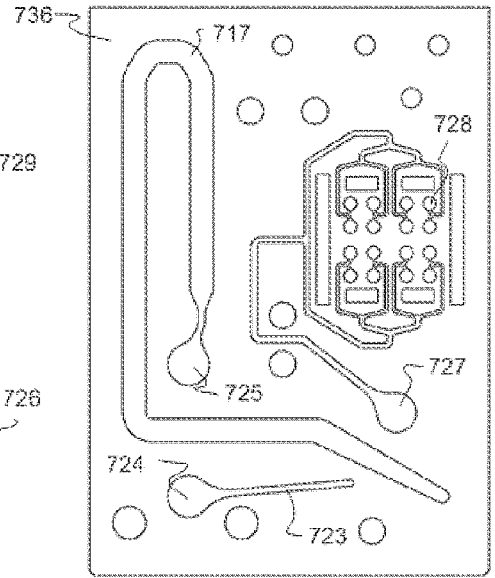
Figure 10I:
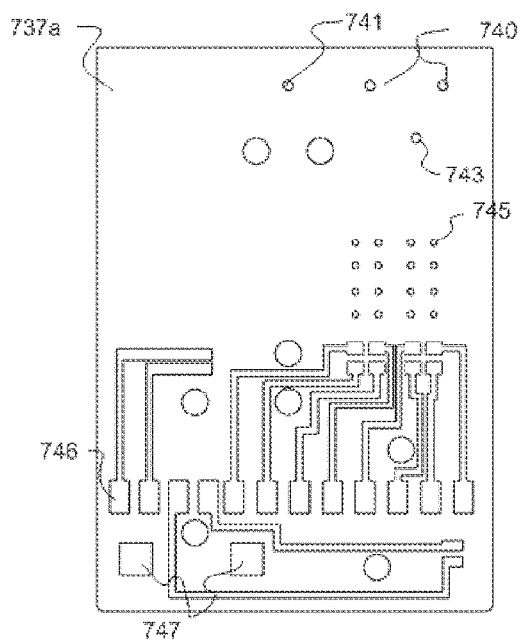
Figure 10J:
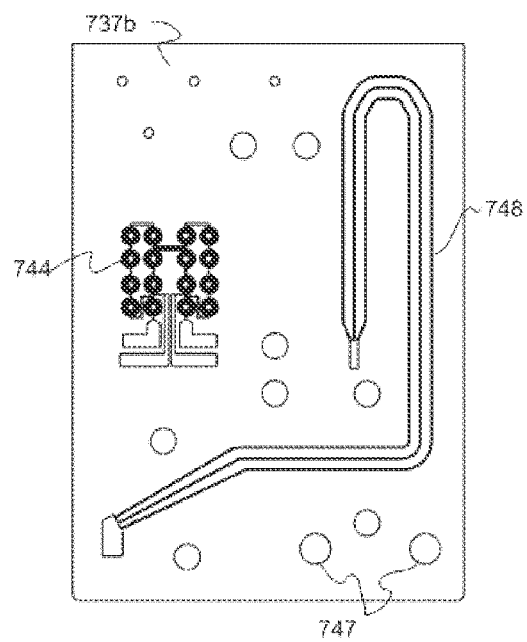
Figure 10K:
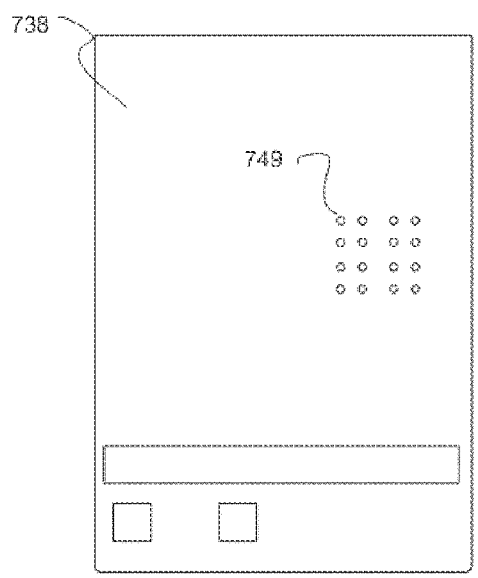

FIG. 10B provides an exploded view of the integrated cartridge 700, illustrating the stack up of the layers broken down in FIG. 10C-K, which illustrates the main elements of each component. Each of the chambers in the first component 698 possesses holes which lead from the respective chamber to the top plane 731 of first component 698, for connection to fluid paths, vents, valves, and injection ports which are all within an upper laminated layer 699. The upper laminated layer 699 also contains all the elements for electrical lysing, reverse transcription, PCR and detection of PCR products as described previously.

Diluent chamber 704 is connected fluidically to the macrofluidic centrifugation chamber 703 via a pair of holes 707 in layer 731 and fluidic conduit 709 in layer 732 and flow through this path is controlled by the valve 720, the membrane of which is on the top face of 732. Supernatant chamber 705 is connected fluidically to macrofluidic centrifugation chamber 703 via a pair of holes 708 in layer 731 and fluidic conduit 710 in 732 and fluid flow through this conduit is controlled by valve 721, the membrane of which is on the top face of 732.

Diluent chamber 704 and supernatant chamber 705 also each possess a hole 706 in layer 731, which respectively leads to a vent 740 on the upper layer 737 via complementary holes in the intermediate layers. Macrofluidic centrifugation chamber 703 possesses hole 711 in layer 731 which leads to an air injection port 741 on the upper layer 737. A pair of holes 712 in 731 and fluidic conduit 714 in 732 provide a fluidic connection between the needle in the sample transfer receptacle 702 and macrofluidic centrifugation chamber 703 in component 698, and flow within fluidic conduit 714 is controlled by valve 719, the membrane of which is on the top face of 732.

The sample centrifugation and wash processes described above can be implemented on integrated cartridge 700 by way of air displacement via port 741, and the selective closing and opening of the various valves. Sample fluid may be directed from the sample tube 520 which is inserted in the sample transfer receptacle 702 via path 714 in layer 732. Subsequently, after centrifugation, supernatant from macrofluidic centrifugation chamber 703 may be directed to the supernatant chamber 705 via conduit 710 in layer 732, and diluent liquid may be directed from diluent chamber 704 to macrofluidic centrifugation chamber 703 via path 709 in layer 732. Following the completion of the centrifugal separation and wash process described above, valve 722, whose membrane is located on the top surface of layer 732 is opened and the final cell suspension in macrofluidic centrifugation chamber 703 is displaced via hole 713 in layer 731 to collection chamber/conduit 715 in layer 732.

In the example embodiment shown, the displacement of the residual cell suspension to and from macrofluidic centrifugation chamber occur by air displacement into and out of port 741, by way of an air displacement pump connected to port 741. Following the displacement of the residual cell suspension to collection chamber 715, subsequent displacements of fluid occur by air displacement through port 743 in layer 737 by way of an air displacement pump connected to port 743. In an alternative embodiment fluid displacements continue to be activated by air displacement through port 741 and port 743 forms a vent.

Suspension chamber 715 is connected via a hole through intervening layer 733 and 734 to fluid path 723 in layer 736 and subsequently through valve 724 which is located on the top surface of 736 to the electrical lysing chamber 716, though the intervening holes on 735. The lysing chamber faces are constructed of surface enhanced oxidized electrodes as described in US Patent Application No. US20120190040, titled "CELL CONCENTRATION, CAPTURE AND LYSIS DEVICES AND METHODS OF USE THEREOF" and filed on Apr. 16, 2012, which is incorporated herein by reference in its entirety, and in US Patent Application Publication No. US20140004501, and these electrodes are electrically connected through the intervening layers to the terminals 747 in layer 737 exposed on the upper face of the cartridge. Electrical connection between the electrodes and the respective terminals (contacts) may be made by wire bonding, bonding of a conductive element between the layers or sandwiching a conductive element between the layers.

Lysing chamber 716 in layer 734 is connected fluidically through valve 725 in layer 736 to fluid path and lysate chamber 717. Dry format reagents are optionally deposited on either the top or bottom face of chamber 717. Lysate chamber 717 is connected to fluid conduit 726 in layer 735, which leads to valve 727 in layer 736 and the network of fluid paths and thermal chambers 728 in layer 736.

The bottom surface of chambers 728 may optionally be an air permeable membrane layer 718 which allows flow of air or other gases, but not liquid, through the membrane to path 742 in layer 733 leading to port 743. An example material is porous PTFE membranes or other materials. The top surface of 736 is a membrane which is optically transparent, for example, to the excitation and emission spectra of the fluorophore dyes in PCR reagents, and sufficiently thin, to serve as the membrane material for valve 724 and 725. Example materials for this purpose include, but are not limited to, polycarbonate, cyclic olefins, PET or other membranes films. In applications involving fluorescence detection, materials employed for the chamber side and bottom layers should be selected so as to minimize autofluorescence emission, which may otherwise interfere with PCR signal detection. In the case of a PTFE membrane which is typically white, layer 735 may be opaque, and features 729 which make up the bottom of chambers 728 prevent the imaging of the underlying white membrane in the center of the chamber, however allow the passage of air around the outside perimeter of each chamber 728.

Dry reagents are optionally deposited on either to top or bottom surface of thermal chambers 728.

The top surface of the thermal chambers 728 in layer 738 contact the bottom surface 737b of layer 737 which possesses an array of resistive heaters 744 in a pattern matching the array of thermal chambers in layer 736. Alternately the resistive heaters may be applied or printed directly on the top surface of the thermal chambers. The resistive heaters are configured to heat the each chamber while allowing the optical signal to pass through. For example, the individual chamber heaters may be in the form of a circular trace near the outside perimeter of the chamber leaving a clear inner region for optical transmission as shown by 745.

Likewise, a resistive heater 748 on 737b may be in contact with or applied to the top surface of lysate chamber 717 to optionally allow heating of that chamber. The resistive heaters are powered and the monitored via connection by the instrument (e.g. control and processing unit 140) to exposed terminals 746.

Layers 734, 735, 736, 737, and or 738 may have thermal properties which allow dissipation of heat from the thermal chambers during the cooling phase of the PCR thermal cycles. Alternatively, a layer with properties such as, for example, an aluminum foil layer, may be placed in close proximity to the thermal chambers, for example layer 738 to dissipate heat for cooling purposes. This layer must have holes and cutouts to prevent interference with fluid and air paths described.

Thus the cell suspension in suspension chamber 715 is drawn into the lysing chamber 716 by opening all valves in the path to the port 743 and evacuating air from the fluid path through this port by way of an air displacement pump. For this action, valve 722 to macrofluidic centrifugation chamber is also open and a path to atmosphere is provided from macrofluidic centrifugation chamber, via for example port 741. Alternatively the path to atmosphere from macrofluidic centrifugation chamber could be via one of the fluid paths (with valves open) to wash vent or the waste vent 740.

In the present example implementation involving electrical lysis, the cell suspension is electrically lysed and treated by intermittently flowing a portion of the cell suspension into the chamber 716, closing the valves 724 and 725, and applying the electrical train of bipolar pulses as described previously. According to the present example implementation, electrical lysis is performed serially in order to avoid the need to treat the full suspension at once, which reduces the electrical current that is required. Valves 724 and 725 are then opened and a further volume of cell suspension is passed into the chamber 716 thus displacing the previously lysed cell suspension to chamber 717. A volume equal to the volume of the chamber 716 or optionally a portion of the full chamber volume may be passed into the chamber at each subsequent electrical lysing step to ensure that all of the cell suspension is lysed during the sequence of lysing steps.

Lysing is complete after the full volume of cell suspension has been passed into the chamber 716 and the resulting lysate has been passed into chamber 717. The lysate in the chamber 717 will dissolve the reagent which has optionally been placed on the bottom or upper surface of the chamber. The dissolving process can optionally be assisted by raising the temperature of the fluid to approximately 40° C. applied by heater 748. Optionally the lysate fluid may be passed back and forth through the fluidic path comprising the lysate chamber 717, the electrical lysis chamber 716 and the cell suspension chamber 715 and the fluidic paths, holes and valves in the fluidic path between these by alternate injection and evacuation of air through port 743. This action may promote dissolving of the dry reagents and also promotes lateral and longitudinal mixing of the fluid via Taylor dispersion to increase the homogeneity of the solution with respect to reagent components and target nucleic acids.

The lysate reagent solution is then passed through to the thermal chambers by drawing air through port 743. The negative pressure produced at the exit from the permeable membrane 718 in path 742 will promote the evacuation of air and air bubbles from the chambers. Valve 727 is then closed and a positive pressure is optionally applied a port 743. Dry reagents present on one or more of the surfaces of the chamber will dissolve to provide the primers and optionally other components necessary for RT-PCR. The RT-PCR thermal protocol is then initiated using the heater 744 and the cooling methods described previously.

Optionally a valve is placed in the path to vent 743 and this valve is closed with valve 727 prior to the initiation of RT-PCR heating and thermal cycling.

In an alternate embodiment, the path from the lysis chamber 716 leads to a lysate chamber which is formed in the cartridge component 698 A lyophilized bead placed in this chamber contains some or all of the required reagents for RT and/or PCR. The volume of this chamber is of sufficient dimensions to contain the bead and of sufficient volume to contain the required volume of lysate. The lyophilized reagents are then dissolved and the solution is optionally mixed to promote dissolution and homogeneity of the mixture. Additional volume may optionally be provided in this lysate chamber so that the solution can be effectively mixed via vortexing of the cartridge.

The actuation of valves and the application of air displacement pressure may be performed over all process steps while integrated fluidic processing cartridge 120 is housed within centrifuge 110. However, in other embodiments, the system may include a separate housing for receiving one or more integrated fluidic processing cartridges 120, where the separation housing is not configured as a rotor for centrifugation, but does include a suitable cartridge interfacing mechanism for actuating the valves and controlling fluid flow within integrated fluidic processing cartridge. This separate housing may be employed to control the actuation of fluids within the microfluidic device of integrated fluidic processing cartridge 120 during assay steps, or other steps, that are performed post-centrifugation and post-washing, thereby freeing centrifuge 110 to be able to process an additional integrated fluidic processing cartridge during the subsequent processing of the first integrated fluidic processing cartridge.

In an embodiment where the valves 722, 721, 720 and 724 are to be closed prior to engagement within the receptacle, and cartridge interfacing assembly 130, captive plungers 739 are included and held within the cartridge by layer 738. Further detail for the valve operation are described below. An example for this embodiment may be to prevent movement of fluids held within chambers 703, 704, or 705 from flowing into component 699 with between each other via fluid paths 710, 709, 714, or 715 during shipment of the cartridge 700.

Examples of Valves

Figure 11A:
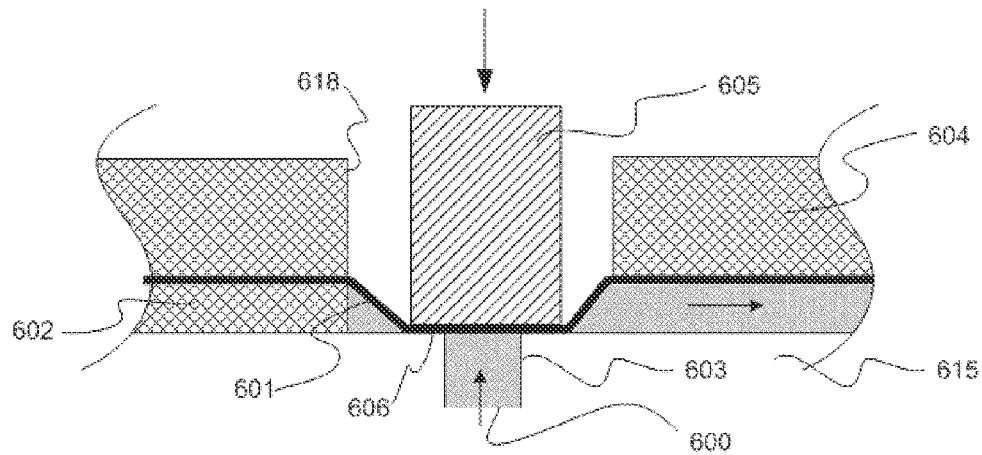
FIGS. 11A-I provide illustrations of example embodiments of a valve and associated plunger.
Figure 11B:
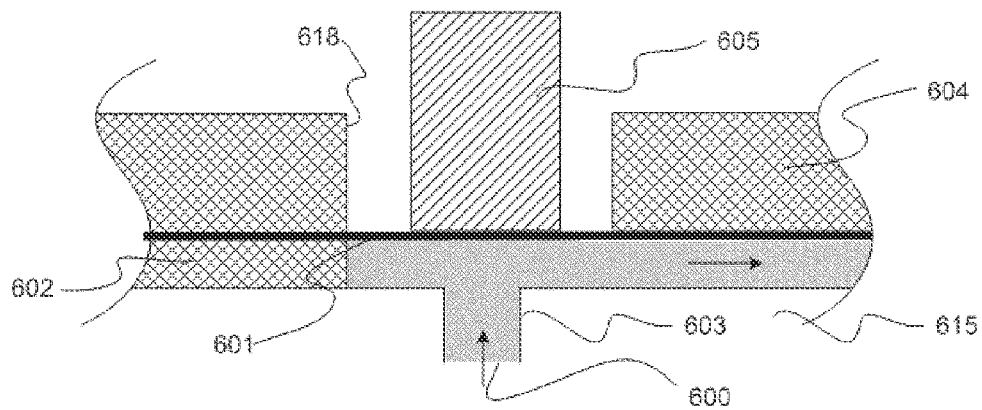
Figure 11C:
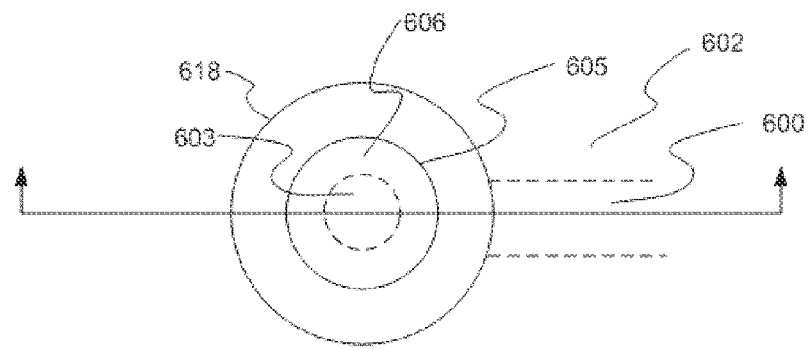

The integrated fluidic processing cartridge depicted in FIG. 10 employs, as an example, diaphragm valves, as detailed in FIGS. 11A-C.

FIG. 11A depicts a diaphragm valve which is closed by application of an external plunger 605 on a membrane diaphragm 601, which thus applies pressure to the membrane 601 circumferential to the port (hole) 603 and seals the port 603 preventing flow in fluid path 600. FIG. 11B depicts the valve in the open state, where no external force is applied downward on plunger 605. FIG. 11C depicts the plan view of the diaphragm valve illustrating the sealing pressure zone 606. In the embodiment depicted, plunger 605 may be provided as a component of an actuator which acts on the cartridge. Alternatively the plunger may be a component of the integrated fluidic processing cartridge where plungers are held captive in the valve pocket by a membrane covering the valve pocket. In this case the captive plunger is acted upon by an external actuator which delivers the force necessary to close the valve and is provided either by the cartridge receptacle which is part of the motorized rotor of FIG. 1 or by the cartridge interfacing assembly 130 of FIG. 1.

Microfluidic layer 602, having a lateral microfluidic channel formed therein, is bonded to valve base layer 615 which together form the fluidic path 600, where microfluidic layer includes a valve seat aperture 618 in fluid communication with the lateral microfluidic channel, where the valve seat aperture is positioned over the port 603 and extends through the microfluidic layer 602. Optionally, microfluidic layer 602 can be comprised of multiple layers which may comprise the top and bottom walls of the fluid path, with the exception of the valve seat aperture (valve cavity) 618, where the top surface is the membrane diaphragm. The membrane diaphragm 601 is bonded to layer 602, and provides to top surface of fluid path 600 within the valve seat aperture. The valve membrane diaphragm 601 may optionally be further sandwiched between layer 602 and outer layer 604. The membrane diaphragm may also optionally be manufactured such that some or all of the layers 602, 601 and 604 are a single part with no bonding required, for example by molding, micromachining, embossing or other methods known by those skilled in the art. Retraction of plunger 605, or sufficient relaxation of the force with which plunger 605 is applied to the valve, allows fluid to flow between along fluid path 600 as shown in FIG. 11B. The valve geometry and membrane material may be selected by one skilled in the art so that under the closure force the membrane does not rupture. Additionally, in the embodiment shown the valve plunger should be sufficiently large to provide sufficient area to form a seal around port 603. This may be at a minimum approximately 2 time the diameter of the port 603

In the embodiment of FIG. 11A, without the application of force to the plunger 605, the membrane will not seal the port 603 and fluid may flow along fluid path 600 as shown in FIG. 11B. This embodiment is acceptable when the fluid path does not need to be closed prior to actuation or prior to engagement with the cartridge interfacing assembly. In many circumstances it is necessary that some or all of the valves in the integrated fluidic processing cartridge be closed in the absence of an actuator mechanism. For example it may be desired to have valves 720, 721, 722, and 719 in FIG. 10D closed during handling, transportation and storage of the cartridge to prevent fluids preloaded into macrofluidic centrifugation chamber 703 and diluent chamber 704 from passing to other chambers or fluidic paths prior to initiation of cartridge sample preparation operations.

Figure 11D:
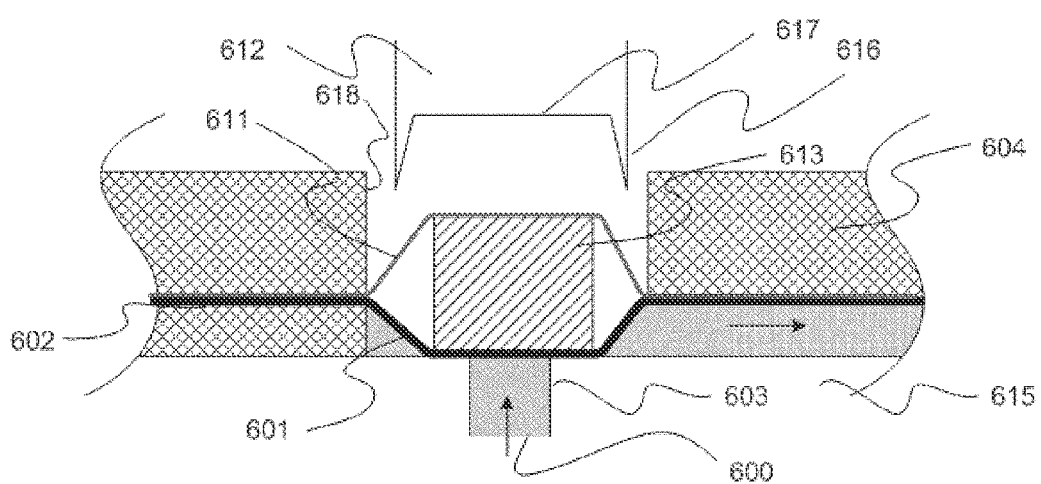

FIG. 11D illustrates another embodiment of the diaphragm valve which has the added feature of being closed without the application of an external actuator. In this case, a captive internal plunger 613 is supplied which is placed between an outer membrane 611 and the diaphragm membrane 601. The captive internal plunger may be bonded to the outer membrane 611 and/or the membrane 601. Membrane 611 may be bonded to the membrane layer 601 or there may be additional layers between 601 and 611. Membrane 611 may optionally be sandwiched with a covering layer 604. The captive plunger 613 is dimensioned such that it extends above the top level of layer 602 when the valve membrane 601 is in the closed position and the membrane is applied such that within the valve seat aperture 618, it is under a tensile stress sufficient to supply a reactive compressive pressure to the captive plunger 613 which is sufficient to seal port 603 with the membrane diaphragm 601. This embodiment allows the cartridge to be transported, stored and handled without liquid transfer between the chambers of the cartridge or between the chambers and the microfluidic backplane of the cartridge. This is particularly useful, for example, when a pre-treatment fluid is present in the centrifugation chamber or when a wash diluent solution if present in the diluent chamber.

In one exemplary method the membrane is placed under tension, either uniaxial or biaxial and is placed over the captive plunger and bonded or sandwiched in place while the tension is maintained.

In order to open the valve to allow flow in flow path 600, a valve plunger actuator is provided external to the cartridge which can cut the membrane and thus release the tension in the membrane sufficiently to relieve the pressure between the captive plunger 613 and the valve base layer 615. This device may be provided as a component of cartridge interfacing assembly 130 or the cartridge receptacle provided as part of centrifuge 110, thereby enabling robotic actuation when integrated fluidic processing cartridge 120 is loaded within centrifuge 110.

Figure 11E:
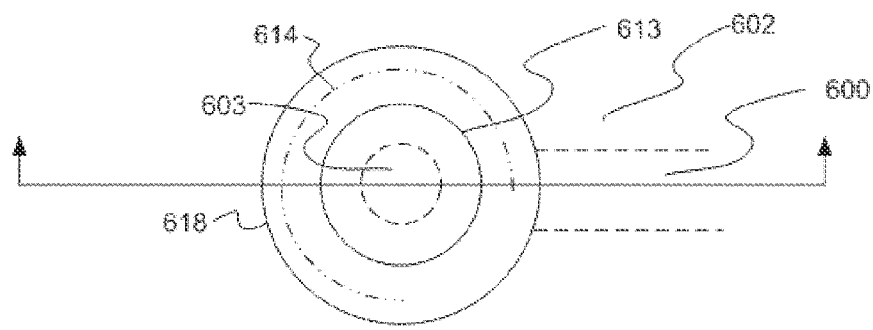
Figure 11F:
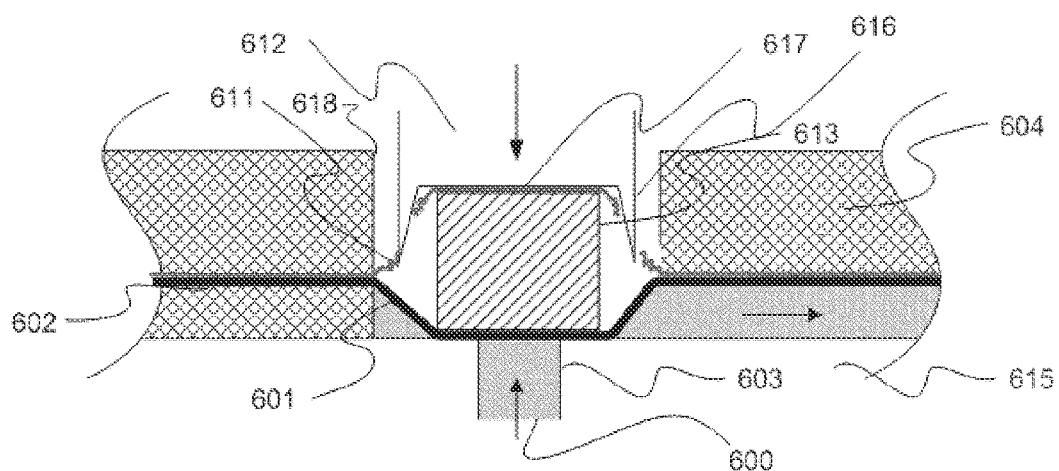

In one example embodiment, the valve plunger actuator 612 possesses a cutter 616 on the perimeter of the plunger actuator 612 which upon engagement with the membrane in the gap between the plunger 613 and the valve seat aperture 618 will cut the membrane upon the application of an adequate force as shown in FIG. 11F. Cutter 616 can extend around the full circumference of the captive plunger 613 to fully cut the membrane, or the cutter 616 may extend partially around the circumference to cut a portion of the membrane 611 as depicted in FIG. 11E by the cutting line 614. In the later embodiment the membrane tension may be partially released such that the plunger 613 remains captive but the pressure between the plunger 613 and the valve base 615 is relieved to an extent adequate to allow fluid flow between along fluid path 600.

Figure 11G:
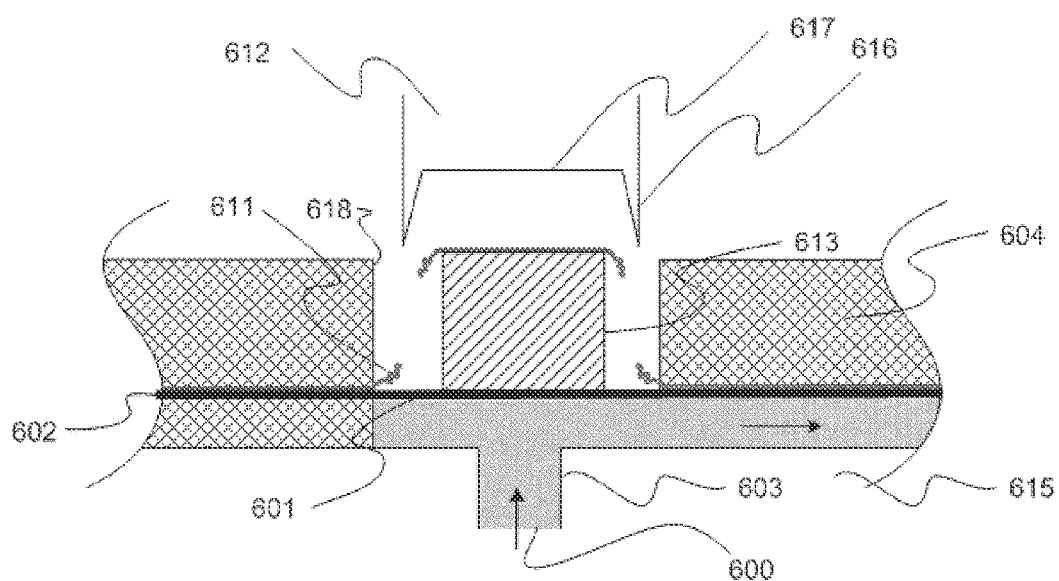

In an alternative embodiment the tension on membrane 611 is uniaxial and membrane 611 is cut only on that portion of the membrane under tension and in a direction transverse to the uniaxial membrane stress. Thus the valve plunger pressure is relieved but the plunger remains captive. Following relief of the valve plunger pressure in the manner described in various embodiments above, valve closure may be reactivated by application of the valve plunger actuator surface 617 to the captive valve plunger 613. Application of sufficient force to the valve plunger will re-engage captive plunger 613 with the diaphragm and valve base and reseal the port 603 as shown in FIG. 11F. Retraction of the plunger relieves the valve pressure and allows flow to occur in path 600 as shown in FIG. 11G.

Figure 11H:
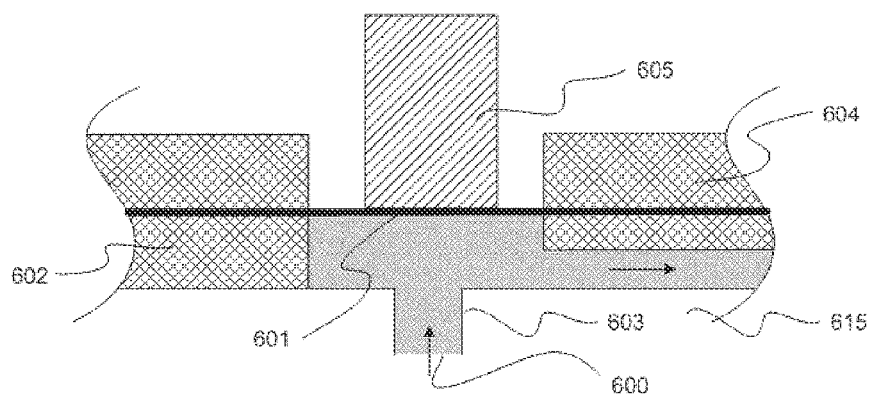
Figure 11I:
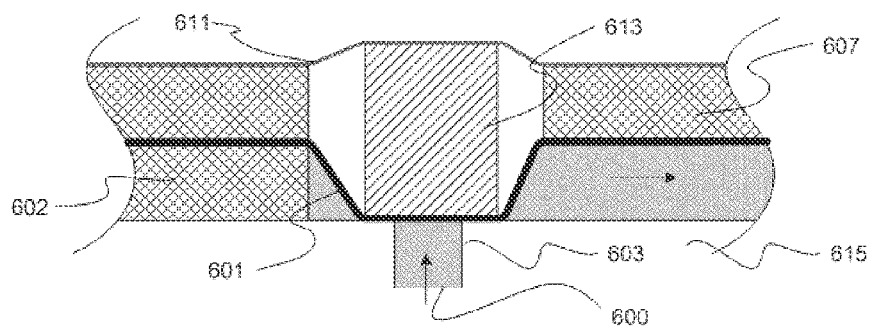

FIGS. 11H and 11I illustrate two alternative implementations of the diaphragm valve. In FIG. 11. H, the lateral microfluidic channel does not extend over the full height of the microfluidic layer. In FIG. 11I, the second membrane is bonded to the top layer 607, instead of joined to the first membrane.

In the embodiment shown in FIG. 10, an example valve membrane 601 thickness is between 0.025-0.25 mm, preferably 0.075 to 0.125 mm and an example fluid path 600 height is 0.025-0.5 mm, preferably 0.1-0.25 mm, and an example width is 0.1-4 mm. An example valve seat aperture 618 diameter is 2-8 mm, preferably 3-6 mm, and an example port 603 diameter is 0.1-3 mm, preferably 1-2 mm. An example membrane 611 is an aluminum foil of thickness between 0.025-0.2 mm.

Examples of Ports

Example integrated fluidic processing cartridge depicted in FIG. 10B possesses air displacement ports 741 and 743, which allow connection to an air displacement device to move fluids within integrated fluidic processing cartridge 700 as discussed previously. According to the example embodiment shown in FIG. 10B, the ports are engaged and disengaged with a removable air nozzle head 630 which is connected by a tube or other air path to the air displacement device. The air nozzle may be integrated into the cartridge interfacing assembly 130 such that the cartridge ports 741 and 743 may be engaged and disengaged when the cartridge interfacing assembly is engaged with the cartridge.

Figure 12A:
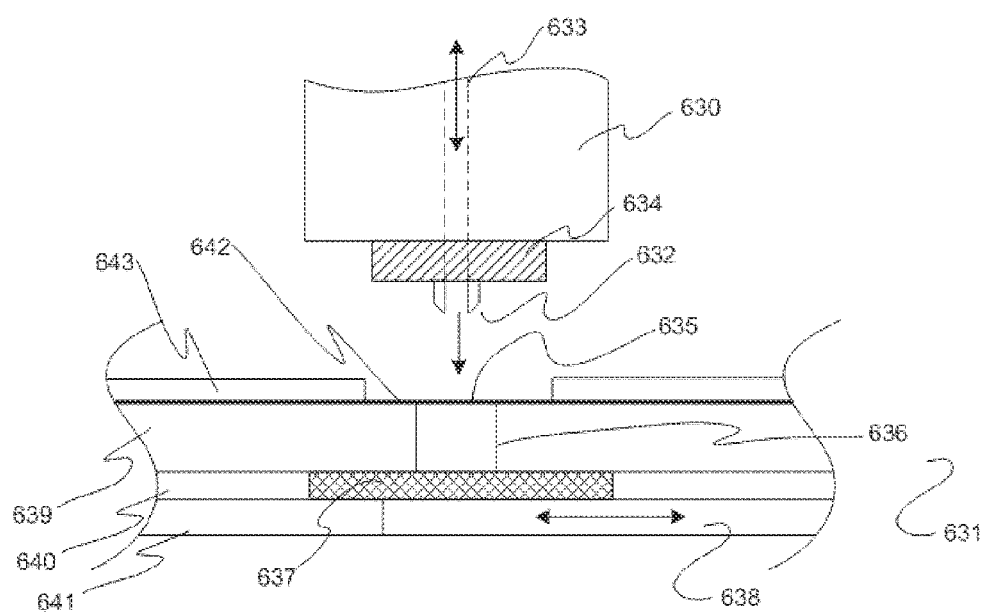
FIGS. 12A-B illustrate of an example embodiment of a port and associated air displacement mechanism, showing (A) cross-sectional and (B) overhead views.
Figure 12B:
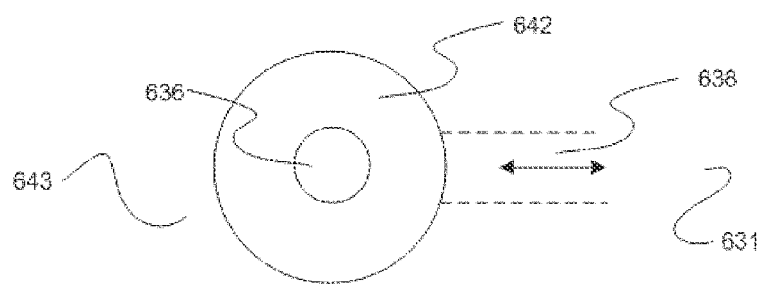

FIGS. 12 and 12B depicts an embodiment of such port 631 and an air nozzle head 630 which can be intermittently engaged and disengaged from the port. The nozzle head has an air path 633 connected to the air displacement device directly or via a rigid or flexible tube, and a nozzle 632. Optionally, nozzle 632 has a beveled edge and the air nozzle head has a face seal 634. The face seal 634 may be a rubber or other soft material which can obtain a seal with the face 642 of the port 631.

Port 631 includes hole 636 formed in laminate layer 639, where hole 636 is connected to air path 638 in layer 641. Optionally, a layer 640 between the layers possesses an air permeable membrane 637. Also, port hole 636 may optionally be sealed by membrane 635 which is bonded to layer 639 or sandwiched between the layer and an optional top layer 643.

Air nozzle head 630 is engaged with the port by punching seal 635 with the air nozzle 632 (or with another suitable punching device) and bringing air nozzle head face seal 634 into contact with face 642 of the port and applying the necessary pressure to seal the interface between the face of the seal 634 and the face 642 of the port. Air nozzle 632 aligns with and enters hole 636 during this action. Optionally, membrane 635 may be omitted such that the aforementioned punching action is not required. In such a case, air nozzle extension 632 from the body of the air nozzle head may optionally be omitted and the air path 633 brought into alignment with the hole 635 during engagement of the air nozzle head with the port.

In another embodiment the face seal 634 may be omitted, and the seal may be established between the face of the body of the air nozzle head and the face 642 of the port if sufficient force is applied and the materials used allows for a seal under these conditions. Membrane 635 may be a metal foil, e.g. aluminum foil, or a plastic membrane, e.g. polycarbonate, polyimide, PET, polypropylene, cyclic olefin or other material. Optional membrane 635 serves to provide a seal to the port prior to the first engagement with a connector nozzle, preventing the ingress of liquids or contaminants into the port. Optional air permeable membrane 637 serves to prevent passage of fluid from path 638 into the air nozzle head and optionally filters the air injected or evacuated by the air displacement operation. Thus integrated fluidic processing cartridge 120 is protected from airborne contaminants or interferents which may otherwise enter the cartridge via the port, and airborne microbial cells are prevented from entering or exiting the cartridge though the port. For this purpose, a membrane or other filter may be used for the element 637 which has a pore size of approximately 0.4 microns or less.

Examples of Air Vents

Air vents are provided to assist fluid flow into and from otherwise sealed passages and chambers at various locations in the cartridge. For example, in the embodiment of FIG. 5, by providing a vent 518 to atmosphere, atmospheric pressure can be attained in the supernatant chamber 506 so that a positive pressure differential promoting fluid flow can be obtained along conduit 511 by applying positive pressure via port 518 in centrifuge chamber 502 with the air displacement device. The structure of one example embodiment of an air vent is similar to the port of FIG. 12. When the optional pierceable membrane 635 is included, the vent is activated by piercing the membrane with a needle head equipped with a piercing needle to allow the passage of air.

Instrument/System

As described above, system 100, which may be provided as a benchtop instrument, contains a centrifuge having a motorized rotor. The motorized rotor is capable of speeds necessary to provide the centrifugal sedimentation force necessary for a given application or use, such as to sediment a wide range of target microbes in the fluid medium.

The sedimentation occurs in macrofluidic centrifugation chamber 200 of integrated fluidic processing cartridge 120 and those skilled in the art can determine the relationship between the rotor speed, rotor radius, cartridge geometry and centrifugation time necessary to sediment the particles (e.g. microbial cells or other cells) with known sedimentation coefficients. Sedimentation coefficients can be determined empirically by centrifuging target microbes in fluids of interest using commonly available benchtop centrifuges and known methods for measuring recovery.

The centrifuge may be of the fixed angle type or the swinging bucket type and centrifuge parameters are adjusted accordingly.

Figure 13A:
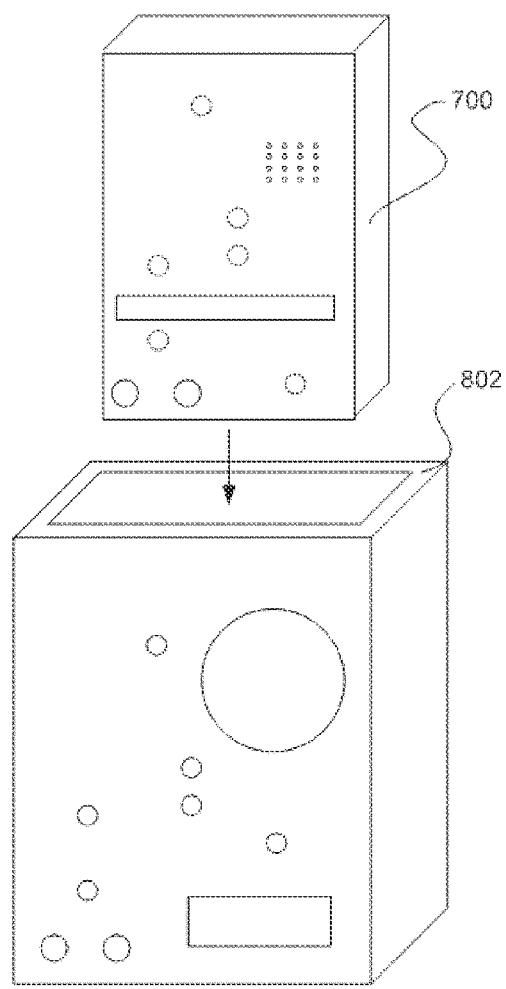
FIG. 13A illustrates the insertion of an integrated fluidic processing cartridge into a receptacle.
Figure 13B:
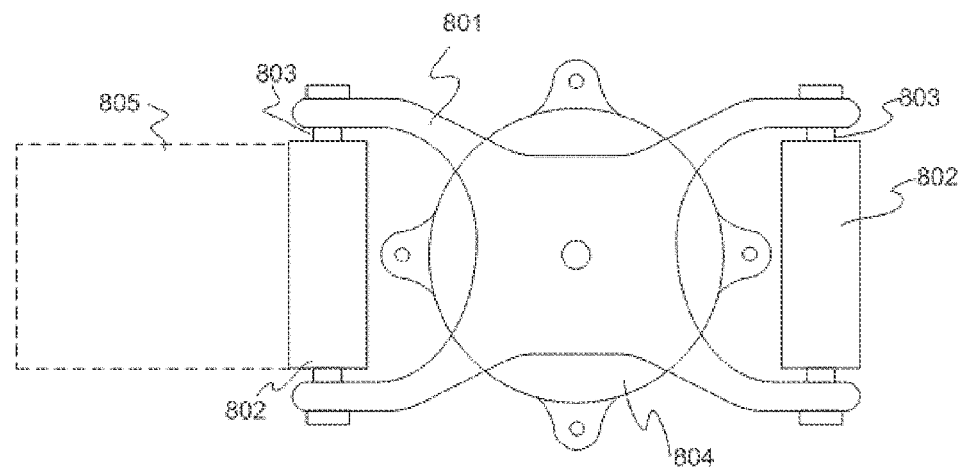
FIGS. 13B and 13C illustrate a hanging bucket centrifuge according to an example embodiment.
Figure 13C:
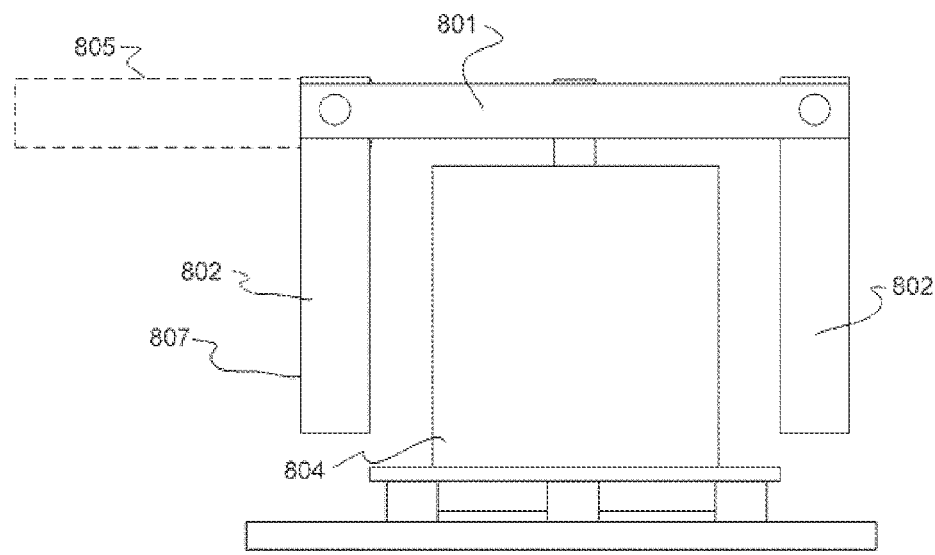

An example embodiment of the centrifuge is shown in FIG. 13B in plan view and in FIG. 13C in side view. The embodiment in FIGS. 13B and C depicts a swinging bucket centrifuge with rotor 801, two cartridge receptacles 802 which swing on hinge pins 803, and drive motor and shaft assembly 804. The cartridge described previously is placed in the receptacle and subjected to centrifugation at the appropriate steps in the centrifugal separation and washing process described in FIG. 3. Under full speed centrifugal rotation the cartridge receptacle will swing to occupy the horizontal position 805 due to centrifugal forces acting on the receptacle 802 and revert to the vertical orientation 807 when rotation stops.

An example embodiment of a cartridge receptacle which accepts the integrated fluidic processing cartridge, such as the cartridge embodiment 700 depicted in FIG. 10, and provides the necessary interface elements for cartridge 700 is illustrated in FIG. 13A. In this example embodiment the cartridge is inserted from the top as shown and is secured in the receptacle that it is engaged with interface elements on the receptacle which may include electrical contacts, fluidic ports, valve actuators, and optical module components. These interface elements in turn engage with mating elements on the cartridge interfacing assembly 120 when the cartridge interfacing assembly engages with the cartridge receptacle so that the cartridge interfacing assembly can controllably actuate or activate the various elements as required. Alternatively, for some or all interface elements, access holes and areas may be provided to allow those interface elements present on the cartridge interfacing assembly to interface directly with the cartridge. In some embodiments interface elements on the cartridge receptacle are engaged with the cartridge only after the cartridge interfacing assembly engages with the cartridge receptacle. Thus the cartridge interfacing assembly 130, controlled by the central control and processing unit 140, either directly, or indirectly through intermediate interface elements on the cartridge receptacle, acts on the cartridge to perform the various functional operations described in relation to the various embodiments described and anticipated herein.

Figure 14A:
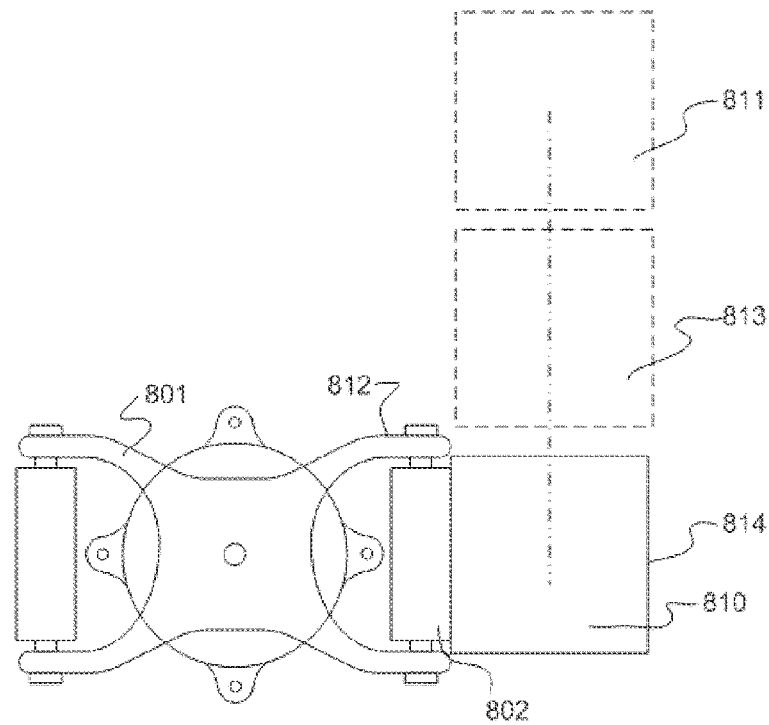
FIGS. 14A and 14B illustrate an example embodiment involving the engagement of a cartridge interfacing assembly with an integrated fluidic processing cartridge housed in a rotor.
Figure 14B:
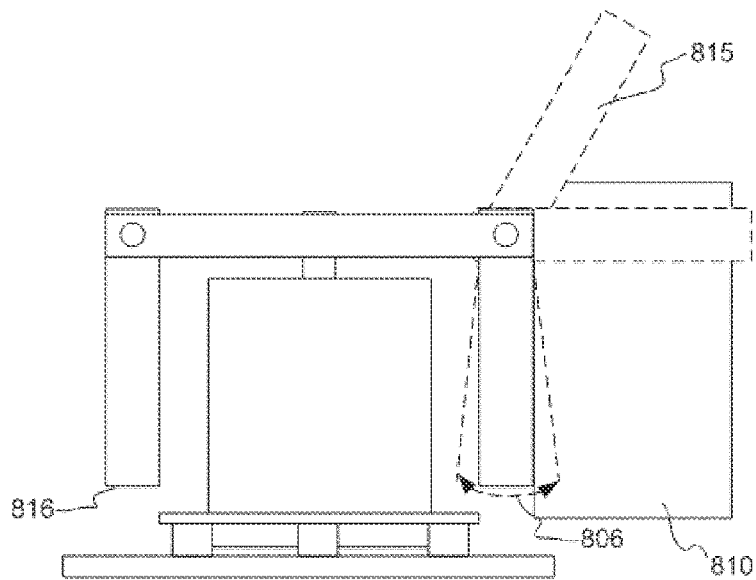

As shown schematically in FIGS. 14A and 14B, the cartridge interfacing assembly, here depicted schematically as 810, can be brought into position 814 and engaged with the face of cartridge receptacle 810. FIG. 14A provides a plan view of the motorized rotor 801 and cartridge interfacing assembly 810 and depicts a position 811 to which the cartridge interfacing assembly 810 is retracted out of the path of the rotor and swinging bucket during centrifugation. When the centrifugation ceases, the centrifuge rotor is brought to rotational position 812 such that the cartridge interfacing assembly 810 can be brought into position to engage with the cartridge and cartridge receptacle. This rotor positioning action may be performed by the centrifuge drive motor either directly in conjunction with a position sensor, or by provision of a braking mechanism which stops the rotating rotor at a predetermined position. Alternatively a motorized positioning wheel may engage with the rotor or rotor shaft after centrifugation has stopped and drive the rotor to the required position. Position sensors may be provided to assist rotor positioning.

The cartridge interfacing assembly 810 must move into position and engage the cartridge receptacle and optionally the cartridge directly for various actions. The cartridge interfacing assembly 130 may be fixed to a translation stage and/or a rotational stage which give it the necessary translational and/or rotational motions to move into position lateral to the face of the cartridge and to engage the cartridge receptacle. The cartridge interfacing assembly 130 may engage the receptacle by latching it and holding it rigidly or semi-rigidly, or it may come into contact with it and engage it with a fixed stop or bracket which will prevent the swinging action and lock the cartridge receptacle in place. The cartridge interfacing assembly contains the various interface elements necessary to perform the various actions necessary for the processes described herein with respect to the various embodiments of the integrated fluidic processing cartridge. This may include electrical connectors or contacts, actuators, fluidic connectors, pumps, air displacement devices, optical devices and other devices which enable the required electrical, mechanical, fluidic and optical operations to be performed. Some examples of these devices and components and interface elements supplied on the cartridge receptacle are described below. These are intended to be representative of typical devices and elements required to perform the functions described herein with respect to various embodiments are provided below but is not exhaustive nor complete. Additional and alternative devices, components and elements may be determined by those skilled in the art.

A multi contact electrical connector, or multiple electrical connectors, may be employed to provide electrical power to the various cartridge terminals and to transmit and/or receive electrical signals from some terminals to power the heating elements for reverse transcription and PCR, to detect temperatures by means described previously, and to provide electrical power to the electrical lysing elements. The electrical connection may be made directly between a multi contact connector on the cartridge interfacing assembly 130 and the cartridge terminals via an opening in the receptacle when the cartridge interfacing assembly 130 is engaged with the cartridge. Alternatively an electrical connection can be made between the cartridge terminals and a multi contact connector in the receptacle and upon engagement of the cartridge interfacing assembly 130 with the receptacle, a connector on the cartridge interfacing assembly 130 makes electrical contact with the respective contacts or connector on the cartridge receptacle. Such electrical connections may be, for example, pogo pins, spring clip connectors, contact probes, card connectors, PAD connectors, leaf spring contacts/connectors, compression connectors, cylindrical spring contacts, spring finger contacts, or other such electrical contacts known to those skilled in the art.

The cartridge interfacing assembly 130 may include one or more air nozzle heads 630 which engage directly with the cartridge ports 631 on the cartridge as described in relation to the embodiment in FIG. 12 or as may be required for other equivalent embodiments. The cartridge interfacing assembly 130 either contains an air displacement device or is connected by way of a flexible tube to an air displacement device mounted in another fixed location in the instrument. The air displacement device may be a syringe pump, peristaltic pump. Alternatively the receptacle may contain an air nozzle head and the cartridge interfacing assembly 130 engages with this nozzle head to engage it with the cartridge and to effect the required air displacements. In some embodiments multiple air nozzle heads may be present to enable air displacement in additional cartridge ports. A vent needle can similarly be present on the cartridge interfacing assembly 130 and be directly engaged with the cartridge or alternately be mounted in the cartridge receptacle and engaged with the cartridge upon actuation by the cartridge interfacing assembly 130.

Valve Actuators

As depicted in FIG. 11A, the example valve actuation mechanism described previously requires an actuator plunger to apply pressure directly to the diaphragm 601 or to apply pressure to in intermediate captive plunger (e.g. 613) in the cartridge assembly. This actuator plunger is in some embodiments mounted within the cartridge receptacle in a manner which allows it to be engaged and actuated by the cartridge interfacing assembly 130 to effect required cartridge valve actions as well as such actions as may be required to allow the cartridge to be inserted into the cartridge receptacle. FIG. 15 provides example embodiments of cartridge actuation mechanisms with schematic cut-out views of the cartridge and cartridge receptacle wall.

Figure 15A:
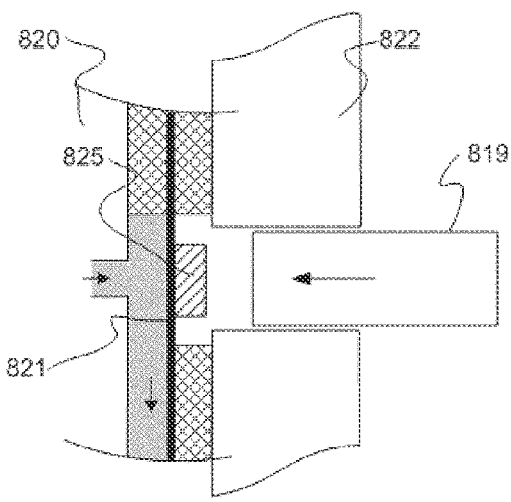
FIGS. 15A-E illustrate alternative example embodiments for actuating a valve plunger.
Figure 15B:
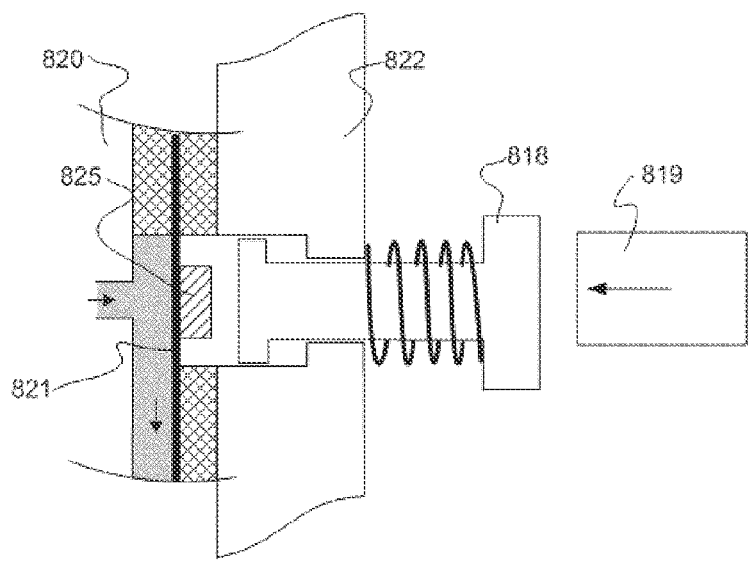
Figure 15C:
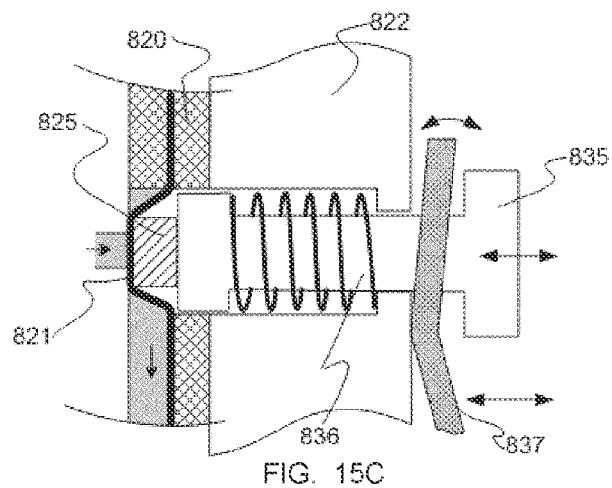
Figure 15D:
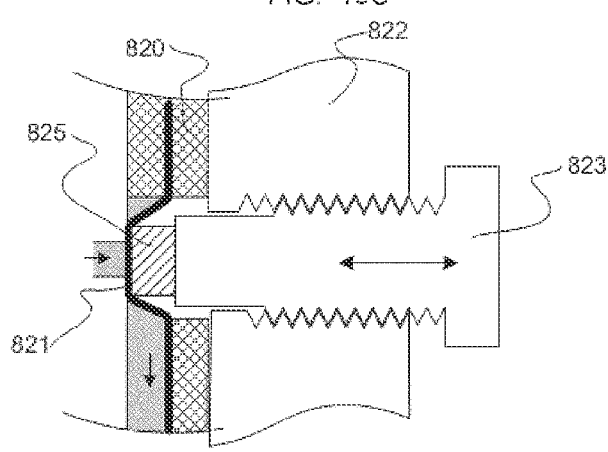
Figure 15E:
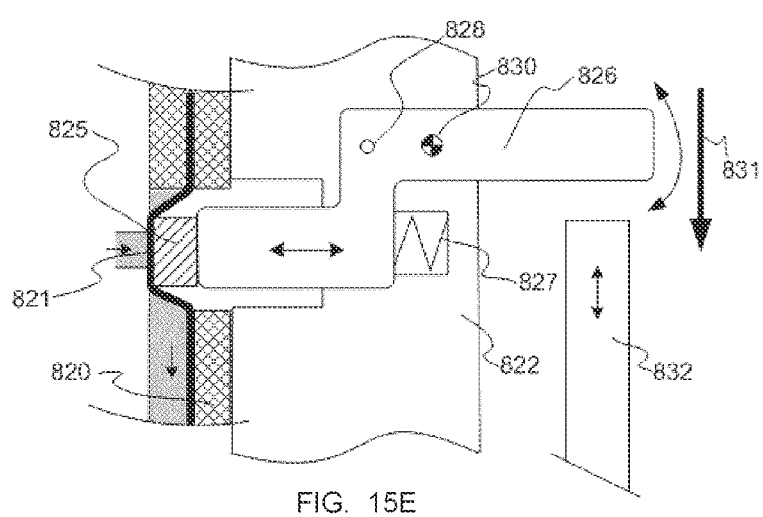

In FIGS. 15A-E, a schematic cross section view of a valve in cartridge 820 is shown in relation example embodiments of actuator pins mounted in cartridge receptacle 822. The valve is in open state FIG. 15A-B show the valve in open state and FIG. 15C-E show the valve in closed state.

In FIG. 15A a hole is provided in the wall 822 of the cartridge receptacle in alignment with the valve which provides access for a pin 819 mounted on an actuator on the cartridge interfacing assembly 130 (not shown) to apply force to a captured plunger 825 on the cartridge thereby closing the valve as described previously with respect to FIG. 11. Alternatively, in some embodiments, the captured plunger is omitted and pin 819 may contact the valve diaphragm 821 directly, thereby closing the valve. Retraction of the actuator plunger relieves pressure from the diaphragm and fluid may be flowed with the application of an appropriate pressure differential along the flow path by the air displacement device connected to a cartridge port as described above.

FIG. 15B depicts an example of a pin 818 captive in the wall 822 of the receptacle and optionally equipped with a spring to retract the pin. Thus the cartridge may be easily inserted into the receptacle without interference and the valve will be in an open position when the actuator pin 819 is not acting on it. The valve is closed when actuator pin 819, or some other similar element, applies a compressive force axial to the pin 818 such that it is brought into contact and applies pressure to the captive plunger 825 or optionally the valve diaphragm 821 directly.

FIG. 15C shows a pin 835 captive in the wall of the cartridge receptacle and optionally equipped with a pre-compressed spring 836 which acts on the pin 835 to close the valve by applying compressive force to captive plunger 825, or alternatively directly to the valve diaphragm 821. The spring pre-compression should be sufficient to hold the valve closed under all conditions under which that is required, including, optionally, during centrifugation of the integrated fluidic processing cartridge and receptacle. Thus, under no external actuation the valve will be latched closed. External actuation is provided by an actuator on the cartridge interfacing assembly 130 to retract the pin 835 and release the compressive force on the diaphragm valve to open the valve and allow fluid to flow. Such actuation may also optionally retract the pin 835 to allow clearance for inserting the cartridge into the receptacle. Such actuation must retract the pin 835 against the spring force provided by spring 836 and may be accomplished in a number of ways. The cartridge interfacing assembly 130 may include a gripping mechanism to grasp the head of the pin 835 and pull the pin axially and in a direction away from the cartridge. Alternatively, a lever mechanism 837 may bear against the surface of the cartridge receptacle and the underside of the head of the pin which when actuated may lift the head of the pin and thereby retract the pin for the above purposes. This embodiment allows the valve to be latched closed such that closure is maintained when the cartridge interfacing assembly is disengaged from the cartridge receptacle. Thus, during centrifugation, fluid will be prevented from flowing through such actuated valves. Note that the spring force must be sufficient to prevent leakage through the valve under the substantial fluidic pressure which may occur in the valve during high speed centrifugation In FIG. 15D, the receptacle wall contains a threaded hole or threaded insert which contains a screw 823 whose end face may be brought into contact with the valve diaphragm 821 directly or into contact with a captive plunger 825 on the cartridge as shown. Upon the application of a sufficient amount of pressure the diaphragm valve will be closed. The screw 823 may be retracted to open the valve and to provide clearance for insertion of the cartridge. Optionally a contact pin may be provided as a separate component and mounted in the receptacle wall intermediate to the valve and screw and optionally keyed in a manner so as to prevent rotation of the pin as it is engaged and actuated by the screw 823. This embodiment also allows the valve to be latched closed such that closure is maintained when the cartridge interfacing assembly 130 is disengaged from the cartridge receptacle. Thus during centrifugation fluid will be prevented from flowing through such actuated valves. Note that the valve actuation force must be sufficient to prevent leakage through the valve under the substantial fluidic pressure which may occur in the valve during high speed centrifugation.

FIG. 15E provides another example embodiment where a lever 826 with hinge pin 828 is mounted in or on the receptacle wall. The lever 826 is optionally equipped with a pre-compressed spring 827 which applies a sufficient force to the lever such that it maintains contact with the captive plunger 821 and closes the valve. Note that in some alternate embodiments the plunger may optionally be equipped with a retraction spring which acts to release of pressure from the valve force.

The valve may be acted on by an actuator 832 on the cartridge interfacing assembly to cause counterclockwise rotation of the lever 826. In doing so the actuator overcomes the spring force and releases the force applied to the plunger 825. The pressure is thus released from the valve to allow fluid flow. When the lever is released by the actuator the lever assumes the valve closing position assisted by spring 827. This force must sufficient to maintain leak free closure of the valve at rest and optionally during the operation of the centrifuge. In another embodiment the center of mass 830 of the lever 826 is preferentially positioned such that under centrifugal rotation for which centrifugal forces are in the direction 831, the centrifugal force experienced by the lever creates a compressive reactive force on the plunger 825 acting to further increase the force applied to the valve. The additional valve closure force produced in this manner may provide the assistance required to seal the valve even under the high fluidic pressures which may be experienced at high centrifugal speeds. For this embodiment the spring 827 closure force need only be sufficient for leak free closure of the valve up to centrifugal speeds where the centrifugal force exceeds the spring force.

In all of the embodiments depicted in FIG. 15, the surface which bears on the captive plunger on the cartridge may be optionally equipped with a cutter 616 as depicted in FIG. 11. Actuators which perform the actuations described may take one or more of many different forms including solenoids, hydraulically actuated pistons, servos, DC motors, and stepper motors. Linear actuators may incorporate the actuator pins 819 and 832 directly, or they may act via an intermediary mechanism which includes actuator pins 819 and 832, or lever 837 or they may act through an intermediary mechanism which converts linear motion to rotational motion as for actuator screw 823. Rotational actuators such as servos, DC motors and stepper motors for example, may act directly on the actuator screw 823, incorporating an engagement mechanism which allows the actuator screw 823 to be engaged, rotated as required, and disengaged. Such rotational actuators may also be used for linear actuation of actuator pins 819 and levers 826 and 837 via an intermediary mechanism such as cams, levers or other mechanisms which convert rotational motion to linear motion.

Mixing

Example embodiments for mixing fluids in the chambers in the integrated fluidic processing cartridge are provided. Cyclic cartridge inversion is an effective mixing method whereby the cartridge is rotated from an upright position to a fully inverted position or a partially inverted position, and then back to the initial upright position in one inversion mixing cycle. The swinging bucket receptacle allows this action by extending the swing path to an inverted position such as depicted by position 815 in FIGS. 15A and B. For example, the cartridge interfacing assembly 130 can be used to actuate this motion by taking a position 813 to the side of the cartridge receptacle and engaging the receptacle while remaining free of the swing path. In one embodiment the cyclic swing action can be actuated using an arm which engages with the cartridge receptacle and moves the receptacle through its range of motion by the way of a DC motor, stepper motor, solenoid or servo. Alternately a gear interface may be provided between a rotary drive device on the cartridge interfacing assembly 130 and the receptacle.

Figure 16:
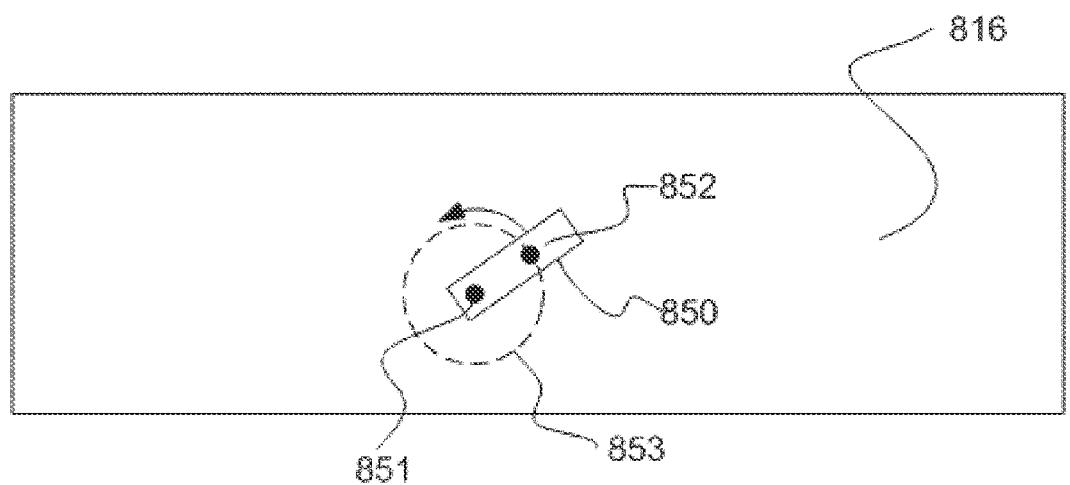
FIG. 16 illustrates an example implementation of a mechanism for vortexing the integrated fluidic processing cartridge via orbital motion.

An embodiment which allows for fluid mixing (e.g. fluid agitation) in the cartridge by vortexing of the cartridge is now described. For example, the vortexing action may be an orbital displacement of the base of the cartridge (816 in FIG. 14B) in the plane of the base. For example, the orbit may be 5 mm and the orbiting speed may be 1000 rpm. This action can be performed by engaging the bottom of the cartridge receptacle with a motor driven rotary element on the cartridge interfacing assembly. The rotary element may be a cam which contacts a feature on the bottom of the cartridge receptacle, or a disc with an offset pin engaged with the bottom of the cartridge. For example, FIG. 16 shows a bottom view of the cartridge receptacle 802 with rotary element 850. The eccentric engagement point 852 between rotary element 850 and receptacle 816 is offset from the center of rotation 851 of the rotary element 850 such that as the rotary element 850 rotates, the cartridge receptacle bottom 816 follows the circular orbit 853. Thus for a 5 mm diameter radius the engagement point is offset 2.5 mm from the center of rotation of the rotary element. The engagement between the rotary element and the cartridge receptacle may occur via a bushing, a bearing or otherwise rotationally free junction. Alternately an eccentrically driven rotary element can be brought into contact with the bottom of the cartridge receptacle and by friction or another means of engagement so that the bottom of the cartridge may be rotated through the desired orbit. While the bottom of the cartridge is orbited in this way, the top of the cartridge receptacle must possess sufficient freedom to allow this motion to occur. The swinging motion (shown as 806 in FIG. 14B) of the receptacle 802 about the hinge 803 provides freedom for the component of orbital motion in the direction of the rotor radius. The complementary component of the orbital motion is in the rotor circumferential direction and may be accommodated by providing a hinge (803 in FIG. 13A) which allows such motion. For example, the swinging receptacle hinges 803 may be engaged in vertical slots on the respective side walls of the receptacle allowing the require rocking motion of the cartridge which conforms to the circumferential component of the orbital displacement at the cartridge base. Alternatively the vortexing motion imparted to the bottom of the cartridge receptacle may be linear in the radial direction causing an alternating swinging action 806 which conforms to the swinging motion provided by the cartridge receptacle hinge. Such action may be produced by the rotating element 850 in which the lateral component of the motion is released by a sliding mechanism in the engagement mechanism with the cartridge receptacle or within the rotary element itself. Alternatively this may be produced by some other rotational to linear motion mechanism such as a cam or lever, or by actuation with a linear actuator.

Example of Cartridge Receptacle and Cartridge Interfacing Assembly

Figure 18A:
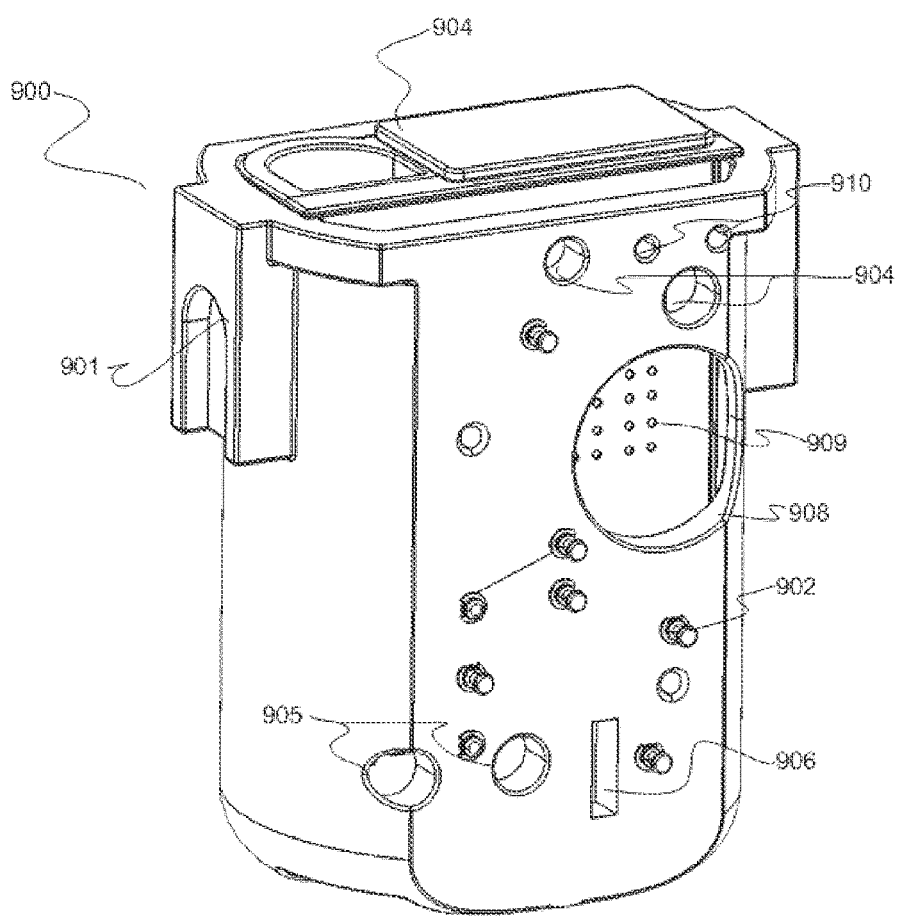
FIG. 18A illustrates an example implementation of an integrated fluidic processing cartridge supported in a receptacle.
Figure 18B:
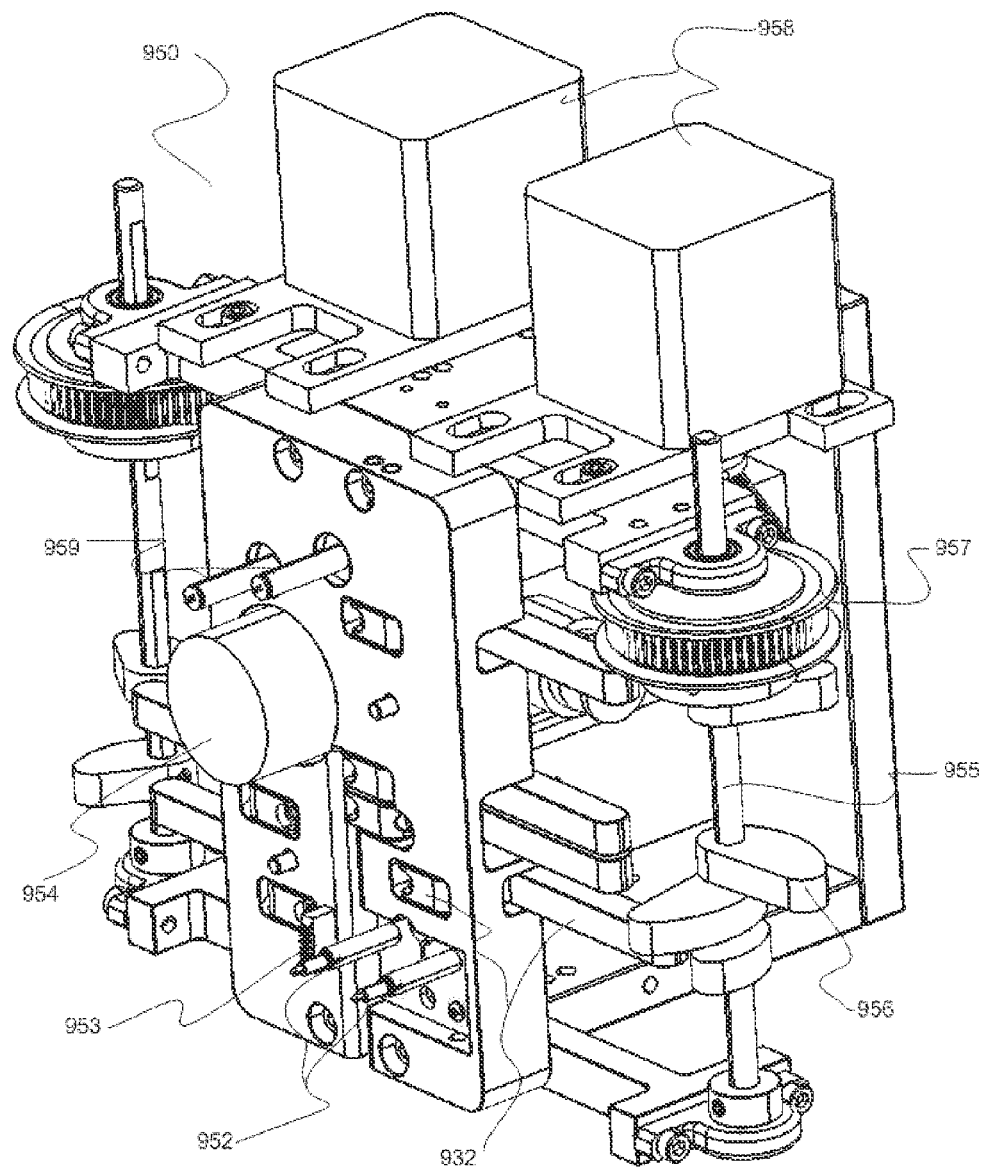
FIGS. 18B-C illustrate an example implementation of a cartridge interfacing assembly, where
Figure 18C:
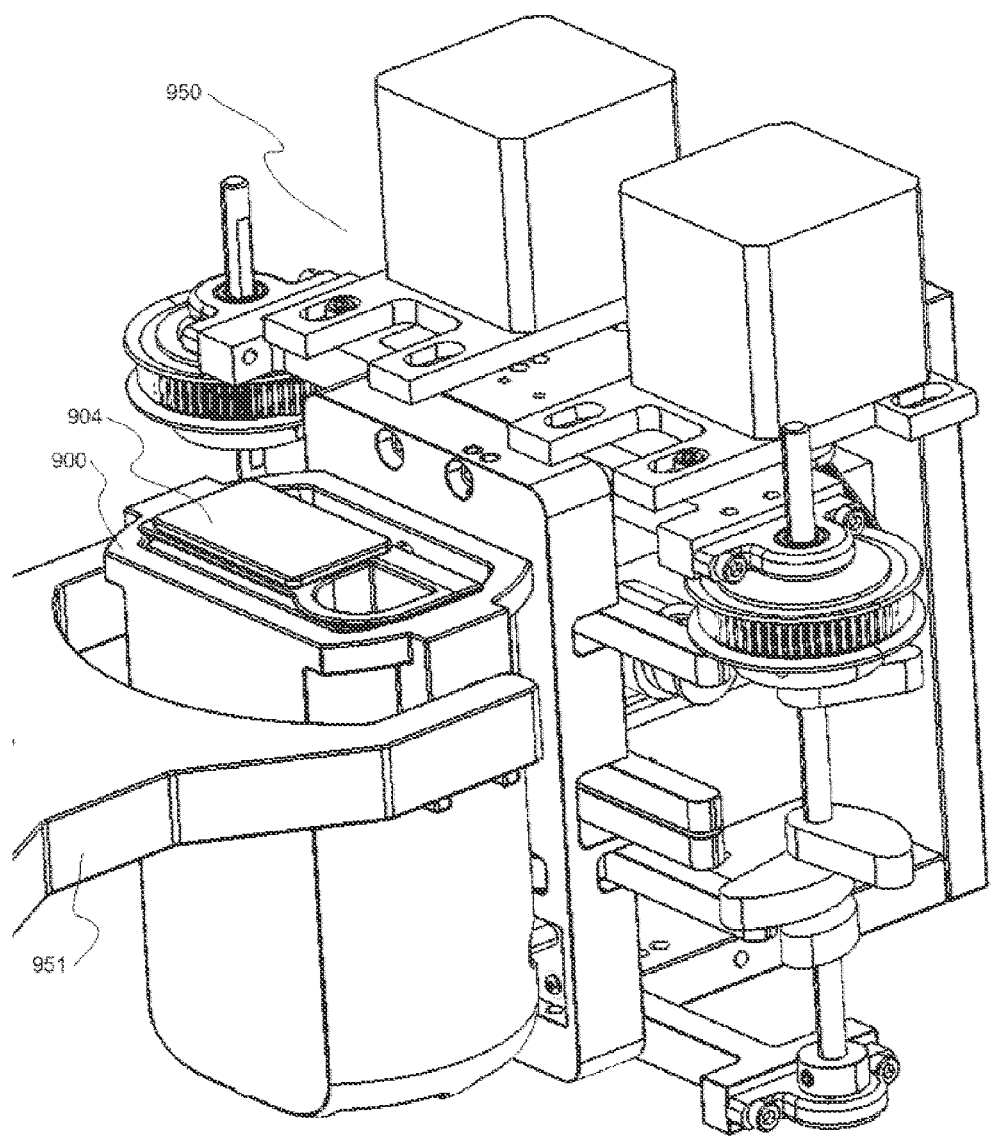

An example embodiment of a cartridge receptacle 900 is provided in FIG. 18A FIG. 18B provides an example embodiment of a cartridge interfacing assembly 950 which, as depicted in FIG. 18C, is able to be translated into position by a robotically controlled translation stage (not shown) and engage with the cartridge receptacle when the motorized rotor 951 has come to rest in the rotational position which conforms with the alignment requirements of the engagement of the cartridge interfacing assembly, and the cartridge receptacle assumes a vertical position. The cartridge interfacing assembly, when translated into position to engage the cartridge receptacle, may press against the cartridge receptacle to engage the cartridge receptacle with stops on the opposing side (not shown) so that the cartridge receptacle is restrained from swinging away from the cartridge interfacing assembly and is held firmly as the cartridge interfacing assembly engages with the cartridge receptacle. Alternatively the cartridge interfacing assembly may include a mechanism which is able to secure the cartridge receptacle and hold it in position for engagement.

The example cartridge receptacle 900 is a swinging receptacle with hinge receptacles 901 which engage with the rotor pins. The sample cartridge 904 is shown inserted into the cartridge receptacle. The receptacle further includes actuator pins 902 which are held captive in the receptacle wall shown (in cross-section) as 935 in FIG. 17A and which are equipped with a pre-compressed spring 930 and a head 931 which protrudes from the surface of the cartridge receptacle. This actuator pin embodiment is the latched closed embodiment of FIG. 15C which holds all valves closed by means of the spring force when the cartridge interfacing assembly is not engaged and when the actuator lever is not actuated. The protruding head 931 allows engagement with a lever 932 hinged at 933 and mounted in the front face 937 of the cartridge interfacing assembly 950.

Figure 17A:
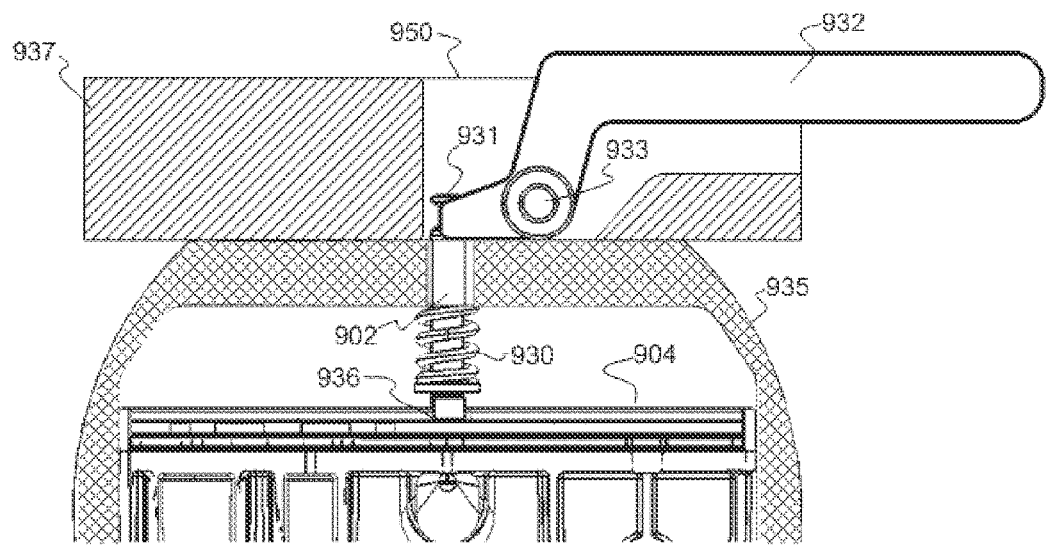
FIG. 17A-C illustrate example valve latching mechanisms.
Figure 17B:
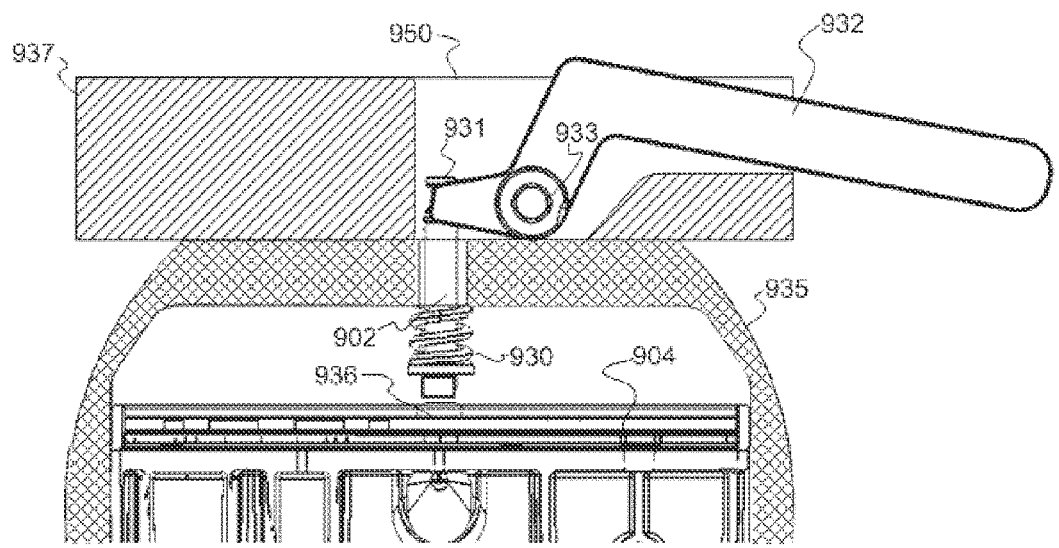
Figure 17C:
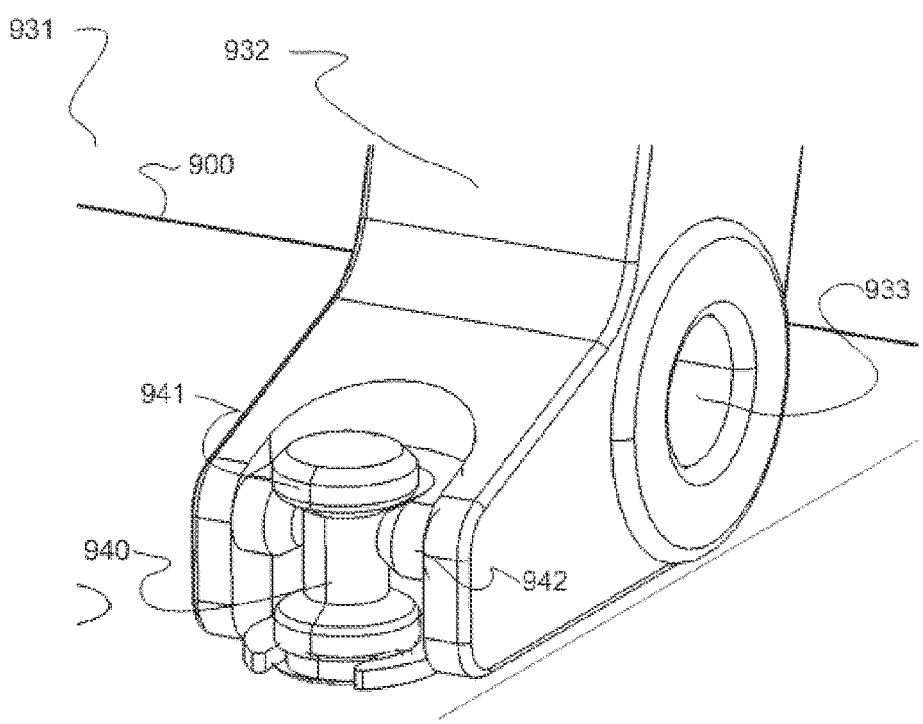

FIG. 17A shows the cartridge interfacing assembly 950 in the engaged position with the cartridge receptacle 900 and where the lever has engaged with the actuator pin head 931 protruding from the cartridge receptacle. In the lever position of FIG. 17A the actuator pin remains in unactuated position and the actuator pin 902 is acted upon solely by the pre-compressed spring 930 and against the valve 936 and the valve diaphragm is in a closed position. The lever has a notched feature which allows it to engage with the protruding head 931 as the cartridge interfacing assembly is brought into close proximity to the cartridge receptacle. For example, the lever may be rotated clockwise into the position of FIG. 17A as the cartridge interfacing assembly approaches the cartridge receptacle such that the notched feature 942 engages with the narrowed region 940 of protruding head 931 as shown in FIG. 17C. FIG. 17B shows the lever in an actuated position which opens valve 936 by clockwise rotation of lever 932 about hinge 933 so that the lever notch 942 contacts the widened top portion 941 of the actuator pin head 931 so that actuator pin 902 is raised thus releasing the pressure on the valve 936.

The cartridge receptacle further includes access holes 904 for air nozzle heads 959 to engage directly to cartridge ports 741 and 743 (of FIG. 10). The air nozzle pins are optionally spring mounted on cartridge interfacing assembly to allow the sealing face of air nozzles 959 to contact the cartridge port and apply a compressive force between said face and port. The spring stiffness and an optional spring perforce may be prescribed which will ensure that sufficient force is applied so that a seal can be repeatedly be made which will withstand the pressure applied to the port during fluid transfer. Access holes 905 are provided for the electrical lysing contact pins 952 to make electrical contact with the cartridge electrical lysing terminals 747. Such electrical contact pins may be spring loaded pogo pins to ensure reliable contact. The array of electrical contacts 906 are provided on the cartridge receptacle surface for connection to a mating array of terminals or pins 953 on the cartridge interfacing assembly. The contacts 906 are connected electrically to terminals within the cartridge receptacle which are spring loaded or otherwise configured so that, upon insertion of the cartridge into the cartridge receptacle, they make electrical contact with the contacts 746 on the sample cartridge. This electrical connection provides the means by which the cartridge heaters are powered and monitored. The cartridge also has access holes 910 which allow optional vent piercing pins on cartridge interfacing assembly 950 to reach and pierce an optional vent membrane seal on the cartridge vents upon engagement of the cartridge interfacing assembly. Cartridge receptacle 900 also has an access hole 908 to allow optical access to the optical windows of the PCR chamber array 909 by the imager 954 or other optical module mounted on cartridge interfacing assembly 950.

Cartridge interfacing assembly 950 is shown with a camshaft 955 equipped with multiple individual cams 956, each aligned with one of the valve levers 932. The camshaft shown is driven by belt and pulley 957 and a stepper motor 958 which can controllably position the camshaft at rotational positions for which the cam lobes come into contact with the respective lever arm 932 and to actuate the lever so as to open the valve as described above. Each cam may have one or more lobes to enable activation of its respective lever in one or more rotational positions respectively. In this way valves can be either actuated individually or In groups. For example, with reference to the embodiment of FIG. 5, during extraction of supernatant from the centrifuge chamber, valves 509, 512, and 517 must remain closed and supernatant valve 513 opened as positive gauge pressure is applied to centrifuge chamber port 518. The remaining valves in the microfluidic backplane may optionally remain closed during this operation. Thus a single cam on camshaft 955 associated with the supernatant valve on the cartridge may actuate the respective lever on the cartridge interfacing assembly to open said valve as air pressure is delivered to the centrifuge chamber port while all other valves remain unactuated and closed. In another operation, for example, with reference to FIG. 8, valves 517, 565, 566, 567 and 572 must be open to draw fluid from lysate chamber 562 to the PCR array 563 by air evacuated from port 571. Thus, cam lobes corresponding to all of these valves, if present on the cartridge embodiment, must contact the respective valve levers to open all of these valves at the same rotational position so as to effect simultaneous opening of the valves. Individual cams may therefore have one or more lobes to allow actuation of the respective valve alone or together with other valves as required by the cartridge process. In some circumstances it may be necessary to have more than one camshaft to accommodate complex valve processes.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

The invention claimed is:

1. A system for performing centrifugal separation, said system comprising:
a fluidic cartridge comprising a valve; and
a centrifugation device comprising:
 a rotor; and
 a receptacle pivotally connected to said rotor, said receptacle being configured to receive said fluidic cartridge;
said receptacle comprising a mechanical valve latching mechanism capable of mechanically latching said valve in a closed state during centrifugation of said fluidic cartridge.

2. The system according to claim 1 wherein said valve and said mechanical valve latching mechanism are configured such that leakage of fluid through said valve is prevented when said valve is mechanically latched in the closed state during centrifugation despite fluidic pressures generated during centrifugation.

3. The system according to claim 1 wherein said mechanical valve latching mechanism is configured such that during centrifugation, a centrifugal force applied to said mechanical valve latching mechanism results in a compressive force applied to said valve.

4. The system according to claim 1 wherein said mechanical valve latching mechanism comprises a retractable pin that is held captive in a wall of said receptacle, said pin being biased against said valve when said fluidic cartridge resides within said receptacle.

5. The system according to claim 1 wherein said mechanical valve latching mechanism comprises a spring-loaded assembly configured to hold said valve closed by a spring force when said fluidic cartridge resides within said receptacle.

6. The system according to claim 1 wherein said mechanical valve latching mechanism comprises a ratchet device capable of locking said valve in the closed state when said fluidic cartridge resides within said receptacle, wherein said ratchet device being releasable to open said valve.

7. The system according to claim 1 wherein said mechanical valve latching mechanism comprises a screw that is received within a threaded aperture in said receptacle, wherein a position of an end face of said screw, relative to said receptacle, is adjustable to bring said valve into the closed state when said fluidic cartridge resides within said receptacle.

8. The system according to claim 7 wherein said mechanical valve latching mechanism further comprises a contact pin mounted on said receptacle at a location intermediate to said valve and said screw, said contact pin being configured to be engaged and actuated by said screw during rotation of said screw for contacting and closing said valve.

9. The system according to claim 8 wherein said contact pin is keyed in a manner so as to prevent rotation thereof during engagement and actuation by said screw.

10. The system according to claim 1 wherein said valve and said mechanical valve latching mechanism are configured such that leakage of fluid through said valve is prevented when said valve is mechanically latched in the closed state during centrifugation with an applied centrifugal force between 1000 g and 15,000 g despite fluidic pressures generated during centrifugation.

11. The system according to claim 1 wherein said valve and said mechanical valve latching mechanism are configured such that leakage of fluid through said valve is prevented when said valve is mechanically latched in the closed state during centrifugation with an applied centrifugal force between 3000 g and 10,000 g despite fluidic pressures generated during centrifugation.

12. The system according to claim 1 wherein said valve and said mechanical valve latching mechanism are configured such that leakage of fluid through said valve is prevented when said valve is mechanically latched in the closed state during centrifugation with an applied centrifugal force between 2000 g and 12,000 g despite fluidic pressures generated during centrifugation.

13. The system according to claim 1 wherein said valve and said mechanical valve latching mechanism are configured such that leakage of fluid through said valve is prevented when said valve is mechanically latched in the closed state during centrifugation with an applied centrifugal force between 4000 g and 8000 g despite fluidic pressures generated during centrifugation.

14. A method of performing centrifugation, the method comprising:
providing a system according to claim 1, wherein the fluidic cartridge resides within said receptacle; and
controlling the centrifugation device to centrifuge the fluidic cartridge while the valve latching mechanism maintains the valve in the closed state.

15. The method according to claim 14 wherein the valve and the mechanical valve latching mechanism are configured such that leakage of a fluid through the valve is prevented when the valve is mechanically latched in the closed state during centrifugation despite fluidic pressures generated during centrifugation.

16. The method according to claim 15 wherein the mechanical valve latching mechanism is configured such that during centrifugation, a centrifugal force applied to the mechanical valve latching mechanism results in a compressive force applied to the valve.

17. A system for performing centrifugal separation and fluidic processing, said system comprising:

a fluidic processing cartridge comprising a valve;
a centrifugation device comprising:
- a rotor; and
- a receptacle pivotally connected to said rotor, said receptacle being configured to receive said fluidic processing cartridge, said receptacle comprising a mechanical valve latching mechanism; and a cartridge interfacing assembly capable of engaging with said receptacle and actuating said valve latching mechanism to open said valve when said rotor is at rest and said fluidic processing cartridge resides within said receptacle;

said valve latching mechanism being configured to mechanically latch said valve in a closed state when said fluidic processing cartridge resides within said receptacle and said cartridge interfacing assembly is disengaged from said receptacle; and said mechanical valve latching mechanism comprising a pin that is held captive in a wall of said receptacle, said pin being biased against said valve when said fluidic processing cartridge resides within said receptacle and said cartridge interfacing assembly is disengaged from said receptacle, wherein said cartridge interfacing assembly is capable of retracting said pin to open said valve.

18. The system according to claim 17 wherein said cartridge interfacing assembly comprises a gripping mechanism configured to grip said pin for retraction of said pin.

19. The system according to claim 17 wherein said cartridge interfacing assembly comprises a lever mechanism, and wherein said cartridge interfacing assembly is capable of retracting said pin to open said valve.

20. The system according to claim 19 wherein said lever mechanism is configured to bear against a surface of said receptacle and an underside of said pin.

21. The system according to claim 19 wherein said cartridge interfacing assembly comprises a camshaft, said camshaft comprising a cam, wherein said camshaft is rotatable such that said cam is contacted with said lever mechanism for opening said valve.

22. The system according to claim 19 wherein said lever mechanism comprises a lever positioned such that during centrifugation, a centrifugal force applied to said lever results in a compressive force applied to said valve.

* * * * *